(12) United States Patent
O'Dowd et al.

(10) Patent No.: US 9,018,216 B2
(45) Date of Patent: Apr. 28, 2015

(54) SOLID FORMS OF (R)-2-(5-(2-(3-ETHYLUREIDO)-6-FLUORO-7-(TETRAHYDROFURAN-2-YL)-1H-BENZO[D]IMIDAZOL-5-YL)PYRIMIDIN-2-YL)PROPAN-2-YL DIHYDROGEN PHOSPHATE AND SALTS THEREOF

(71) Applicants: Hardwin O'Dowd, Boston, MA (US); Dainius MacIkenas, Watertown, MA (US); Bin Song, Belmont, MA (US)

(72) Inventors: Hardwin O'Dowd, Boston, MA (US); Dainius MacIkenas, Watertown, MA (US); Bin Song, Belmont, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/945,257

(22) Filed: Jul. 18, 2013

(65) Prior Publication Data

US 2014/0031318 A1 Jan. 30, 2014

Related U.S. Application Data

(60) Provisional application No. 61/673,104, filed on Jul. 18, 2012.

(51) Int. Cl.
| | | |
|---|---|---|
| *A01N 43/54* | (2006.01) | |
| *C07D 239/42* | (2006.01) | |
| *C07D 471/04* | (2006.01) | |
| *C07F 9/6558* | (2006.01) | |
| *C07D 405/14* | (2006.01) | |
| *A61K 31/506* | (2006.01) | |
| *C07D 239/26* | (2006.01) | |

(52) U.S. Cl.
CPC .......... *C07F 9/65586* (2013.01); *C07D 405/14* (2013.01); *A61K 31/506* (2013.01); *C07D 239/26* (2013.01)

(58) Field of Classification Search
CPC ............................ C07D 239/26; A61K 31/506
USPC ............................................. 544/333; 514/256
See application file for complete search history.

(56) References Cited

U.S. PATENT DOCUMENTS

| | | | |
|---|---|---|---|
| 3,856,957 A | 12/1974 | Seng et al. | |
| 4,174,400 A | 11/1979 | Mrozik | |
| 4,512,998 A | 4/1985 | Nafissi-Varchei | |
| 5,529,998 A | 6/1996 | Habich et al. | |
| 5,643,935 A | 7/1997 | Dykstra et al. | |
| 6,069,160 A | 5/2000 | Stolle et al. | |
| 6,632,809 B2 | 10/2003 | Grillot et al. | |
| RE40,245 E | 4/2008 | Grillot et al. | |
| 7,414,046 B2 * | 8/2008 | Grillot et al. | 514/215 |
| 7,495,014 B2 | 2/2009 | Charifson et al. | |
| 7,569,591 B2 | 8/2009 | Charifson et al. | |
| 7,582,641 B2 | 9/2009 | Charifson et al. | |
| 7,618,974 B2 | 11/2009 | Charifson et al. | |
| 7,674,801 B2 | 3/2010 | Basarab et al. | |
| 7,727,992 B2 | 6/2010 | Charifson et al. | |
| 7,977,340 B2 | 7/2011 | Haydon et al. | |
| 8,034,832 B2 | 10/2011 | Charifson et al. | |
| 8,067,606 B2 | 11/2011 | Charifson et al. | |
| 8,188,095 B2 | 5/2012 | Charifson et al. | |
| 8,193,352 B2 | 6/2012 | Charifson et al. | |
| 8,404,852 B2 | 3/2013 | Charifson et al. | |

(Continued)

FOREIGN PATENT DOCUMENTS

| | | |
|---|---|---|
| EP | 0433648 | 6/1991 |
| EP | 0738726 | 10/1996 |

(Continued)

OTHER PUBLICATIONS

M. Falagas et al., 40 Clinical Infectious Diseases, 1333-1341 (2005).*

(Continued)

*Primary Examiner* — Alexander R Pagano
(74) *Attorney, Agent, or Firm* — Brinks Gilson & Lione

(57) ABSTRACT

The invention relates to solid forms of the Formula (I)

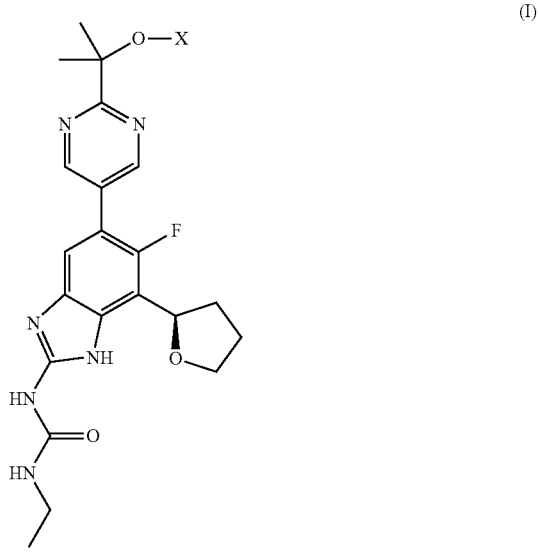

wherein X is —PO(OH)$_2$, —PO(OH)O$^-$M$^+$, or —PO(O$^-$)$_2$·2M$^+$, wherein M is a monovalent cation such as Na$^+$, K$^+$, Li$^+$, or NH$_4^+$. The invention also provides pharmaceutically acceptable compositions comprising the solid form of the compound and method of using the compositions in the treatment of various disorders.

28 Claims, 14 Drawing Sheets

(56) References Cited

U.S. PATENT DOCUMENTS

| | | | |
|---|---|---|---|
| 8,426,426 | B2 | 4/2013 | Charifson et al. |
| 8,471,014 | B2 | 6/2013 | Shannon et al. |
| 8,476,281 | B2 | 7/2013 | Shannon et al. |
| 8,481,551 | B2* | 7/2013 | Le Tiran et al. .............. 514/256 |
| 8,481,552 | B2 | 7/2013 | Shannon et al. |
| 2003/0119868 | A1 | 6/2003 | Grillot et al. |
| 2004/0043989 | A1 | 3/2004 | Grillot et al. |
| 2004/0235886 | A1 | 11/2004 | Charifson et al. |
| 2005/0038247 | A1 | 2/2005 | Charifson et al. |
| 2005/0256136 | A1 | 11/2005 | Charifson et al. |
| 2006/0025424 | A1 | 2/2006 | Charifson et al. |
| 2006/0122196 | A9 | 6/2006 | Charifson et al. |
| 2008/0132546 | A1 | 6/2008 | Basarab et al. |
| 2009/0176771 | A1 | 7/2009 | Charifson et al. |
| 2009/0197877 | A1 | 8/2009 | Haydon et al. |
| 2009/0325935 | A1 | 12/2009 | Charifson et al. |
| 2009/0325955 | A1 | 12/2009 | Charifson et al. |
| 2010/0063069 | A1 | 3/2010 | Charifson et al. |
| 2010/0105701 | A1 | 4/2010 | Charifson et al. |
| 2010/0311766 | A1 | 12/2010 | Haydon et al. |
| 2011/0104207 | A1 | 5/2011 | Charifson et al. |
| 2011/0166088 | A1 | 7/2011 | Sattigeri et al. |
| 2011/0263590 | A1 | 10/2011 | Haydon et al. |
| 2012/0004221 | A1 | 1/2012 | Haydon et al. |
| 2012/0010222 | A1 | 1/2012 | Charifson et al. |
| 2012/0184512 | A1 | 7/2012 | Le Tiran et al. |
| 2012/0184564 | A1* | 7/2012 | Shannon et al. .............. 514/256 |
| 2012/0184741 | A1* | 7/2012 | Shannon et al. .............. 544/333 |
| 2012/0184742 | A1* | 7/2012 | Shannon et al. .............. 544/333 |
| 2013/0157979 | A1* | 6/2013 | Bennani et al. ................. 514/80 |
| 2013/0261305 | A1 | 10/2013 | Shannon et al. |
| 2013/0267540 | A1 | 10/2013 | Shannon et al. |
| 2013/0289002 | A1 | 10/2013 | Le Tiran et al. |
| 2013/0317222 | A1 | 11/2013 | Shannon et al. |
| 2014/0031318 | A1 | 1/2014 | O'Dowd et al. |
| 2014/0045791 | A1 | 2/2014 | Locher et al. |

FOREIGN PATENT DOCUMENTS

| | | |
|---|---|---|
| EP | 1055668 | 11/2000 |
| WO | WO 99/35155 | 7/1999 |
| WO | WO 00/49015 | 8/2000 |
| WO | WO 00/71522 | 11/2000 |
| WO | WO 02/060879 | 8/2002 |
| WO | WO 03/105846 | 12/2003 |
| WO | WO 2005/012292 | 10/2005 |
| WO | WO 2006/022773 | 3/2006 |
| WO | WO 2007/056330 | 5/2007 |
| WO | WO 2007/148093 | 12/2007 |
| WO | WO 2008/068470 | 6/2008 |
| WO | WO 2009/074810 | 6/2009 |
| WO | WO 2009/074812 | 6/2009 |
| WO | WO 2009/156966 | 12/2009 |
| WO | WO 2011/032050 | 3/2011 |
| WO | WO 2011/047323 | 4/2011 |
| WO | WO 2012/045124 | 4/2012 |
| WO | WO 2012/097269 | 7/2012 |
| WO | WO 2012/097270 | 7/2012 |
| WO | WO 2012/097273 | 7/2012 |
| WO | WO 2012/177707 | 12/2012 |
| WO | WO 2013/138860 | 9/2013 |

OTHER PUBLICATIONS

A. Tanitame et al., 47 Journal of Medicinal Chemistry, 3693-3696 (2004).*

S. Alt et al., 66 Journal of Antimicrobial Chemotherapy, 2061-2069 (2011).*

Bradbury et al., 8 Current Opinion in Pharmacology, 574-581 (2008).*

Beers, M. H., and Berkow, R., "The Merck Manual of Diagnosis and Therapy", 7th Edition, Chapter 156—Bacteremia and Septic Shock, Merck Research Laboratories, Whitehouse Station, NJ pp. 1143-1147 (1999).

Champoux, J.J., Annu. Rev. Biochem., 2001, 70, pp. 369-413.

Charifson et al., J. Med. Chem., 2008, 51, pp. 5243-5263.

Charles W. Stratton, MD. "In Vitro Susceptibility Testing Versus in Vivo-Effectiveness" The Medical Clinics of North America 2006, 90, 1077-1088.

Drlica and Zhao, Microbiology and Molecular Biology Reviews, 1997, 61, pp. 377-392.

Joseph E. Drumm et al., "Facile preparation of fused ring azolylureas," 48 Tetrahedron Lett. 5535-5538 (2007).

Stephen P. East et al., "DNA gyrase (GyrB)/topoisomerase IV (ParE) inhibitors," 19 Bioorg. Med. Chem. Lett. 894-899 (2009).

Eckert et al., "The antifungal activity of . . . " CA 93:39290 (1980).

Gershman in The Medical Reporter, 1997.

Guven et al. "Synthesis and Antimicrobial Activity of Some Novel Furyl and Benzimidazole Substituted Benzyl Ethers" Journal of Heterocyclic Chemistry 2007, 44, 731.

He et al. "Synthesis and biological evaluation of novel benzimidazoles as potential antibacterial agents." Bioorganic & Medicinal Chemistry Letters 2004, 14, 1217-1220.

Hubschwerlen et al., "Pyrimido[1,6-1]benzimidazoles: A New Class of DNA Gyrase Inhibitors" J. Med. Chem, vol. 35, No. 8, pp. 1385-1392, 1992.

International Search Report and Written Opinion of the International Searching Authority, International Patent Application No. PCT/US2012/021270 (Mar. 16, 2012).

International Search Report and Written Opinion of the International Searching Authority, International Patent Application No. PCT/US2012/021281 (May 3, 2012).

International Search Report and Written Opinion of the International Searching Authority, International Patent Application No. PCT/US2012/021280 (Mar. 23, 2012).

International Search Report and Written Opinion of the International Searching Authority, International Patent Application No. PCT/US2012/021275 (Mar. 23, 2012).

International Search Report and Written Opinion of the International Searching Authority, International Patent Application No. PCT/US2012/043266 (Aug. 28, 2012).

International Search Report and Written Opinion of the International Searching Authority, International Patent Application No. PCT/US2012/051008 (Oct. 14, 2013).

International Search Report and Written Opinion of the International Searching Authority, International Patent Application No. PCT/US2012/050564 (Oct. 8, 2013).

Kornberg and Baker, DNA Replication, 2d Ed., Chapter 12, 1992, W. H. Freeman and Co.

Kus, C., "Synthesis and Antimicrobial Activities of 5-fluoro-1, 2, 6-trisubstituted benzimidazole carboxamide and acetamide derivatives," Arch. Pharm. Pharm. Med. Chem. 334(11):361-365 (2001).

Levy, "The Challenge of Antibiotic Resistance", Scientific American, Mar. 1998).

Lewis, "The Rise of Antibiotic-Resistant Infections", FDA Consumer magazine, Sep. 1995.

Maxwell, Mol. Microbiol., 1993, 9, 681.

Maxwell, Trends in Microbiology, 1997, 5, 102.

MayoClinic "Antibiotic associated diarrhea" Mayoclinic.com. (2007).

Nicolaus B.J.R., "Symbiotic Approach to Drug Design," Decision Making in Drug Research, pp. 173-186 (1983).

Pea et al., PubMed Abstract (Clin Pharmacokinet. 44(10):1009-34) 2005.

Singh, S.K., et al., "Studies in antiparastic agents: Part 13—Synthtesis of 4-aryl-2-substitutedamino-thiazoles as potential anthelmintics," Indian J. Chem., 28B (9):786-789 (1989).

Skopenka, V.V., et al., "Organotin Carbamoyldicyanomethanide, nitrosocarbamoylcyanomethanide, and Carbamoylcyanides," retrieved from STN Database accession No. 101:230674, XP002254350 abstract and Dopovidi Akademii Nauk Ukrains'Koi RSR, Seriya B: Geologichni, Khimichni Ta Biologichni Nauki, 7:44-46 (1984).

Snyder et al., PubMed Abstract (J. Med Liban. 48(4):208-14), Jul.-Aug. 2000.

(56) References Cited

OTHER PUBLICATIONS

Sun et al., "Synthesis and Evaluation of Terbenzimidazoles as Topoisomerase I Inhibitors" J. Med. Chem., vol. 38, No. 18, pp. 3638-3644, 1995.

Tanitame et al. "Design, synthesis and structure-activity relationship studies of novel indazole analogues as DNA gyrase inhibitors with Gram-positive antibacterial activity" Bioorganic & Medicinal Chemistry Letters 2004, 14, 2857-2862.

Drlica, Molecular Microbiology, 1992, 6, 425.

Wassenaar "Bacteria; more than pathogens" Am. Ins. Biol. Sci. Internet p. 1-7 (2002).

Webster's Dictionary (1984) p. 933.

WHO Report, "Use of Quinolones in Food Animals and Potential Impact on Human Health", 1998.

Matthew E. Falagas et al., "Colistin: The Revival of Polymyxins for the Management of Multidrug-Resistant Gram-Negative Bacterial Infections," *Reviews of Anti-Infective Agents*, CID 2005:40 (2005), pp. 1333-1341.

Silke Alt, Lesley A. Mitchenall, Anthony Maxwell, and Lutz Heide, "Inhibition of DNA gyrase and DNA topoisomerase IV of *Staphylococcus aureaus* and *Escherichia coli* by aminocoumarin antibiotics," *Journal of Antimicrobial Chemotherapy* 66; pp. 2061-2069; (2011).

Barton J. Bradbury and Michael J. Pucci, "Recent advances in bacterial topoisomerase inhibitors," *Current Opinion in Pharmacology* 8, pp. 574-581; (2008).

Chabner, Bruce A. et al., "Antineoplastic Agents," *The Pharmacological Basics of Therapeutics* 11$^{th}$ edition, Chapter 51; pp. 1315-1403; (2006).

Poupaert, Jacques H., "Drug Design: Basic Principles and Application," *Encyclopedia of Pharmaceutical Technology*; pp. 1362-1369; (2007).

Akihiko Tanitame et al., "Synthesis and Antibacterial Activity of Novel Series of Potent DNA Gyrase Inhibitors. Pyrazole Derivatives," *J. Med. Chem.* 47; pp. 3693-3696; (2004).

\* cited by examiner

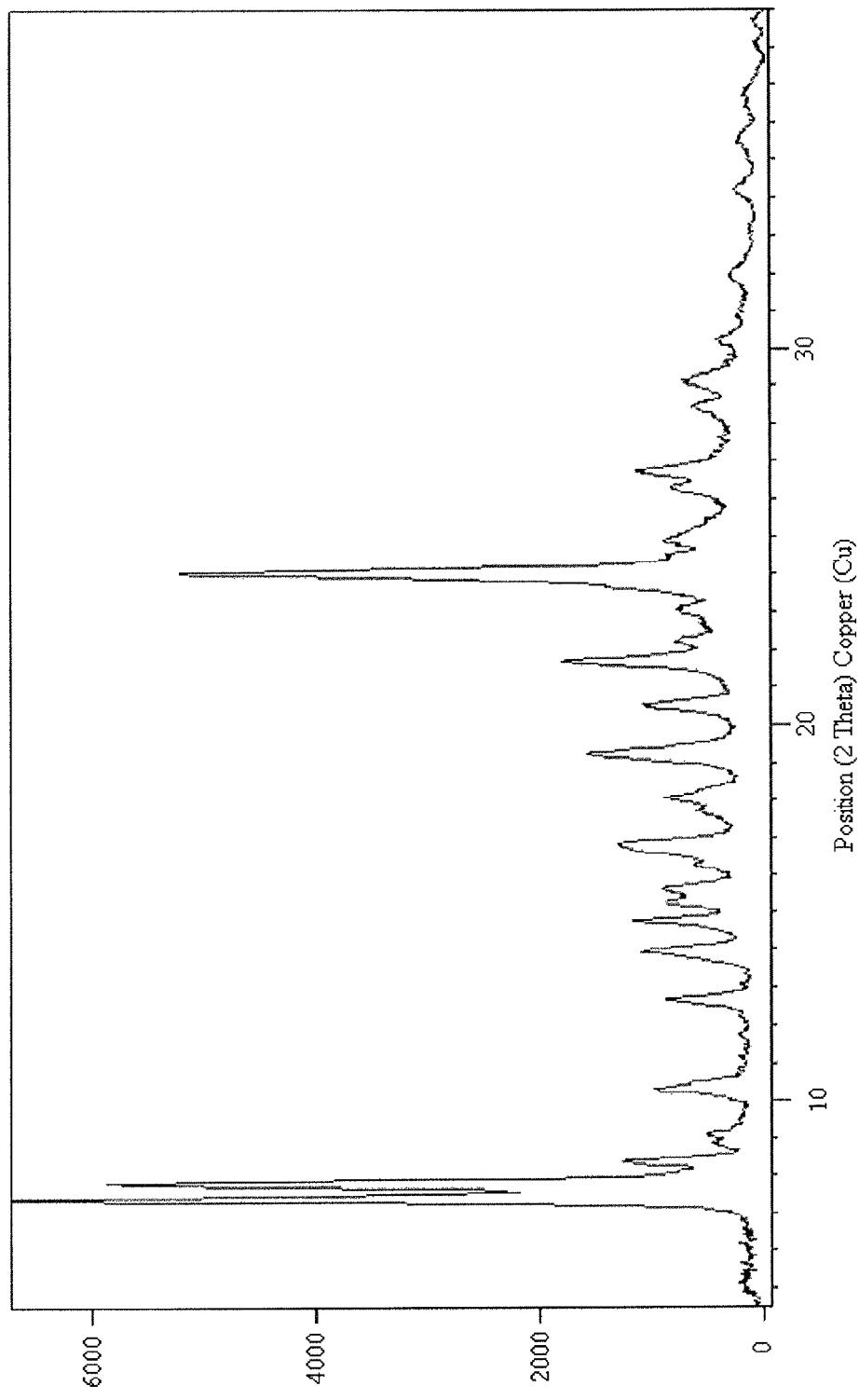
Figure 1: XRPD of Free Form A.

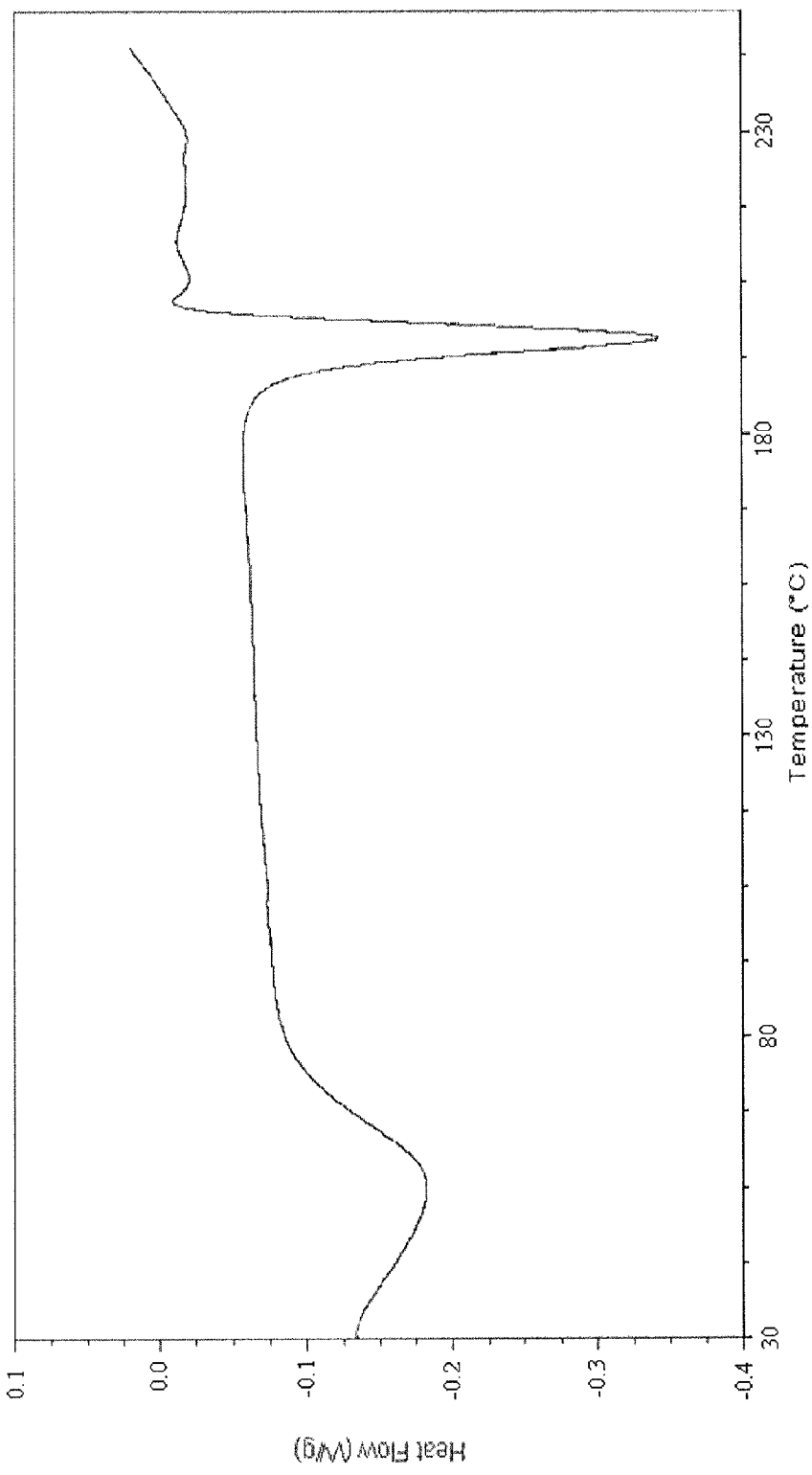
Figure 2: DSC of Free Form A.

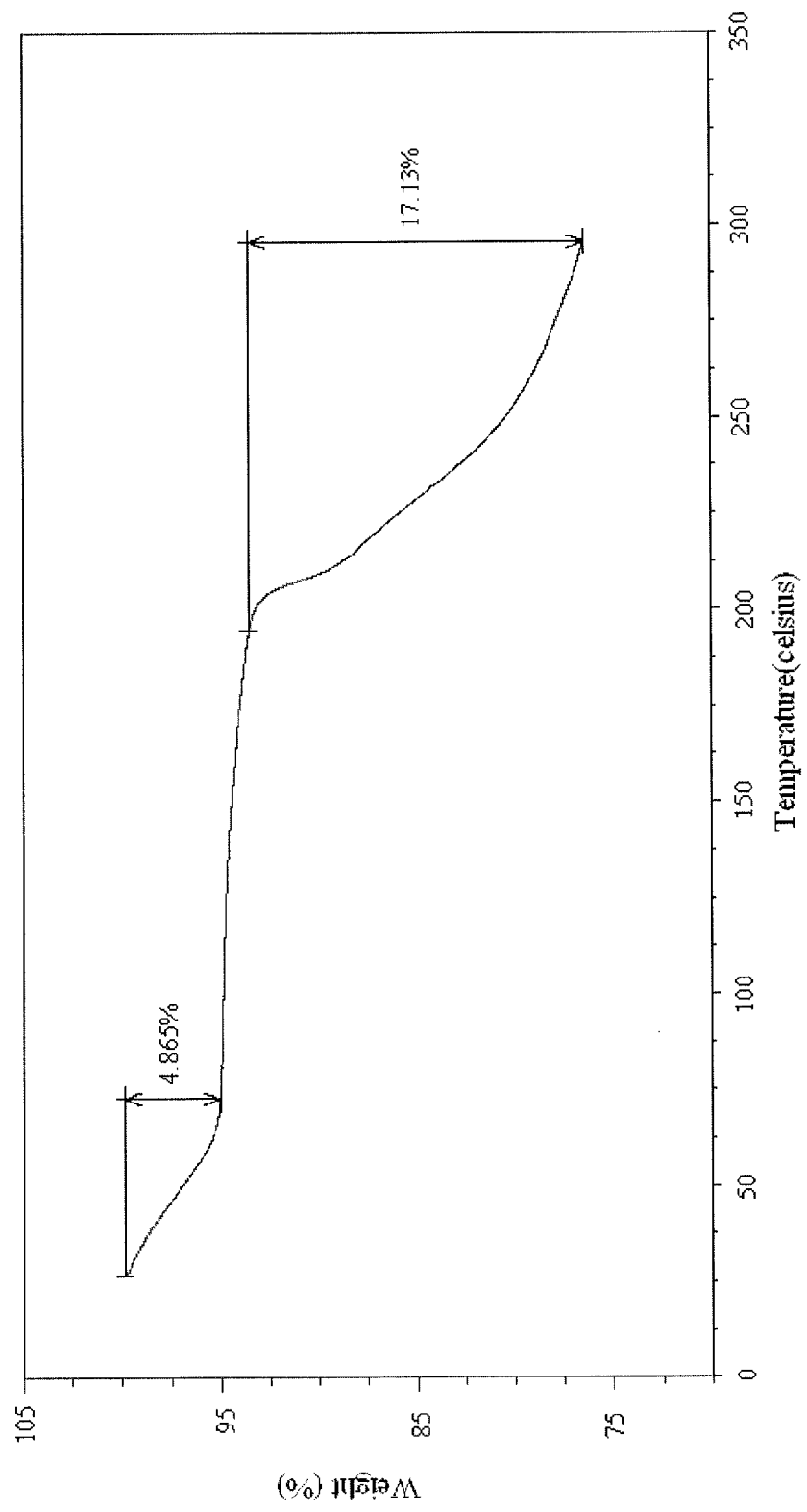
Figure 3: TGA of Free Form A.

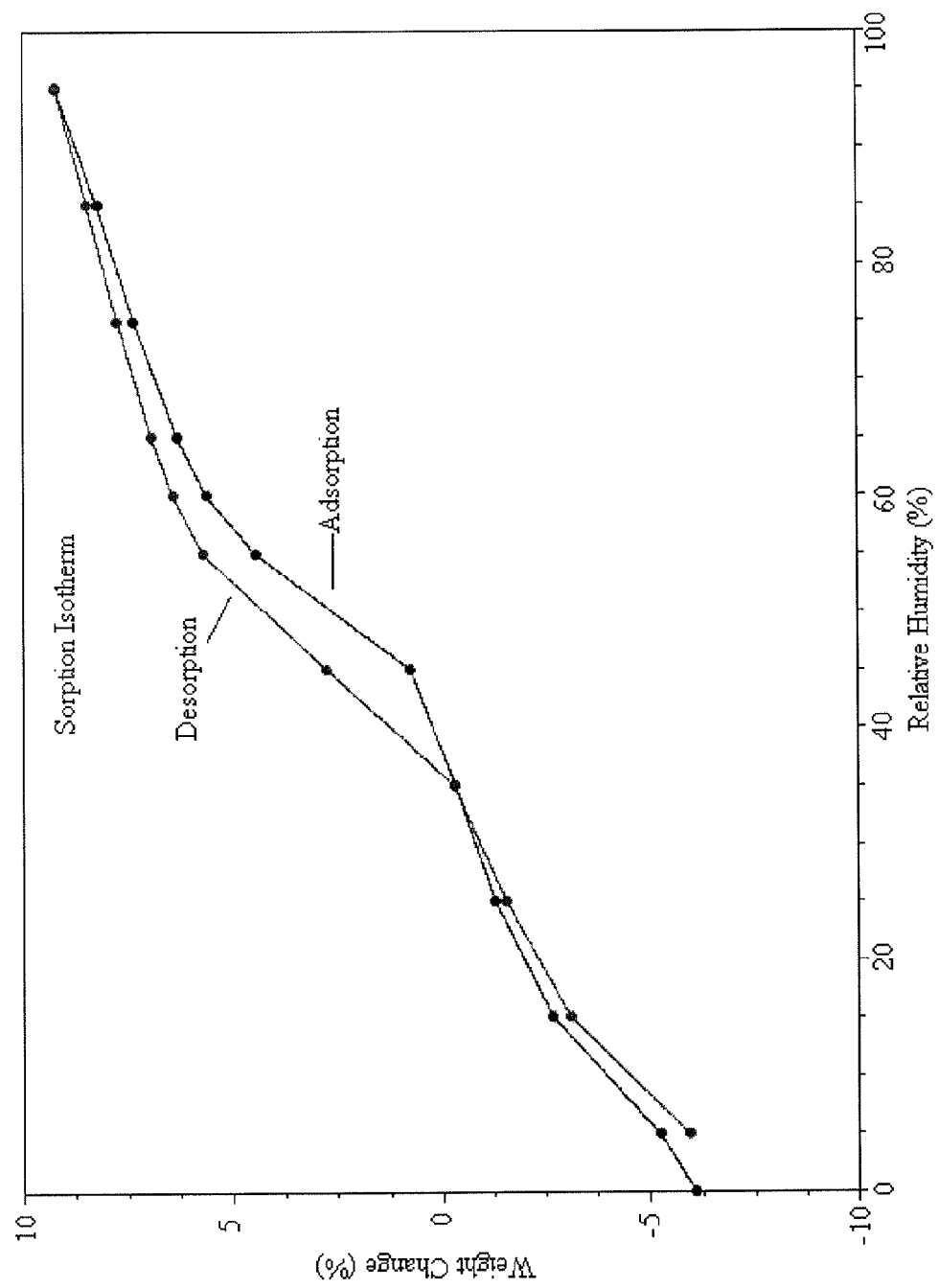
Figure 4: Vapor Sorption isotherm of Free Form A.

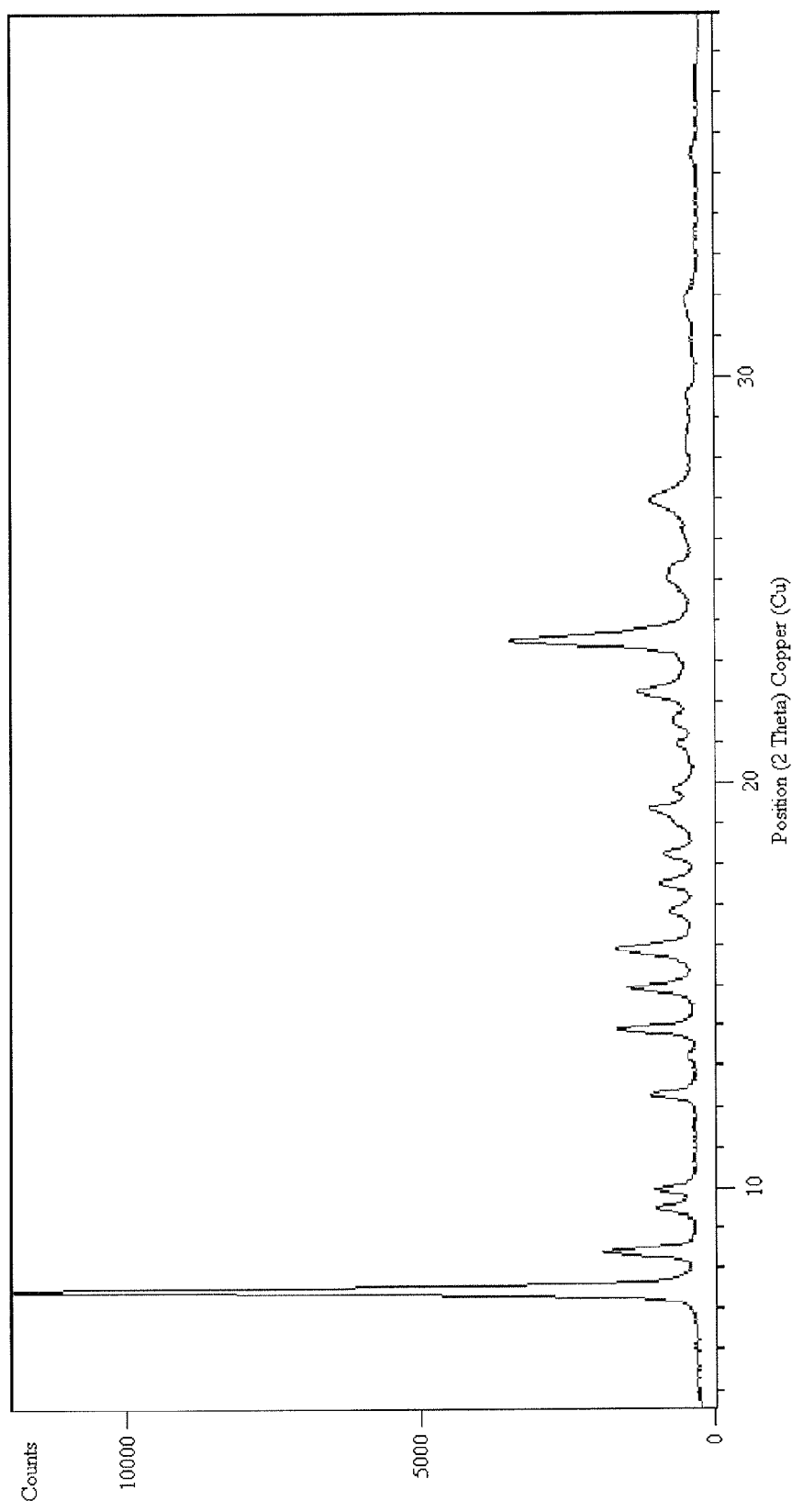
Figure 5. XRPD of Free Form B.

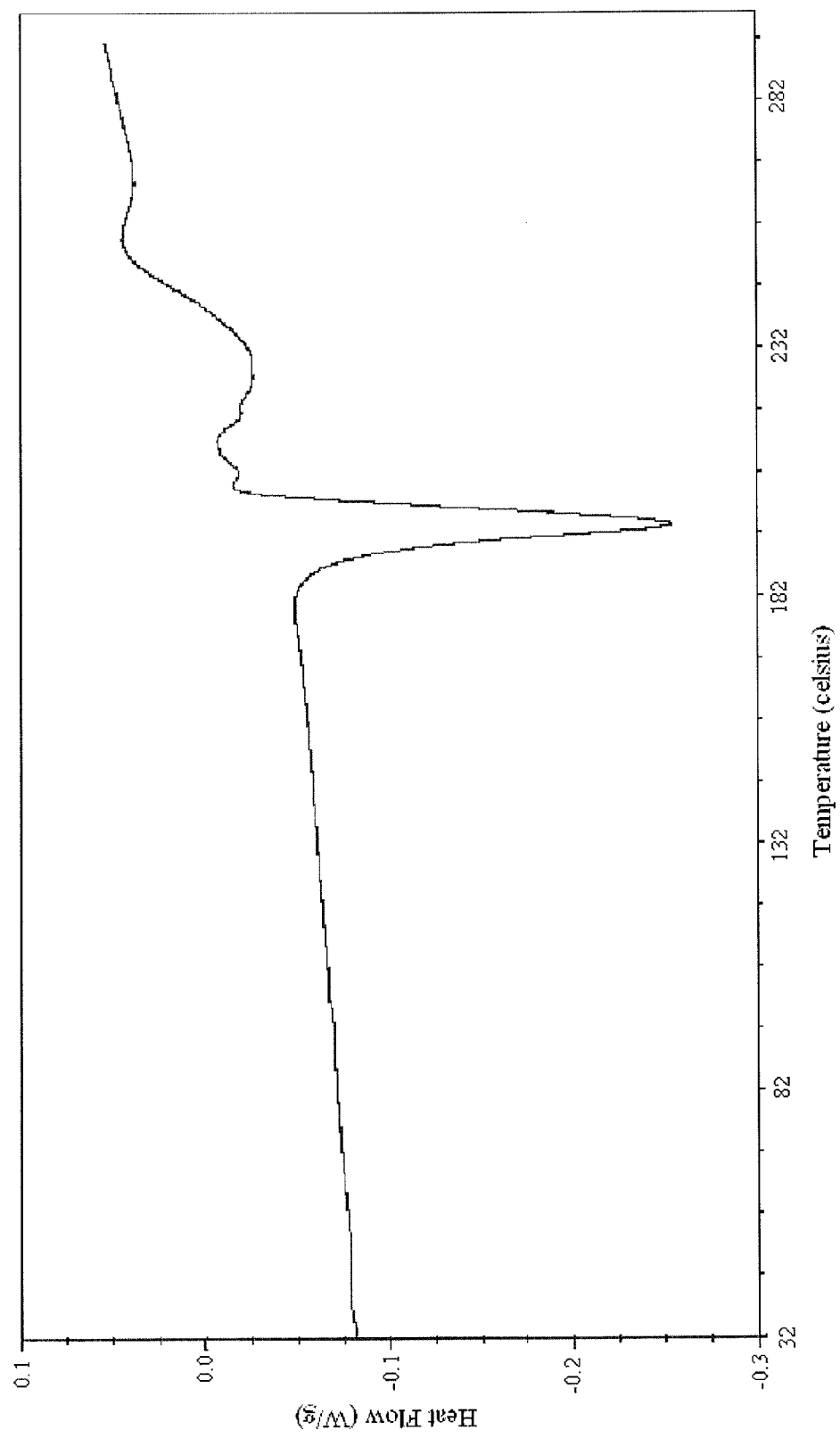
Figure 6. DSC of Free Form B.

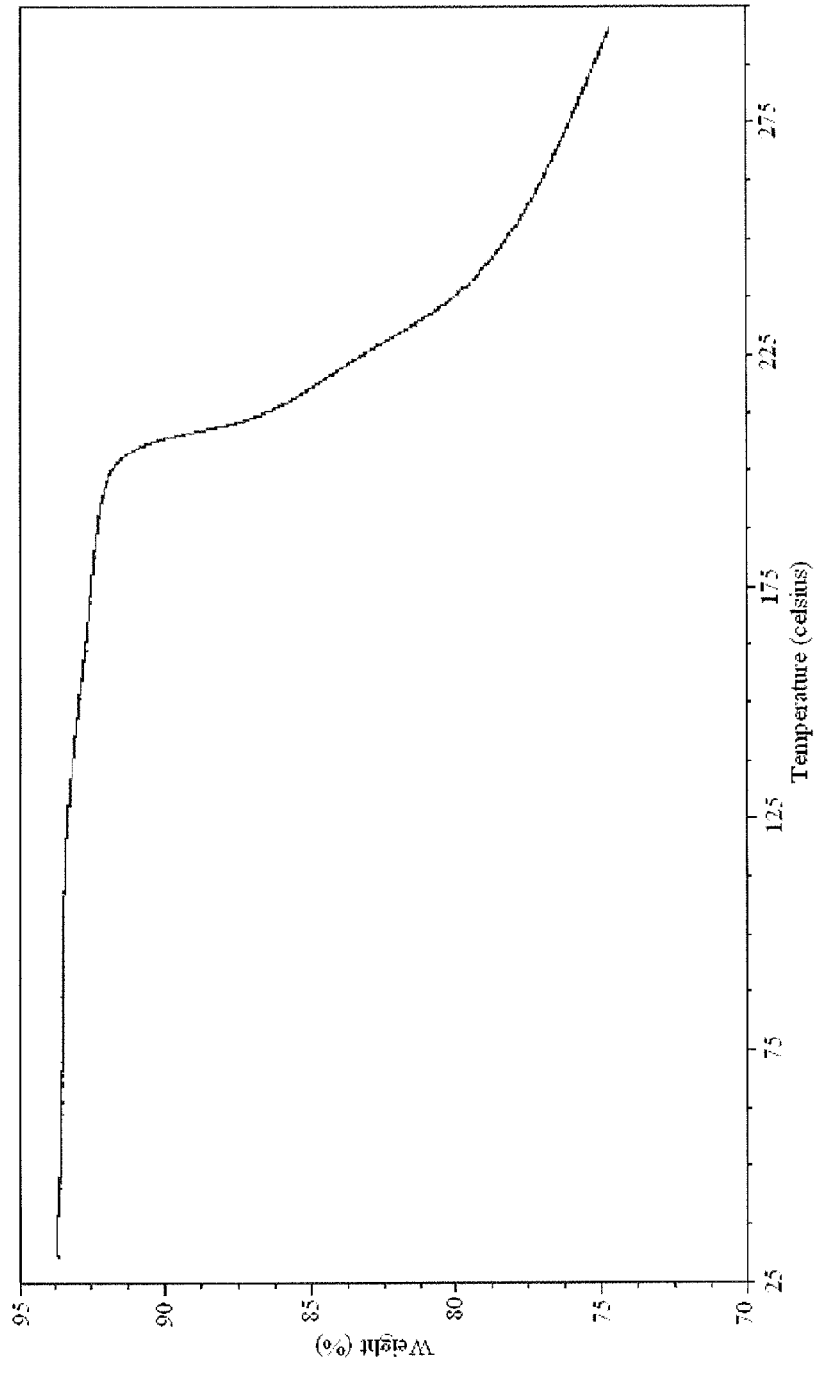
Figure 7. TGA of Free Form B

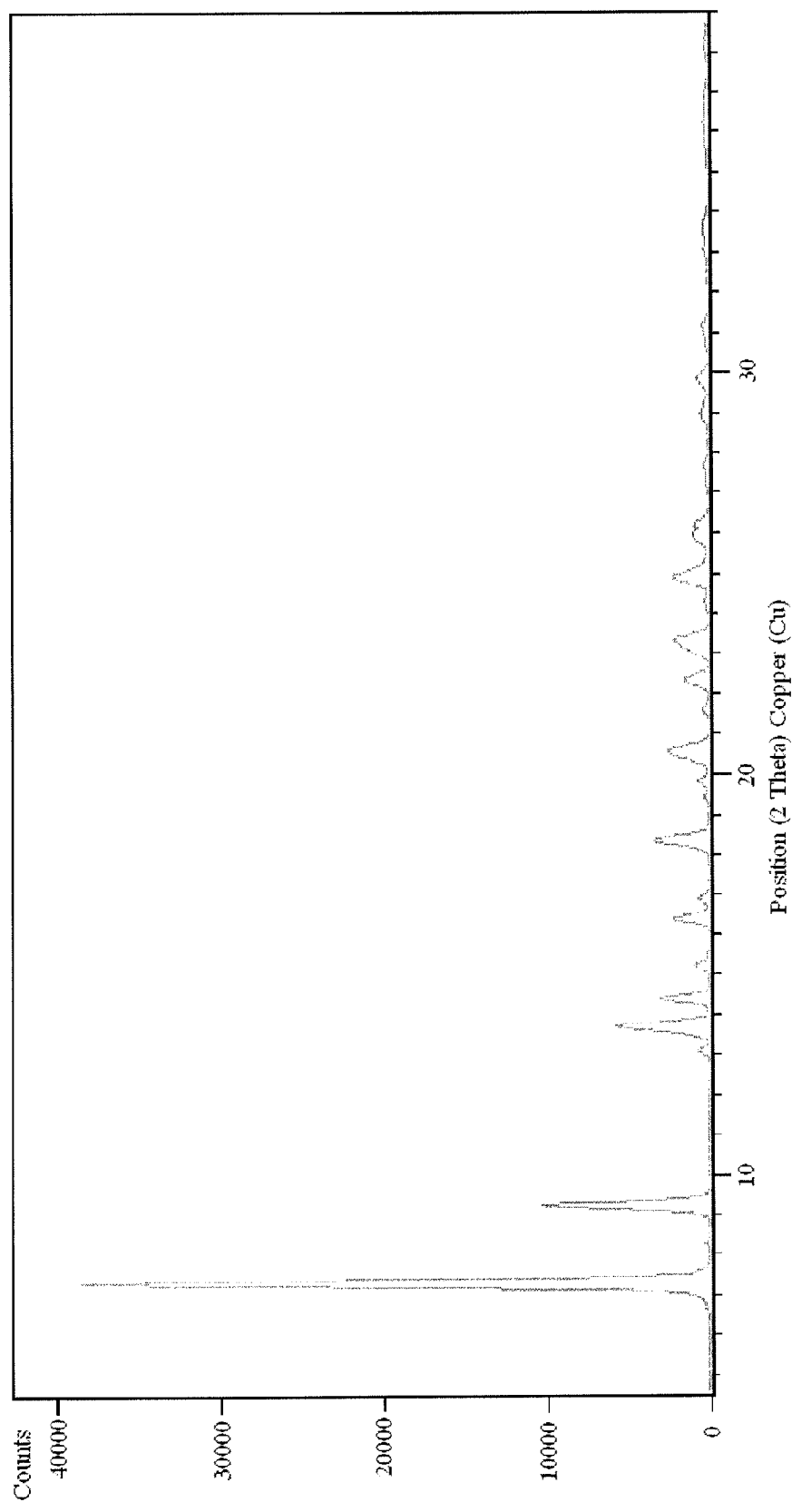
Figure. 8: XRPD of Free Form C.

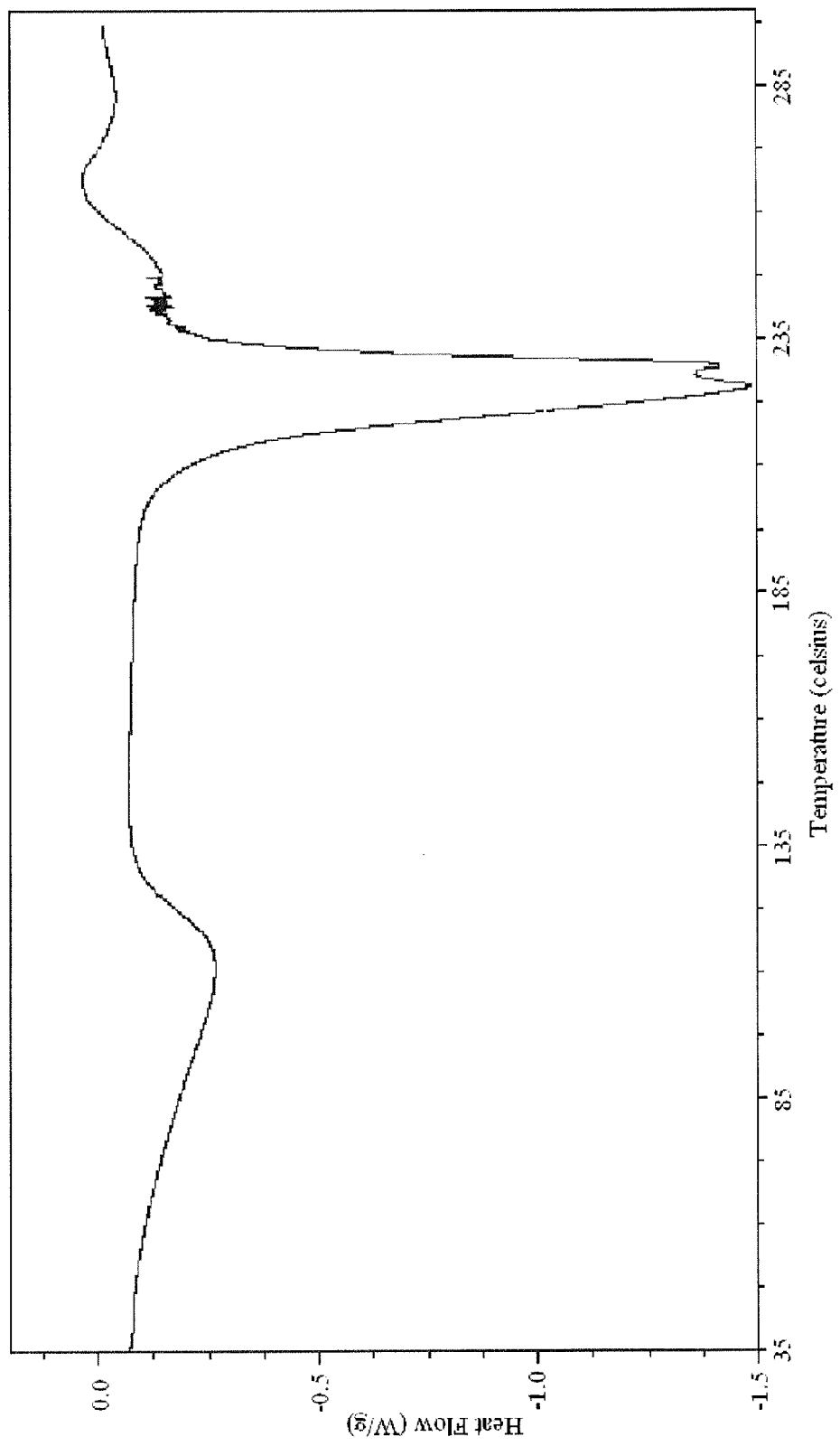
Figure. 9: DSC of Free Form C.

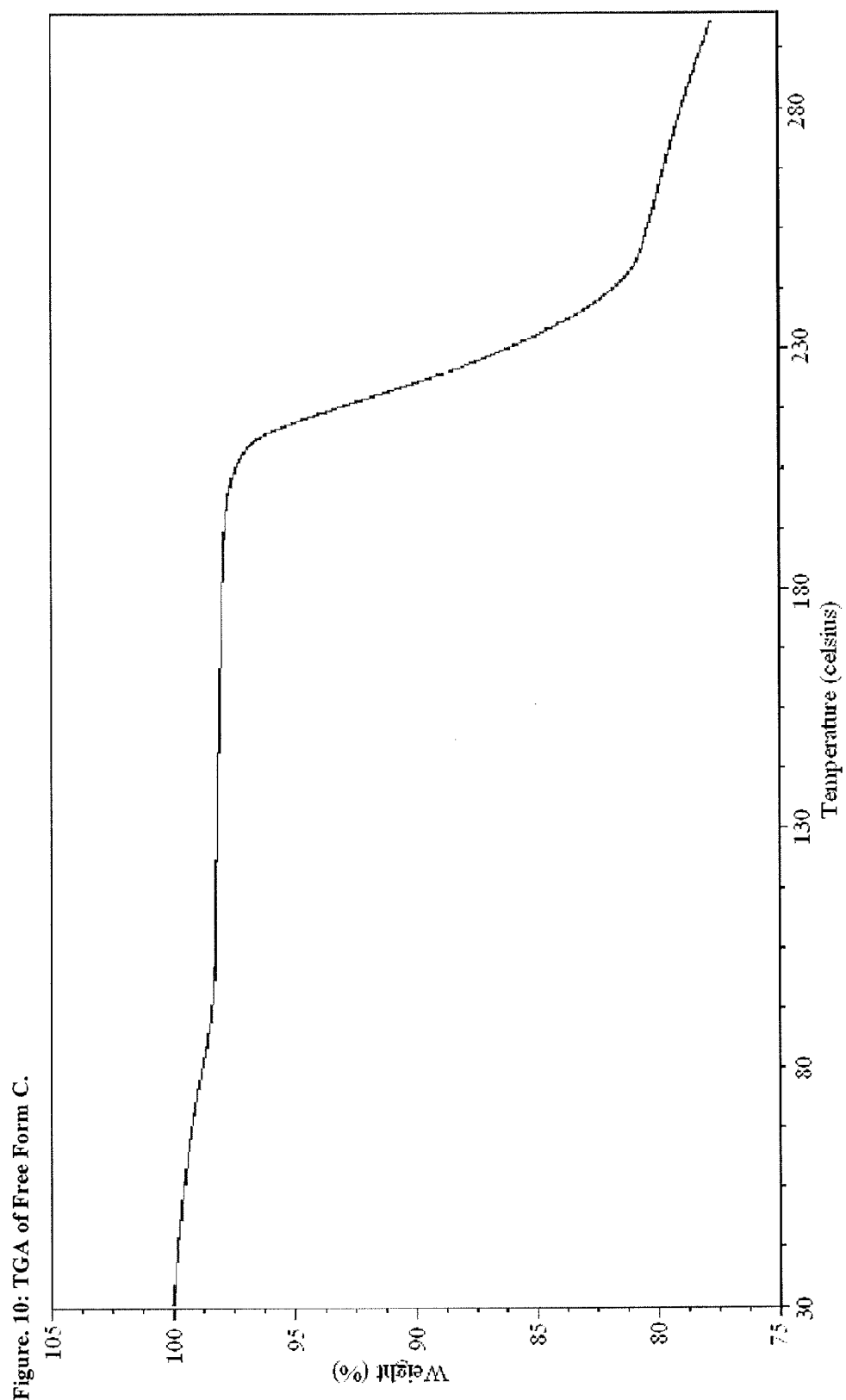
Figure. 10: TGA of Free Form C.

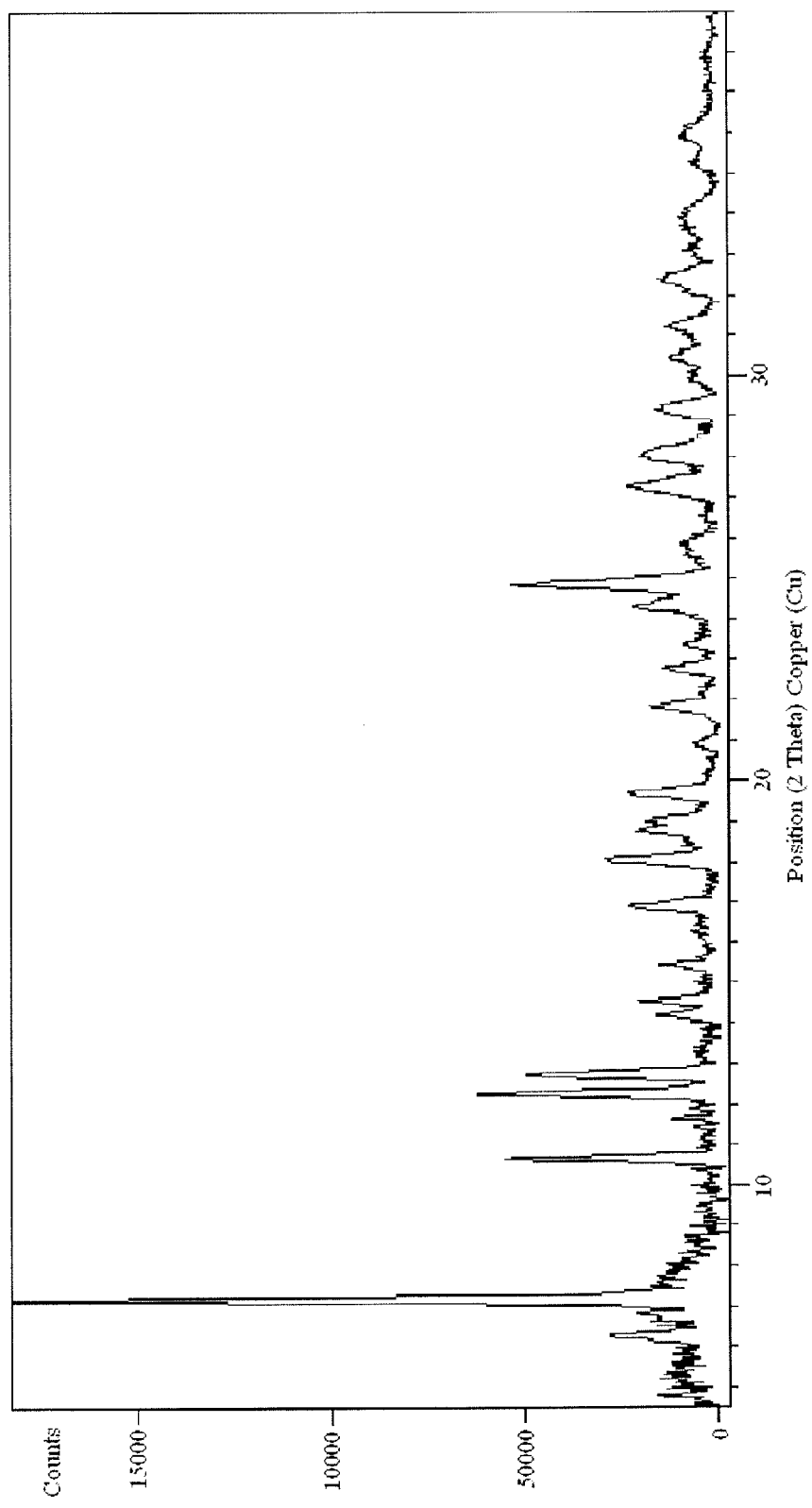
Figure. 11: PXRD of Salt Form X.

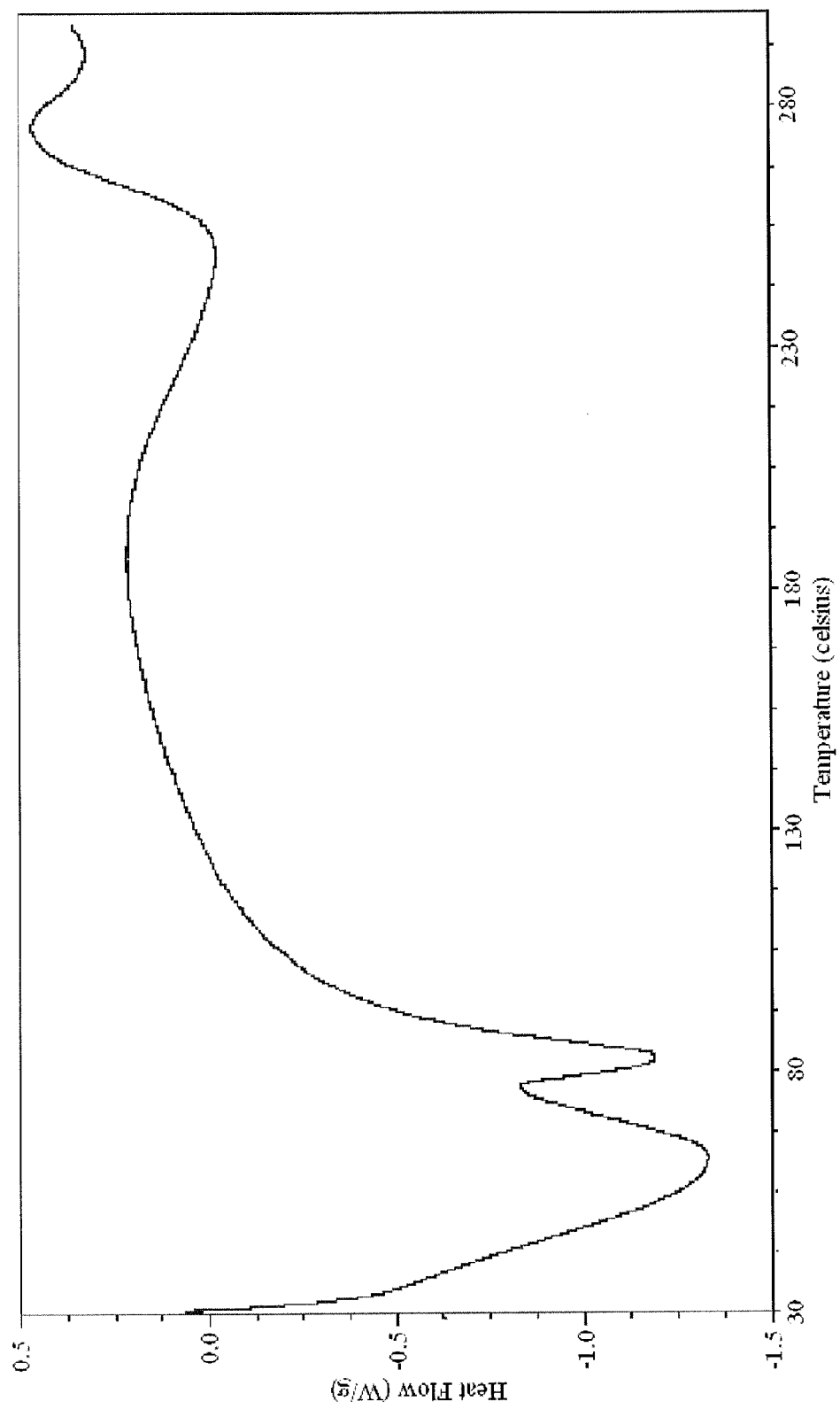
Figure 12: DSC of Salt Form X.

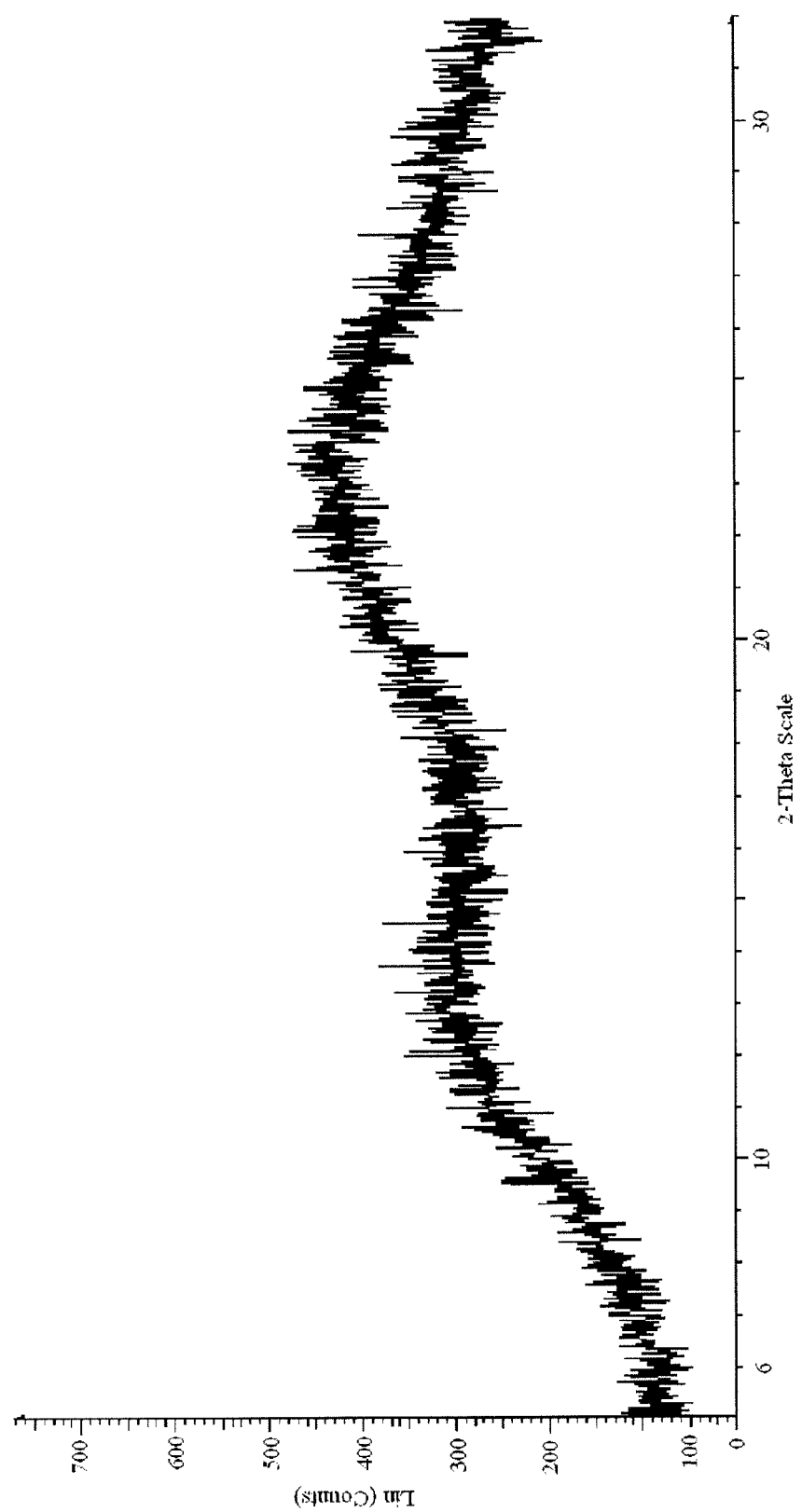
Figure 13. XRPD of Amorphous di-Sodium salt

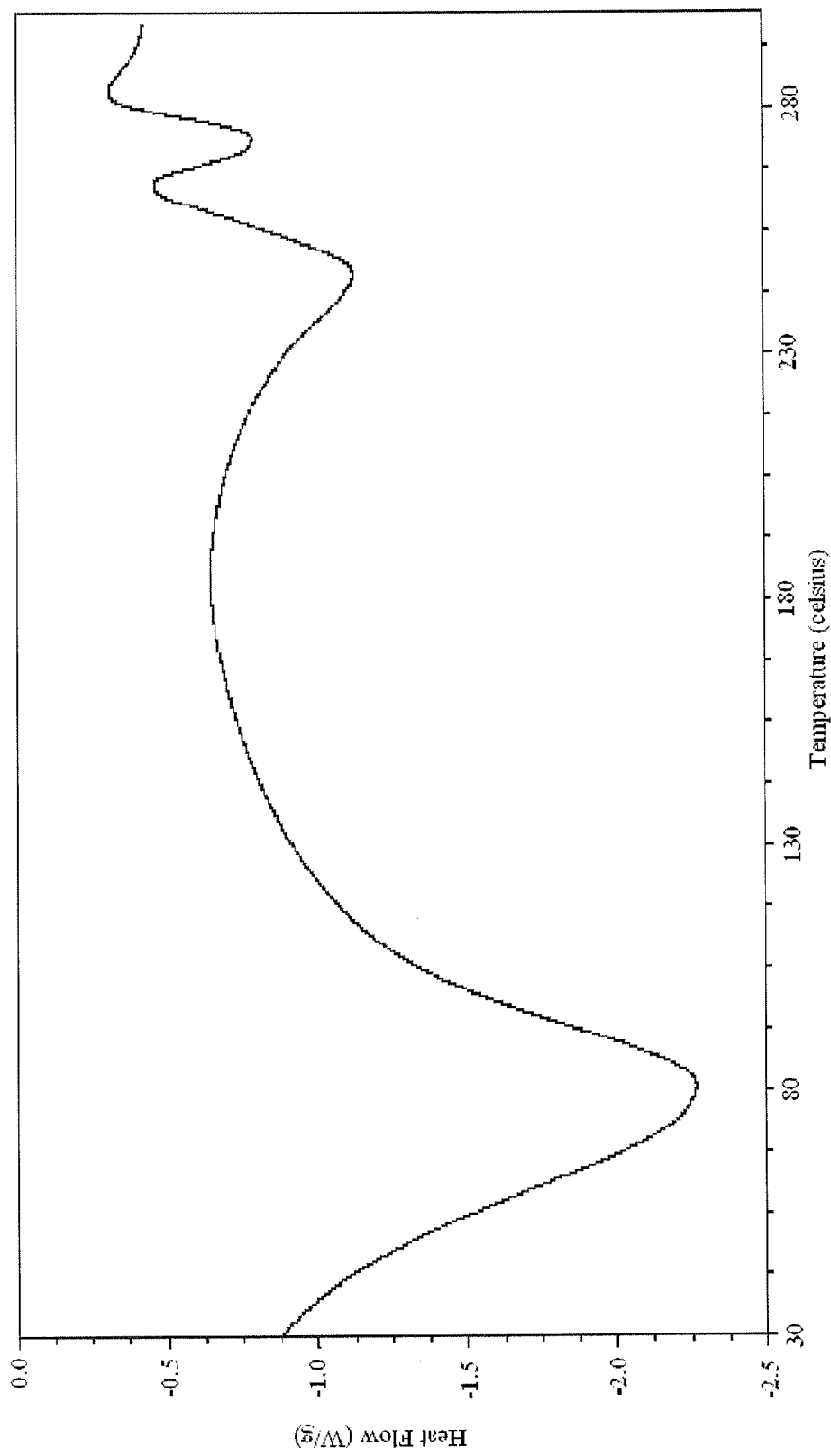
Figure 14. DSC of Amorphous di-Sodium salt

SOLID FORMS OF (R)-2-(5-(2-(3-ETHYLUREIDO)-6-FLUORO-7-(TETRAHYDROFURAN-2-YL)-1H-BENZO[D]IMIDAZOL-5-YL)PYRIMIDIN-2-YL)PROPAN-2-YL DIHYDROGEN PHOSPHATE AND SALTS THEREOF

CROSS-REFERENCE TO RELATED APPLICATION

This application claims benefit of U.S. Provisional Application No. 61/673,104, filed Jul. 18, 2012, the entire contents of which is hereby incorporated herein by reference.

BACKGROUND OF THE INVENTION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *Mycobacterium tuberculosis*, and *Enterococcus*. The appearance of Vancomycin resistant *enterococcus* was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., Current Opinion in Anti-infective Investigational Drugs, 1999, 1, 1; Levy, "The Challenge of Antibiotic Resistance", Scientific American, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in The Medical Reporter, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", FDA Consumer magazine, September 1995).

As a result of the need to combat drug-resistant bacteria and the increasing failure of the available drugs, there has been a resurgent interest in discovering new antibiotics. One attractive strategy for developing new antibiotics is to inhibit DNA gyrase and/or topoisomerase IV, bacterial enzymes necessary for DNA replication, and therefore, necessary for bacterial cell growth and division. Gyrase and/or topoisomerase IV activity are also associated with events in DNA transcription, repair and recombination.

Gyrase is one of the topoisomerases, a group of enzymes which catalyze the interconversion of topological isomers of DNA (see generally, Kornberg and Baker, DNA Replication, 2d Ed., Chapter 12, 1992, W.H. Freeman and Co.; Drlica, Molecular Microbiology, 1992, 6, 425; Drlica and Zhao, Microbiology and Molecular Biology Reviews, 1997, 61, pp. 377-392). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase and/or topoisomerase IV would be selective for these enzymes and be relatively inactive against the eukaryotic type II topoisomerases.

Topoisomerase IV primarily resolves linked chromosome dimers at the conclusion of DNA replication.

The widely-used quinolone antibiotics inhibit bacterial DNA gyrase (GyrA) and/or Topoisomerase IV (ParC). Examples of the quinolones include the early compounds such as nalidixic acid and oxolinic acid, as well as the later, more potent fluoroquinolones such as norfloxacin, ciprofloxacin, and trovafloxacin. These compounds bind to GyrA and/or ParC and stabilize the cleaved complex, thus inhibiting overall gyrase function, leading to cell death. The fluoroquinolones inhibit the catalytic subunits of gyrase (GyrA) and/or Topoisomerase IV (Par C) (see Drlica and Zhao, Microbiology and Molecular Biology Reviews, 1997, 61, 377-392). However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

The associated subunits responsible for supplying the energy necessary for catalytic turnover/resetting of the enzymes via ATP hydrolysis are GyrB (gyrase) and ParE (topoisomerase IV), respectively (see, Champoux, J. J., Annu. Rev. Biochem., 2001, 70, pp. 369-413). Compounds that target these same ATP binding sites in the GyrB and ParE subunits would be useful for treating various bacterial infections (see, Charifson et al., J. Med. Chem., 2008, 51, pp. 5243-5263).

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, Trends in Microbiology, 1997, 5, 102).

For coumarin-resistant bacteria, the most prevalent point mutation is at a surface arginine residue that binds to the carbonyl of the coumarin ring (Arg136 in *E. coli* GyrB). While enzymes with this mutation show lower supercoiling and ATPase activity, they are also less sensitive to inhibition by coumarin drugs (Maxwell, Mol. Microbiol., 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, Trends in Microbiology, 1997, 5, 102). It would be desirable to have a new, effective GyrB and ParE inhibitor that overcomes these drawbacks and, preferably does not rely on binding to Arg136 for activity. Such an inhibitor would be an attractive antibiotic candidate, without a history of resistance problems that plague other classes of antibiotics.

As bacterial resistance to antibiotics has become an important public health problem, there is a continuing need to develop newer and more potent antibiotics. More particularly, there is a need for antibiotics that represent a new class of compounds not previously used to treat bacterial infection. Compounds that target the ATP binding sites in both the GyrB (gyrase) and ParE (topoisomerase IV) subunits would be useful for treating various bacterial infections. Such compounds would be particularly useful in treating nosocomial infections in hospitals where the formation and transmission of resistant bacteria are becoming increasingly prevalent. Furthermore, there is a need for new antibiotics having a broad spectrum of activity with advantageous toxicological properties.

SUMMARY OF THE INVENTION

The present application is directed to novel substantially pure solid forms of the compound of formula (I):

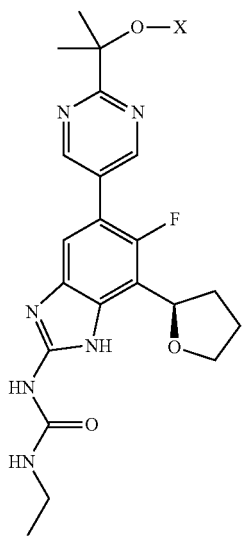

(I)

wherein X is
—PO(OH)$_2$, —PO(OH)O$^-$M$^+$,
—PO(O$^-$)$_2$.2M$^+$, wherein M$^+$ is a pharmaceutically acceptable monovalent cation such as Na$^+$, K$^+$, Li$^+$, or NH$_4^+$.

In one embodiment, the solid form is Free Form A, characterized by an X-ray powder diffraction pattern (XPRD) comprising at least three approximate peak positions (degrees 2θ±0.2) when measured using Cu K$_\alpha$ radiation, selected from the group consisting of 7.4, 7.8, 8.4, 14.0, 14.8, 16.8, 19.2, 20.5, 21.7, 24.0, and 26.7, when the XPRD is collected from about 5 to about 38 degrees two theta (2θ). In one embodiment, Free Form A may be prepared by isolating the solid from an aqueous acidic solution.

In another embodiment, the solid form is Free Form B, characterized by an X-ray powder diffraction pattern (XPRD) comprising at least three approximate peak positions (degrees 2θ±0.2) when measured using Cu K$_\alpha$ radiation, selected from the group consisting of 7.5, 8.4, 13.9, 14.9, 15.9, and 23.5 when the XPRD is collected from about 5 to about 38 degrees 2θ.

In another embodiment, the solid form is Free Form C, characterized by an X-ray powder diffraction pattern (XPRD) comprising at least three approximate peak positions (degrees 2θ±0.2) when measured using Cu K$_\alpha$ radiation, selected from the group consisting of 7.3, 9.2, 13.7, 14.4, and 18.4 when the XPRD is collected from about 5 to about 38 degrees 2θ.

In certain embodiments, the compound of formula (I) exists as a sodium Salt Form of the compound of formula (IA):

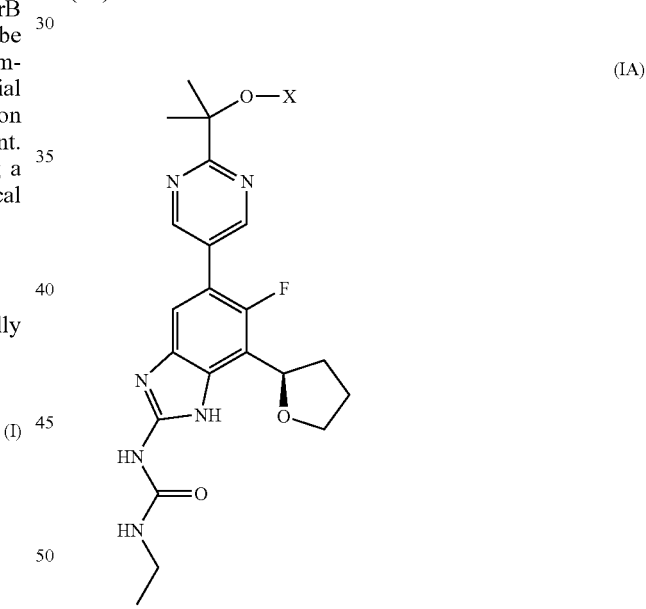

(IA)

wherein X is
—PO(OH)O$^-$M$^+$ or
—PO(O$^-$)$_2$.2M$^+$, wherein M$^+$ is a Na$^{++}$.

In one embodiment, the compound of formula (IA) forms di-sodium Salt Form X, which is characterized by an X-ray powder diffraction pattern (XPRD) comprising at least three approximate peak positions (degrees 2θ±0.2) when measured using Cu K$_\alpha$ radiation, selected from the group consisting of 6.3, 7.2, 10.7, 12.3, 12.7, 14.6, 16.9, 18.1, 18.8, 19.0, 19.69, 24.3, 24.9, and 27.3, when the XPRD is collected from about 5 to about 38 degrees 2θ. In another embodiment, di-sodium Salt Form X may be prepared by isolating the compound of formula (IA) from an aqueous solution at a pH greater than 8.0.

Further embodiments include pharmaceutical compositions comprising the compound of Formula (I), optionally with a pharmaceutically acceptable carrier, an adjuvant, or a vehicle; a method of decreasing or inhibiting *Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium tuberculosis, Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci bacterial quantity in a biological sample comprising contacting said biological sample with a compound of Formula (I); a method of controlling, treating or reducing the advancement, severity or effects of a nosocomial or a non-nosocomial bacterial infection in a patient, comprising administering to said patient a compound of Formula (I).

BRIEF DESCRIPTION OF THE DRAWINGS

FIG. 1 shows an X-ray powder diffraction pattern of Free Form A of the compound of formula (I) (free base) collected from about 3 to about 40 degrees 2θ.

FIG. 2 shows a DSC thermogram of Free Form A of the compound of formula (I).

FIG. 3 shows a TGA (thermal gravimetric analysis) thermogram of Free Form A of the compound of formula (I).

FIG. 4 shows a Vapor Sorption isotherm of Free Form A of the compound of formula (I).

FIG. 5 shows an X-ray powder diffraction pattern of Free Form B of the compound of formula (I) collected from about 3 to about 40 degrees 2θ.

FIG. 6 shows a DSC thermogram of Free Form B of the compound of formula (I).

FIG. 7 shows a TGA (thermal gravimetric analysis) thermogram of Free Form B of the compound of formula (I).

FIG. 8 shows an X-ray powder diffraction pattern of Free Form C of the compound of formula (I) (free base) collected from about 3 to about 40 degrees 2θ.

FIG. 9 shows a DSC thermogram of Free Form C of the compound of formula (I).

FIG. 10 shows a TGA (thermal gravimetric analysis) thermogram of Free Form C of the compound of formula (I).

FIG. 11 shows an X-ray powder diffraction pattern of di-sodium salt Form X of the compound of formula (I) collected from about 3 to about 40 degrees 2θ.

FIG. 12 shows a DSC thermogram of di-sodium salt Form X of the compound of formula (I).

FIG. 13 shows an X-ray powder diffraction pattern of amorphous di-sodium salt of the compound of formula (I) collected from about 5 to about 32 degrees 2θ.

FIG. 14 shows a DSC thermogram of amorphous di-sodium salt of the compound of formula (I).

DETAILED DESCRIPTION OF THE INVENTION

The present invention is directed to solid forms of (R)-2-(5-(2-(3-ethylureido)-6-fluoro-7-(tetrahydrofuran-2-yl)-1H-benzo[d]imidazol-5-yl)pyrimidin-2-yl)propan-2-yl dihydrogen phosphate ("the compounds of Formula (I)") as a free acid form(s) or a salt form(s). The compounds of Formula (I) are prodrugs of a compound useful as gyrase and/or topoisomerase IV inhibitors and pharmaceutically acceptable salts thereof. The compounds of Formula (I) may be represented by:

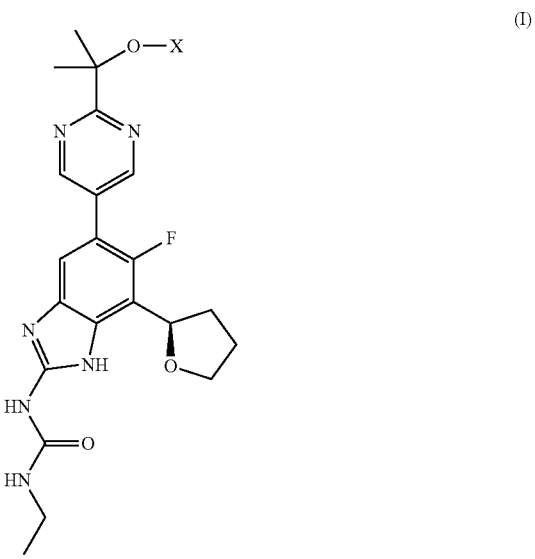

wherein X is —PO(OH)$_2$ or —PO(OH)O$^-$M$^+$, or —PO(O)$_2$.2M$^+$, wherein M is a monovalent cation such as Na$^+$, K$^+$, Li$^+$, or NH$_4^+$. The compounds of formula (I) are phosphate ester prodrugs of the compound (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, which possesses a broad range of anti-bacterial activity and advantageous toxicological properties. In addition to the compounds provided herein, the present invention further provides a pharmaceutical composition comprising a compound of formula (I) or a pharmaceutically acceptable salt thereof and a pharmaceutically acceptable carrier.

The inventors have discovered that the compounds of formula (I) can exist in a number of solid forms, including hydrated and dehydrated free acid forms (when X is —PO(OH)$_2$) and salt forms (when X is —PO(OH)O$^-$M$^+$—PO(O$^-$)$_2$.2M$^+$). Among these solid forms exhibited by the compound of formula (I) are a hydrated crystalline form of the free acid (free Form A as described below), an anhydrous crystalline form of the free acid (free Form B as described below), a hydrated crystalline form of the di-sodium salt (di-sodium salt form X as described below) and an amorphous di-sodium salt of the compound of formula (I).

In one embodiment, the present application provides Free Form A of the compound of formula (I), which is characterized by an X-ray powder diffraction pattern (XPRD) comprising at least three approximate peak positions (degrees 2θ±0.2) when measured using Cu K$_α$ radiation, selected from the group consisting of 7.4, 7.8, 8.4, 14.0, 14.8, 16.8, 19.2, 20.5, 21.7, 24.0, and 26.7, when the XPRD is collected from about 5 to about 38 degrees 2θ. Solid Form A may also be characterized by an X-ray powder diffraction pattern, as measured using Cu K$_α$ radiation, substantially similar to FIG. 1 and an endothermic peak having an onset temperature at about 190.4° C. as measured by differential scanning calorimetry in which the temperature is scanned at about 10° C. per minute.

One aspect of the present application is a novel Free Form A of the compound of formula (I). In one aspect, the present application provides a process for preparing Free Form A of the compound of formula (I).

A substantially pure Free Form A of the compound of formula (I) may be prepared from amorphous or crystalline free form or salt form of the compound comprising, if necessary, converting the salt of the compound to the free acid of the compound and contacting the free acid of the compound with a solvent in which the compound is soluble and isolating the free solid form by affecting crystallization. In one embodiment, the solvent is an aqueous solvent. In certain embodiments, an amorphous sodium salt of the compound may be dissolved in water, the resulting solution may be titrated with a solution of a suitable acid, for example hydrochloric acid, and the resulting solution/suspension is allowed to equilibrate at a suitable temperature such that the free acid crystallizes. Alternatively, an amorphous or crystalline form of the free acid may be recrystallized from an aqueous solvent at a suitable pH. In one embodiment, a suitable pH is from about 1 to about 4.

In other embodiments, crystallization may be affected from a solution of the compound of formula (I) by any method known to those skilled in the art. For example, to a solution of the compound in a suitable solvent may be added an antisolvent (i.e., a solvent in which the compound of formula (I) is not substantially soluble) until the solution becomes slightly cloudy. The cloudy solution/suspension may be allowed to stand for an extended period of time (for example, from a few hours to 24 hours or more) to generate Free Form A crystals.

In some embodiments, substantially pure Free Form A of the compound of formula (I) may be preparing by suspending a solid crystalline or amorphous material of the compound in a suitable solvent (slurry). Suitable solvents include mixtures of one or more organic solvents and water.

In one embodiment of the process, a substantially pure Free Form A of the compound of formula (I) may be prepared from amorphous or crystalline forms of the compound by preparing a saturated solution of the compound in a suitable solvent at a temperature above room temperature and isolating Free Form A which results upon cooling the solution. In practice this can be accomplished by dissolving a sufficient amount of the compound in the solvent at elevated temperature (up to reflux) such that when the solution is allowed to cool to room temperature a saturated solution is obtained, from which Free Form A precipitates and can be isolated. In other embodiments, the compound may be isolated from a reaction mixture by modifying the solubility of the compound in the solvent. For example, removing some or all of the solvent or lowering the mixture temperature may reduce the solubility of the compound and Free Form A may precipitate. Alternatively, adding a second solvent to the mixture may precipitate Free Form A of the compound.

Free Form A of the compound of formula (I) is a hydrated solid form which may be identified by one or more of the following characteristics: an X-ray powder diffraction pattern essentially as shown in Table 1 and FIG. 1 wherein the XRPD patterns were measured using a powder diffractometer equipped with a Cu X-ray tube source; and a melt endotherm with an extrapolated onset of about 190° C. as determined by differential scanning calorimetry using 10° C. per minute scan rate.

FIG. 1 is an X-ray powder diffraction pattern of Free Form A of the compound of formula (I). The X-ray powder diffractogram of the compound of formula (I) was acquired using a Bruker diffractometer with the sample loaded in a low-background Si holder at ambient temperature and humidity. The sample was illuminated with Cu K$\alpha_1$ radiation and XRPD data were collected from 3 to 40° 2θ. The XRPD result shows strong diffractions peaks (location in degree 2θ) at 7.4, 7.8, and 24.0, degree 2θ; and the remaining peaks at: 8.4, 10.3, 14.0, 14.8, 15.3, 15.6, 16.8, 18.1, 19.2, 20.5, 21.7, 22.2, 23.1, 24.9, 26.3, 26.7, and 29.1. A person skilled in the art would recognize that relative intensities of the XPRD peaks may significantly vary depending on the orientation of the sample under test and on the type and setting of the instrument used, so that the intensities in the XPRD traces included herein are to such extent illustrative and are not intended to be used for absolute comparisons. The peaks corresponding to X-ray powder diffraction pattern having a relative intensity greater than or equal to 10% are listed in Table 1.

TABLE 1

XRPD pattern peaks for Free Form A of the compound of formula (I).

| Peak No. | Position [°2θ] | Relative Intensity [%] |
|---|---|---|
| 1 | 7.37 | 100 |
| 2 | 7.79 | 87 |
| 3 | 8.38 | 19 |
| 4 | 10.27 | 14 |
| 5 | 12.67 | 13 |
| 6 | 13.96 | 16 |
| 7 | 14.75 | 17 |
| 8 | 15.25 | 13 |
| 9 | 15.63 | 13 |
| 10 | 16.82 | 19 |
| 11 | 18.05 | 13 |
| 12 | 19.23 | 23 |
| 13 | 20.51 | 15 |
| 14 | 21.68 | 27 |
| 15 | 22.23 | 11 |
| 16 | 23.05 | 11 |
| 17 | 24.03 | 78 |
| 18 | 24.90 | 13 |
| 19 | 25.14 | 10 |
| 20 | 26.29 | 12 |
| 21 | 26.73 | 16 |
| 22 | 29.11 | 10 |

FIG. 2 shows a DSC thermogram of Free Form A of the compound of formula (I) exhibiting a broad endotherm in the temperature range of 30-80° C. followed by relatively sharp endotherm with an onset transition at about 190.4° C. A person skilled in the art would recognize that the broad endotherm at below 80° C. is due to loss of water (dehydration) followed by the melting of the dehydrated Free Form A. Indeed, a TGA experiment (see FIG. 3) confirms an approximately 5% weight loss of the Free Form A at between room temperature and 50° C. A person skilled in the art would also recognize that the peak and onset temperatures of the endotherms may vary depending on the experimental conditions. Data in FIG. 2 were collected from a 6.4 mg sample of the solid in a T-zero hermetic aluminum pan that has been sealed, punctured with a single hole and equilibrated at about 25° C. for about 30 minutes. During the data collection period, the temperature was increased at a rate of about 10° C. per minute.

FIG. 3 is a TGA (thermal gravimetric analysis) thermogram of Free Form A of the compound of formula (I) exhibiting weight loss of approximately 5% between room temperature and 50° C. and a second weight loss at above 200° C. While the first weight loss (at below 50° C.) can be attributed to dehydration of the Free Form A, the second weight loss is likely to be due to decomposition of the compound.

FIG. 4 shows vapor sorption isotherm of Free Form A. The data shows that Free Form A can be converted to an anhydrous Free Form of the compound of Formula (I) by exposing the hydrated Free Form A to appropriate conditions. In one embodiment, the hydrated Free Form A may be converted to anhydrous Free Form B of the compound by equilibrating in a low humidity environment. FIG. 4 shows the interconversion between Free Forms A and B and that the hydration level of the Free form A can be varied. Thus, a dehydrated free Form B (obtainable from hydrated free Form A that has been equilibrated in a dry environment) would, upon exposure to air-moisture, absorb water from the air and hydrate until it absorbs about 6 weight % of water. Thus, the fully hydrated Free Form A may contain about 6 weight % water. Upon dehydrating hydrated Free Form A, a corresponding anhydrous Free Form B may be obtained. Without being bound to any particular theory, Applicants believe that the free acid of the compound of formula I can exist as a channel hydrate of which Free Form A (hydrated free form) and Free Form B (anhydrous free form) constitute two hydration levels possible for this compound. Whether the hydrated Free Form A could absorb additional water is not known at this time.

Thus, the present application also provides Free Form B of the compound of formula (I), which is characterized by an X-ray powder diffraction pattern (XPRD) comprising at least three approximate peak positions (degrees 2θ±0.2) when measured using Cu $K_\alpha$ radiation, selected from the group consisting of 7.5, 8.4, 13.9, 14.9, 15.9, and 23.5 when the XPRD is collected from about 5 to about 40 degrees 2θ. Solid Form B may also be characterized by an X-ray powder diffraction pattern, as measured using Cu $K_\alpha$ radiation, substantially similar to FIG. 5 and an endothermic peak having an onset temperature at about 190.1° C. as measured by differential scanning calorimetry in which the temperature is scanned at about 10° C. per minute.

FIG. 5 is an X-ray powder diffraction pattern of Free Form B of the compound of formula (I). The X-ray powder diffractogram of the compound of formula (I) was acquired using Bruker diffractometer with the sample loaded in a low-background Si holder at ambient temperature and humidity. The sample was illuminated with Cu $K\alpha_1$ radiation and XRPD data were collected from 3 to 40° 2θ. The XRPD result shows strong diffractions peaks (location in degree 2θ) at 7.5, 8.4, 13.9, 14.9, 15.9, and 23.5. A person skilled in the art would recognize that relative intensities of the XPRD peaks may significantly vary depending on the orientation of the sample under test and on the type and setting of the instrument used, so that the intensities in the XPRD traces included herein are to such extent illustrative and are not intended to be used for absolute comparisons. The peaks corresponding to X-ray powder diffraction pattern having a relative intensity greater than or equal to 10% are listed in Table 2.

TABLE 2

XRPD pattern peaks for Free Form B of the compound of formula (I).

| Peak No. | Position [°2θ] | Relative Intensity [%] |
| --- | --- | --- |
| 2 | 7.46 | 100 |
| 3 | 8.41 | 15 |
| 8 | 13.89 | 12 |
| 9 | 14.92 | 15 |
| 10 | 15.88 | 12 |
| 20 | 23.50 | 28 |

FIG. 6 shows a DSC thermogram of Free Form B of the compound of formula (I) exhibiting a relatively sharp endotherm with an onset transition at about 190° C. A person skilled in the art would recognize that the sharp endotherm corresponds to melting of the dehydrated Free Form B. A person skilled in the art would also recognize that the peak and onset temperatures of the endotherms may vary depending on the experimental conditions. Data in FIG. 6 were collected from a 6.9 mg sample of the solid in a T-zero hermetic aluminum pan that has been sealed, punctured with a single hole and equilibrated at about 25° C. for about 30 minutes. During the data collection period, the temperature was increased at a rate of about 10° C. per minute.

FIG. 7 is a TGA (thermal gravimetric analysis) thermogram of Free Form B of the compound of formula (I) exhibiting weight loss at above 200° C.

The present application also provides Free Form C of the compound of formula (I), which is characterized by an X-ray powder diffraction pattern (XPRD) comprising at least three approximate peak positions (degrees 2θ±0.2) when measured using Cu $K_\alpha$ radiation, selected from the group consisting of 7.3, 9.2, 13.7, 14.4, and 18.4 when the XPRD is collected from about 5 to about 40 degrees 2θ. Solid Form C may also be characterized by an X-ray powder diffraction pattern, as measured using Cu $K_\alpha$ radiation, substantially similar to FIG. 8 and an endothermic peak having an onset temperature at about 214° C. as measured by differential scanning calorimetry in which the temperature is scanned at about 10° C. per minute.

In one embodiment, Free form C may be prepared from any free form of the compound of formula (I). In some embodiments, substantially pure Free Form C of the compound of formula (I) may be preparing by suspending a solid crystalline or amorphous material of the compound in a suitable solvent (slurry). Suitable solvents include mixtures of one or more organic solvents and water. For example, Free Form C may be prepared by equilibrating another free form in an appropriate solvent. Examples of solvents suitable for converting a Free form of the compound of formula (I) to Free Form C include medium polar solvents in which the compound of formula (I) is not substantially soluble. In one embodiment, a free form other than Free Form C may be suspended in the solvents. The suspension is then agitated/stirred for a period of time sufficient to convert the suspended free form to Free Form C. For example, suspending Free Form A in pentanol at 60° C. for a few hours to up to 1-10 days may convert the suspended solid form to Free Form C.

In certain embodiments, an amorphous sample of the compound may be converted to Free Form C by suspending the sample in an appropriate solvent. Examples of solvents suitable for converting an amorphous sample of the compound of formula (I) to Free Form C include medium polar solvents in which the compound of formula (I) is not substantially soluble. In one embodiment, an amorphous sample of the compound of formula (I) may be suspended in the solvents. The suspension is then agitated/stirred for a period of time sufficient to convert the suspended amorphous material to Free Form C. For example, suspending amorphous sample of the compound of formula (I) in pentanol at 60° C. for a few hours to up to 1-10 days may convert the suspended amorphous material to Free Form C.

Free Form C of the compound of formula (I) is a hydrated solid form which may be identified by one or more of the following characteristics: an X-ray powder diffraction pattern essentially as shown in Table 3 and FIG. 8 wherein the XRPD patterns were measured using a powder diffractometer equipped with a Cu X-ray tube source; and a melt endotherm with an extrapolated onset of about 214° C. as determined by differential scanning calorimetry using 10° C. per minute scan rate.

FIG. 8 is an X-ray powder diffraction pattern of Free Form C of the compound of formula (I). The X-ray powder diffractogram of the compound of formula (I) was acquired using Bruker diffractometer with the sample loaded in a low-background Si holder at ambient temperature and humidity. The sample was illuminated with Cu Kα₁ radiation and XRPD data were collected from 3 to 40° 2θ. The XRPD result shows strong diffractions peaks (location in degree 2θ) at 7.3, 9.2, 13.7, 14.4, and 18.4. A person skilled in the art would recognize that relative intensities of the XPRD peaks may significantly vary depending on the orientation of the sample under test and on the type and setting of the instrument used, so that the intensities in the XPRD traces included herein are to such extent illustrative and are not intended to be used for absolute comparisons. The peaks corresponding to X-ray powder diffraction pattern having a relative intensity greater than or equal to 8% are listed in Table 3.

TABLE 3

XRPD pattern peaks for Free Form C of the compound of formula (I).

| Peak No. | Position [°2θ] | Relative Intensity [%] |
|---|---|---|
| 1 | 7.30 | 100 |
| 2 | 9.24 | 26.79 |
| 3 | 13.70 | 15.03 |
| 4 | 14.39 | 8.07 |
| 5 | 18.35 | 9.17 |

FIG. 9 shows a DSC thermogram of Free Form C of the compound of formula (I) exhibiting a broad endotherm in the temperature range of 80-120° C. followed by relatively sharp endotherm with an onset transition at about 214° C. A person skilled in the art would recognize that the broad endotherm at below about 120° C. is due to loss of water (dehydration) followed by the melting of the dehydrated Free Form C. Indeed, a TGA experiment (see FIG. 10) confirms an approximately 1.7% weight loss of the Free Form C at between room temperature and 100° C. A person skilled in the art would also recognize that the peak and onset temperatures of the endotherms may vary depending on the experimental conditions. Data in FIG. 9 were collected from a 6.4 mg sample of the solid in a T-zero hermetic aluminum pan that has been sealed, punctured with a single hole and equilibrated at about 25° C. for about 30 minutes. During the data collection period, the temperature was increased at a rate of about 10° C. per minute.

FIG. 10 is a TGA (thermal gravimetric analysis) thermogram of Free Form C of the compound of formula (I) exhibiting weight loss of approximately 1.7% between room temperature and 100° C. and a second weight loss at above 210° C. While the first weight loss (at below 50° C.) can be attributed to dehydration of the Free Form C, the second weight loss is likely to be due to decomposition of the compound.

In another embodiment, the present application provides Sodium Salt Form X of the compound of formula (I), which is characterized by an X-ray powder diffraction pattern (XPRD) comprising at least three approximate peak positions (degrees 2θ±0.2) when measured using Cu Kα radiation, selected from the group consisting 6.3, 7.2, 10.7, 12.3, 12.7, 14.6, 16.9, 18.1, 18.8, 19.0, 19.7, 21.8, 24.3, 24.9, 27.3, and 28.1, when the XPRD is collected from about 5 to about 40 degrees 2θ. Salt Form X may also be characterized by an X-ray powder diffraction pattern, as measured using Cu Kα radiation, substantially similar to FIG. 11 and a differential scanning calorimetry trace characterized by the absence of an endotherm characteristic of melting temperature but containing a broad endotherm that may be characterized as a dehydration process.

FIG. 11 is an X-ray powder diffraction pattern of sodium salt Form X of the compound of formula (I). The X-ray powder diffractogram of the compound of formula (I) was acquired using a Bruker diffractometer with the sample loaded in a low-background Si holder at ambient temperature and humidity. The sample was illuminated with Cu Kα₁ radiation and XRPD data were collected from 3 to 40° 2θ. The XRPD result shows strong diffractions peaks (location in degree 2θ) at 7.2, 12.3, 12.7, 18.1, and 24.9 degree 2θ; and the remaining peaks at: 6.3, 10.7, 14.6, 16.9, 18.8, 19.0, 19.7, 21.8, 24.3, 27.3, and 28.1. A person skilled in the art would recognize that relative intensities of the XPRD peaks may significantly vary depending on the orientation of the sample under test and on the type and setting of the instrument used, so that the intensities in the XPRD traces included herein are to such extent illustrative and are not intended to be used for absolute comparisons. The peaks corresponding to X-ray powder diffraction pattern having a relative intensity greater than or equal to 9% are listed in Table 4.

TABLE 4

XRPD pattern peaks for sodium Salt Form X of the compound of formula (I).

| Peak No. | Position [°2θ] | Relative Intensity [%] |
|---|---|---|
| 1 | 6.29 | 13.29 |
| 2 | 7.17 | 100 |
| 3 | 10.66 | 30.2 |
| 4 | 12.26 | 34.19 |
| 5 | 12.74 | 27.21 |
| 6 | 14.55 | 11.14 |
| 7 | 16.91 | 12.7 |
| 9 | 18.05 | 15.51 |
| 10 | 18.76 | 11.32 |
| 11 | 19.03 | 9.4 |
| 12 | 19.69 | 12.6 |
| 14 | 21.83 | 9.52 |
| 15 | 24.30 | 11.06 |
| 16 | 24.85 | 29.07 |
| 17 | 27.27 | 11.19 |
| 18 | 28.06 | 9.94 |

FIG. 12 shows a DSC thermogram of sodium Salt Form X of the compound of formula (I) exhibiting a broad endotherm in the temperature range of about 30-100° C., which appears to be due loss of water, and a second broad endotherm at above 200° C., which could be due to decomposition. A person skilled in the art would also recognize that the peak and onset temperatures of the endotherms may vary depending on the experimental conditions. Data in FIG. 12 were collected from a 6.4 mg sample of the solid in a T-zero hermetic aluminum pan that has been sealed, punctured with a single hole and equilibrated at about 25° C. for about 30 minutes. During the data collection period, the temperature was increased at a rate of about 10° C. per minute.

In another embodiment, the present application provides an amorphous form of a di-sodium salt of the compound of formula (I), which is characterized by an X-ray powder diffraction pattern (XPRD), as measured using Cu Kα radiation, substantially similar to FIG. 13.

FIG. 14 shows a DSC thermogram of amorphous di-sodium salt of the compound of formula (I) exhibiting an endothermic peak having an onset temperature of about 82° C. as measured by differential scanning calorimetry in which the temperature is scanned at about 10° C. per minute. A person skilled in the art would also recognize that the peak and onset temperatures of the endotherms may vary depending on the experimental conditions. Data in FIG. 14 were collected from an approximately. 1-4 mg sample of the solid in a T-zero hermetic aluminum pan that has been sealed, punctured with a single hole and equilibrated at about 25° C. for about 30 minutes. During the data collection period, the temperature was increased at a rate of about 10° C. per minute to about 300° C.

XRPD's on the free Forms A, B and C and the di-sodium salt Form X and the di-sodium salt amorphous form were generated using a Bruker D8 Discover System. The XRPD patterns were acquired at room temperature in reflection mode using a Bruker D8 Discover diffractometer equipped with a sealed tube source and a Hi-Star area detector (Bruker AXS, Madison, Wis.). The X-Ray generator was operating at a voltage of 40 kV and a current of 35 mA. The powder sample was placed in a nickel holder. Two frames were registered with an exposure time of 120 s each. The data frames were subsequently integrated over the range of 4.5°-22.4° and 21°-39.0° 2 theta with a step size of 0.02° merged into one continuous pattern.

An XRPD on the amorphous di-sodium sat form was generated using the following procedure. The XRPD pattern of the amorphous solid form was recorded at room temperature in reflection mode using Bruker D8 Advance system equipped with Vantec-1 position sensitive detector (Bruker AXS, Madison, Wis.). The X-Ray generator was operating at a tension of 40 kV and a current of 45 mA. The powder sample was placed on a Si zero-background holder, spinning at 15 rpm during the experiment in a continuous mode using variable slit at the detector. Data was collected from 3 to 40 degrees with 0.0144653 degree increments (0.25 s/step)

All Differential Scanning Calroimetry (DSC) experiments were performed as follows. DSC was performed on a sample of the material using a DSC Q2000 or DSC Q200 differential scanning calorimeter (TA Instruments, New Castle, Del.). The instrument was calibrated with indium. A sample of approximately 1-2 mg was weighed into an aluminum pan that was crimped using lids with either no pin-hole or pin-hole lids. The DSC samples were scanned from 30° C. to temperatures indicated in the plots at a heating rate of 10° C./min with 50 mL/min nitrogen flow. The samples run under modulated DSC (MDSC) were modulated + and − 1° C. every 60 s with ramp rates of 2 or 3° C./min. Data were analyzed using TA Instruments Universal Analysis 2000 software V4.4A.

All Thermogravimetric Analyses were run according to the following method. A Model Q5000 Thermogravimetric Analyzer (TA Instruments, New Castle, Del.) was used for TGA measurement. A sample of with weight of approximately 3-5 mg was scanned from 30° C. to temperatures indicated on the plots at a heating rate of 10° C./min. Data was collected by Thermal Advantage Q Series™ software and analyzed by Universal Analysis 2000 software (TA Instruments, New Castle, Del.).

Unless otherwise stated, isotopically-labeled forms of compounds of formula (I) wherein one or more atoms are replaced by an atom having an atomic mass or mass number different from the atomic mass or mass number usually found in nature are also included herein. Examples of isotopes that can be incorporated into compounds of the invention include isotopes of hydrogen, carbon, nitrogen, oxygen, fluorine, and phosphorous such as $^2H$, $^3H$, $^{13}C$, $^{14}C$, $^{15}N$, $^{18}O$, $^{17}O$, $^{32}P$ and $^{33}P$. Such radio-labeled and stable-isotopically labeled compounds are useful, for example, as research or diagnostic tools or gyrase and/or topoisomerase IV inhibitors with improved therapeutic profile. The structures also encompass zwitterionic forms of the compounds, where appropriate.

The compounds of formula (I) are prodrugs of their parent compound, 1-ethyl-3-[6-fluoro-5-[2-(1-hydroxy-1-methylethyl)pyrimidin-5-yl]-7-[(2R)-tetrahydrofuran-2-yl]-1H-benzimidazol-2-yl]urea. Thus, the activity exhibited upon administration of the prodrug is principally due to the presence of the parent compound that results from cleavage of the prodrug.

The term "prodrug" refers to compounds which are drug precursors which, following administration and absorption, release the drug in vivo via some metabolic process. In general, a prodrug possesses less biological activity than its parent drug. A prodrug may also improve the physical properties of the parent drug and/or it may also improve overall drug efficacy, for example through the reduction of toxicity and unwanted effects of a drug by controlling its absorption, blood levels, metabolic distribution and cellular uptake.

The term "parent compound" or "parent drug" refers to the biologically active entity that is released via enzymatic action of a metabolic or a catabolic process, or via a chemical process following administration of the prodrug. The parent compound may also be the starting material for the preparation of its corresponding prodrug.

The prodrugs of the present invention are characterized by unexpectedly high aqueous solubility. This solubility facilitates administration of higher doses of the prodrug, resulting in a greater drug load per unit dosage.

One embodiment of this invention relates to a method of treating a bacterial infection in a mammal in need thereof, comprising administering to said mammal a therapeutically effective amount of a compound having the formula (I) or a pharmaceutically acceptable salt thereof.

According to another embodiment, the invention provides a method of decreasing or inhibiting bacterial quantity in a biological sample. This method comprises contacting said biological sample with a compound of formula (I) or a pharmaceutically acceptable salt thereof.

The term "biological sample", as used herein, includes cell cultures or extracts thereof biopsied material obtained from a mammal or extracts thereof and blood, saliva, urine, feces, semen, tears, or other body fluids or extracts thereof. The term "biological sample" also includes living organisms, in which case "contacting a compound of this invention with a biological sample" is synonymous with the term "administering said compound or composition comprising said compound) to a mammal".

One embodiment comprises contacting said biological sample with the compound of Formula (I). Pharmaceutical compositions useful for such methods are described below. The antimicrobial activity of the compounds of formula (I) may be demonstrated in an antimicrobial susceptibility assay. The details of the conditions used for the antimicrobial susceptibility assays are set forth in the Examples below.

The gyrase and/or topoisomerase IV inhibitors of this invention, or pharmaceutical salts thereof, may be formulated into pharmaceutical compositions for administration to animals or humans. These pharmaceutical compositions effective to treat or prevent a bacterial infection which comprise the gyrase and/or topoisomerase IV inhibitor in an amount sufficient to measurably decrease bacterial quantity and a pharmaceutically acceptable carrier, are another embodiment of the present invention. The term "measurably decrease bacterial quantity", as used herein means a measurable change in the number of bacteria between a sample containing said inhibitor and a sample containing only bacteria.

Agents which increase the susceptibility of bacterial organisms to antibiotics are known. For example, U.S. Pat. No. 5,523,288, U.S. Pat. No. 5,783,561 and U.S. Pat. No. 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in Microbiological Reviews (1992) pp. 395-411, and the sensitization of gram-negative bacteria has been described by Tsubery, H., et al, in J. Med. Chem. (2000) pp. 3085-3092.

Another embodiment of this invention relates to a method, as described above, of preventing, controlling, treating or reducing the advancement, severity or effects of a bacterial infection in a mammal in need thereof, but further comprising the step of administering to said mammal an agent which increases the susceptibility of bacterial organisms to antibiotics.

According to another embodiment, the methods of the present invention are useful to treat patients in the veterinarian field including, but not limited to, zoo, laboratory, human companion, and farm animals including primates, rodents, reptiles and birds. Examples of said animals include, but are not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, ostriches, chickens, turkeys, ducks, and geese.

The pharmaceutical compositions and methods of this invention will be useful generally for controlling bacterial infections in vivo. Examples of bacterial organisms that may be controlled by the compositions and methods of this invention include, but are not limited to the following organisms: *Streptococcus pneumoniae, Streptococcus pyogenes, Enterococcus faecalis, Enterococcus faecium, Klebsiella pneumoniae, Enterobacter* spp. *Proteus* spp. *Pseudomonas aeruginosa, E. coli, Serratia marcescens, Staphylococcus aureus*, Coag. Neg. Staphylococci, *Haemophilus influenzae, Bacillus anthracis, Mycoplasma pneumoniae, Moraxella catarrhalis, Chlamydophila pneumoniae, Chlamydia trachomatis, Legionella pneumophila, Mycobacterium tuberculosis, Helicobacter pylori, Staphylococcus saprophyticus, Staphylococcus epidermidis, Francisella tularensis, Yersinia pestis, Clostridium difficile, Neisseria gonorrhoeae, Neisseria meningitidis, Mycobacterium avium* complex, *Mycobacterium abscessus, Mycobacterium kansasii* and *Mycobacterium ulcerans*.

The compositions and methods will therefore be useful for controlling, treating or reducing the advancement, severity or effects of nosocomial or non-nosocomial infections. Examples of nosocomial and non-nosocomial infections include but are not limited to upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections. Examples of specific bacterial infections include but are not limited to uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial pneumoniae (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

The term "non-nosocomial infections" is also referred to as community acquired infections.

In one embodiment, the compositions and methods will therefore be useful for controlling, treating or reducing the advancement, severity or effects of community-acquired bacterial pneumoniae (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

In another embodiment, the compositions and methods will therefore be useful for controlling, treating or reducing the advancement, severity or effects of upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections, uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial pneumoniae (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

In another embodiment, the bacterial infection is characterized by the presence of one or more of *Streptococcus pneumoniae, Streptococcus pyogenes, Enterococcus faecalis, Enterococcus faecium, Staphylococcus aureus*, Coag. Neg. Staphlococci, *Bacillus anthracis, Staphylococcus epidermidis, Staphylococcus saprophyticus*, or *Mycobacterium tuberculosis*.

In another embodiment, the bacterial infection is characterized by the presence of one or more of *Streptococcus pneumoniae, Enterococcus faecalis*, or *Staphylococcus aureus*.

In another embodiment, the bacterial infection is characterized by the presence of one or more of *E. coli, Moraxella catarrhalis*, or *Haemophilus influenzae*.

In another embodiment, the bacterial infection is characterized by the presence of one or more of *Clostridium difficile, Neisseria gonorrhoeae, Neisseria meningitidis, Mycobacterium avium complex, Mycobacterium abscessus, Mycobacterium kansasii, Mycobacterium ulcerans, Chlamydophila pneumoniae* and *Chlamydia tracomatis*.

In another embodiment, the bacterial infection is characterized by the presence of one or more of *Streptococcus pneumoniae, Staphylococcus epidermidis, Enterococcus*

*faecalis, Staphylococcus aureus, Clostridium difficile, Moraxella catarrhalis, Neisseria gonorrhoeae, Neisseria meningitidis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci.

In some embodiments, the bacterial infection is characterized by the presence of one or more of Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant Coagulase negative *staphylococcus*, Fluoroquinolone resistant Coagulase negative *staphylococcus*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, Vancomycin resistant *staphylococcus epidermidis*, Fluoroquinolone resistant *Neisseria gonorrhoeae*, Multidrug Resistant *Pseudomonas aeruginosa* or Cephalosporin resistant *Neisseria gonorrhoeae*.

According to another embodiment, the Methicillin resistant Staphylococci are selected from Methicillin resistant *Staphylococcus aureus*, Methicillin resistant *Staphylococcus epidermidis*, or Methicillin resistant Coagulase negative *staphylococcus*.

In some embodiments, a form of a compound of formula (I) is used to treat community acquired MRSA (i.e., cMRSA).

In other embodiments, a form of a compound of formula (I) is used to treat daptomycin resistant organism including, but not limited to, daptomycin resistant *Enterococcus faecium* and daptomycin resistant *Staphylococcus aureus*.

According to another embodiment, the Fluoroquinolone resistant Staphylococci are selected from Fluoroquinolone resistant *Staphylococcus aureus*, Fluoroquinolone resistant *Staphylococcus epidermidis*, or Fluoroquinolone resistant Coagulase negative *staphylococcus*.

According to another embodiment, the Glycopeptide resistant Staphylococci are selected from Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, or Hetero vancomycin resistant *Staphylococcus aureus*.

According to another embodiment, the Macrolide-Lincosamide-Streptogramin resistant Staphylococci is Macrolide-Lincosamide-Streptogramin resistant *Staphylococcus aureus*.

According to another embodiment, the Linezolid resistant Enterococci are selected from Linezolid resistant *Enterococcus faecalis*, or Linezolid resistant *Enterococcus faecium*.

According to another embodiment, the Glycopeptide resistant Enterococci are selected from Vancomycin resistant *Enterococcus faecium* or Vancomycin resistant *Enterococcus faecalis*.

According to another embodiment, the β-lactam resistant *Enterococcus faecalis* is β-lactam resistant *Enterococcus faecium*.

According to another embodiment, the Penicillin resistant Streptococci is Penicillin resistant *Streptococcus pneumoniae*.

According to another embodiment, the Macrolide resistant Streptococci is Macrolide resistant *Streptococcus pneumonia*.

According to another embodiment, the Ketolide resistant Streptococci are selected from Macrolide resistant *Streptococcus pneumoniae* and Ketolide resistant *Streptococcus pyogenes*.

According to another embodiment, the Fluoroquinolone resistant Streptococci is Fluoroquinolone resistant *Streptococcus pneumoniae*.

According to another embodiment, the β-lactam resistant Haemophilus is β-lactam resistant *Haemophilus influenzae*.

According to another embodiment, the Fluoroquinolone resistant Haemophilus is Fluoroquinolone resistant *Haemophilus influenzae*.

According to another embodiment, the Macrolide resistant Haemophilus is Macrolide resistant *Haemophilus influenzae*.

According to another embodiment, the Macrolide resistant Mycoplasma is Macrolide resistant *Mycoplasma pneumoniae*.

According to another embodiment, the Isoniazid resistant Mycobacterium is Isoniazid resistant *Mycobacterium tuberculosis*.

According to another embodiment, the Rifampin resistant Mycobacterium is Rifampin resistant *Mycobacterium tuberculosis*.

According to another embodiment, the β-lactam resistant Moraxella is β-lactam resistant *Moraxella catarrhalis*.

According to another embodiment, the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacte-*

*rium tuberculosis*, Fluoroquinolone resistant *Neisseria gonorrhoeae* or Cephalosporin resistant *Neisseria gonorrhoeae*.

According to another embodiment, the bacterial infection is characterized by the presence of one or more of the following: Methicillin resistant *Staphylococcus aureus*, Methicillin resistant *Staphylococcus epidermidis*, Methicillin resistant Coagulase negative *staphylococcus*, Fluoroquinolone resistant *Staphylococcus aureus*, Fluoroquinolone resistant *Staphylococcus epidermidis*, Fluoroquinolone resistant Coagulase negative *staphylococcus*, Vancomycin resistant *Staphylococcus aureus*, Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Vancomycin resistant *Enterococcus faecium*, Vancomycin resistant *Enterococcus faecalis*, Penicillin resistant *Streptococcus pneumoniae*, Macrolide resistant *Streptococcus pneumoniae*, Fluoroquinolone resistant *Streptococcus pneumoniae*, Macrolide resistant *Streptococcus pyogenes*, or β-lactam resistant *Haemophilus influenzae*.

According to another embodiment, the bacterial infection is characterized by the presence of one or more of the following: Methicillin resistant *Staphylococcus aureus*, Vancomycin resistant *Enterococcus faecium*, Vancomycin resistant *Enterococcus faecalis*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Multidrug Resistant *Pseudomonas aeruginosa*, Isoniazid resistant *Mycobacterium tuberculosis*, and Rifampin resistant *Mycobacterium tuberculosis*.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

Pharmaceutical compositions of this invention comprise a compound of formula (I) or a pharmaceutically acceptable salt thereof and a pharmaceutically acceptable carrier. Such compositions may optionally comprise an additional therapeutic agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as alpha-tocopherol, polyethyleneglycol 1000 succinate, or other similar polymeric delivery matrices.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

Depending upon the particular condition, or disease state, to be treated or prevented, additional therapeutic agents, which are normally administered to treat or prevent that condition, may be administered together with the inhibitors of this invention. Such therapeutic agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. In one embodiment, the compounds of this invention may be used in compositions and methods for treating or protecting individuals against bacterial infections or diseases over a 1-2 week period. In another embodiment, the compounds of this invention may be used in compositions and methods for treating or protecting individuals against bacterial infections or diseases over a 4-8 week period (for example, in the treatment of patients with or at risk for developing endocarditis or osteomyelitis). In another embodiment, the compounds of this invention may be used in compositions and methods for treating or protecting individuals against bacterial infections or diseases over an 8-12 week period. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

In some embodiments, compounds of formula (I) may be used prophylactically to prevent a bacterial infection. In some embodiments, compounds of formula (I) may be used before, during or after a dental or surgical procedure to prevent opportunistic infections such as those encountered in bacterial endocarditis. In other embodiments, compounds of formula (I) may be used prophylactically in dental procedures, including but not limited to extractions, periodontal procedures, dental implant placements and endodontic surgery. In other embodiments, compounds of formula (I) may be used prophylactically in surgical procedures including but not limited to general surgery, respiratory surgery (tonsillectomy/adenoidectomy), gastrointestinal surgery (upper GI and elective small bowel surgery, esophageal sclerotherapy and dilation, large bowel resections, acute appendectomy), trauma surgery (penetrating abdominal surgery), genito-urinary tract surgery (prostatectomy, urethral dilation, cystoscopy, vaginal or abdominal hysterectomy, cesarean section), transplant surgery (kidney, liver, pancreas or kidney transplantation), head and neck surgery (skin excisions, neck dissections, laryngectomy, head and neck cancer surgeries, mandibular fractures), orthopaedic surgery (total joint replacement, traumatic open fractures), vascular surgery (peripheral vascular procedures), cardiothoracic surgery, coronary bypass surgery, pulmonary resection and neurosurgery.

The term "prevent a bacterial infection" as used herein, unless otherwise indicated, means the prophylactic use of an antibiotic, such as a gyrase and/or topoisomerase IV inhibitor of the present invention, to prevent a bacterial infection. Treatment with a gyrase and/or topoisomerase IV inhibitor could be done prophylactically to prevent an infection caused by an organism that is susceptible to the gyrase and/or topoisomerase IV inhibitor. One general set of conditions where prophylactic treatment could be considered is when an individual is more vulnerable to infection due to, for example, weakened immunity, surgery, trauma, presence of an artificial device in the body (temporary or permanent), an anatomical defect, exposure to high levels of bacteria or possible exposure to a disease-causing pathogen. Examples of factors that could lead to weakened immunity include chemotherapy, radiation therapy, diabetes, advanced age, HIV infection, and transplantation. An example of an anatomical defect would be a defect in the heart valve that increases the risk of bacterial endocarditis. Examples of artificial devices include artificial joints, surgical pins, catheters, etc. Another set of situations where prophylactic use of a gyrase and/or topoisomerase IV inhibitor might be appropriate would be to prevent the spread of a pathogen between individuals (direct or indirect). A specific example of prophylactic use to prevent the spread of a pathogen is the use of a gyrase and/or topoisomerase IV inhibitor by individuals in a healthcare institution (for example a hospital or nursing home).

The compounds of formula (I) may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula (I) and another therapeutic or prophylactic agent.

In some embodiments, the additional therapeutic agent or agents is an antibiotic selected from a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide.

In some embodiments, the additional therapeutic agent or agents is an antibiotic selected from a penicillin, a cephalosporin, a quinolone, an aminoglycoside or an oxazolidinone.

In other embodiments, the additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, Ceftaroline and Ceftobiprole, from a Cephamycin including Cefotetan and Cefoxitin, from a carbapenem including Doripenem, Imipenem and Meropenem, from a monobactam including Aztreonam, from a quinolone including Cinoxacin, Nalidixic acid, Oxolininc acid and Pipemidic acid, from a fluoroquinolone including Besifloxacin, Ciprofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Dalbavancin, Telavancin, Teicoplanin and Vancomycin, from a streptogramin including Dalfopristin/quinupristin, from an oxazolidone including Linezolid, from a Rifamycin including Rifabutin and Rifampin and from other antibiotics including bactitracin, colistin, Tygacil, Daptomycin, chloramphenicol, clindamycin, isoniazid, metronidazole, mupirocin, polymyxin B, pyrazinamide, trimethoprim/sulfamethoxazole and sulfisoxazole.

In other embodiments, the additional therapeutic agents are selected from a natural penicillin including Penicillin G, from a penicillinase-resistant penicillin including Nafcillin and Oxacillin, from an antipseudomonal penicillin including Pipercillin/tazobactam, from an aminopenicillin including Amoxicillin, from a first generation cephalosporin including Cephalexin, from a second generation cephalosporin including Cefaclor, Cefaclor-CD and Cefuroxime, from a third generation cephalosporin including Ceftazidime and Ceftriaxone, from a fourth generation cephalosporin including Cefepime, from a carbapenem including Imepenem, Meropenem, Ertapenem, Doripenem, Panipenem and Biapenem, a fluoroquinolone including Ciprofloxacin, Gatifloxacin, Levofloxacin and Moxifloxacin, from an aminoglycoside including Tobramycin, from a macrolide including Azithromycin and Clarithromycin, from a Tetracycline including Doxycycline, from a glycopeptide including Vancomycin, from a Rifamycin including Rifampin and from other antibiotics including isoniazid, pyrazinamide, Tygacil, Daptomycin or trimethoprim/sulfamethoxazole.

In some embodiments, a solid form of a compound of formula (I), can be administered for the treatment of a gram positive infection. In some embodiments, the composition is a solid, liquid (e.g., a suspension), or an iv (e.g., a form of the formula (I) compound is dissolved into a liquid and administered iv) composition. In some embodiments, the composition including a formula (I) compound, is administered in combination with an additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide. In some embodiments, the composition including a solid form of a formula (I) compound is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide is administered iv.

In some embodiments, a solid form of a formula (I) compound, can be administered for the treatment of a gram negative infection. In some embodiments, the composition is a solid, liquid (e.g., a suspension), or an iv (e.g., a form of a formula (I) compound is dissolved into a liquid and administered iv) composition. In some embodiments the composition including a formula (I) compound is administered in combination with an additional antibiotic agent, selected from a: natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a polymyxin, tetracycline or a sulfonamide. In some embodiments, the composition including a solid form of a formula (I) compound is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a polymyxin, tetracycline or a sulfonamide is administered orally. In some embodiments, the additional therapeutic agent is administered iv.

The additional therapeutic agents described above may be administered separately, as part of a multiple dosage regimen, from the inhibitor-containing composition. Alternatively, these agents may be part of a single dosage form, mixed together with the inhibitor in a single composition.

The pharmaceutical compositions of this invention may be administered orally, parenterally, by inhalation spray, topically, rectally, nasally, buccally, vaginally or via an implanted reservoir. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical, compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

According to another embodiment, compounds of formula (I) may also be delivered by implantation (e.g., surgically), such as with an implantable or indwelling device. An implantable or indwelling device may be designed to reside either permanently or temporarily in a subject. Examples of implantable and indwelling devices include, but are not limited to, contact lenses, central venous catheters and needleless connectors, endotracheal tubes, intrauterine devices, mechanical heart valves, pacemakers, peritoneal dialysis catheters, prosthetic joints, such as hip and knee replacements, tympanostomy tubes, urinary catheters, voice prostheses, stents, delivery pumps, vascular filters and implantable control release compositions. Biofilms can be detrimental to the health of patients with an implantable or indwelling medical device because they introduce an artificial substratum into the body and can cause persistent infections. Thus, providing compounds of formula (I) in or on the implantable or indwelling device can prevent or reduce the production of a biofilm. In addition, implantable or indwelling devices may be used as a depot or reservoir of compounds of formula (I). Any implantable or indwelling device can be used to deliver compounds of formula (I) provided that a) the device, compounds of formula (I) and any pharmaceutical composition including compounds of formula (I) are biocompatible, and b) that the device can deliver or release an effective amount of compounds of formula (I) to confer a therapeutic effect on the treated patient.

Delivery of therapeutic agents via implantable or indwelling devices is known in the art. See for example, "Recent Developments in Coated Stents" by Hofma et al. published in *Current Interventional Cardiology Reports* 2001, 3:28-36, the entire contents of which, including references cited therein, incorporated herein by reference. Other descriptions of implantable devices can be found in U.S. Pat. Nos. 6,569, 195 and 6,322,847; and U.S. Patent Application Numbers 2004/0044405, 2004/0018228, 2003/0229390, 2003/0225450, 2003/0216699 and 2003/0204168, each of which is incorporated herein by reference in its entirety.

In some embodiments, the implantable device is a stent. In one specific embodiment, a stent can include interlocked meshed cables. Each cable can include metal wires for structural support and polymeric wires for delivering the therapeutic agent. The polymeric wire can be dosed by immersing the polymer in a solution of the therapeutic agent. Alternatively, the therapeutic agent can be embedded in the polymeric wire during the formation of the wire from polymeric precursor solutions.

In other embodiments, implantable or indwelling devices can be coated with polymeric coatings that include the therapeutic agent. The polymeric coating can be designed to control the release rate of the therapeutic agent. Controlled release of therapeutic agents can utilize various technologies. Devices are known that have a monolithic layer or coating incorporating a heterogeneous solution and/or dispersion of an active agent in a polymeric substance, where the diffusion of the agent is rate limiting, as the agent diffuses through the polymer to the polymer-fluid interface and is released into the surrounding fluid. In some devices, a soluble substance is also dissolved or dispersed in the polymeric material, such that additional pores or channels are left after the material dissolves. A matrix device is generally diffusion limited as well, but with the channels or other internal geometry of the device also playing a role in releasing the agent to the fluid. The channels can be pre-existing channels or channels left behind by released agent or other soluble substances.

Erodible or degradable devices typically have the active agent physically immobilized in the polymer. The active agent can be dissolved and/or dispersed throughout the polymeric material. The polymeric material is often hydrolytically degraded over time through hydrolysis of labile bonds, allowing the polymer to erode into the fluid, releasing the active agent into the fluid. Hydrophilic polymers have a generally faster rate of erosion relative to hydrophobic polymers. Hydrophobic polymers are believed to have almost purely surface diffusion of active agent, having erosion from the surface inwards. Hydrophilic polymers are believed to allow water to penetrate the surface of the polymer, allowing hydrolysis of labile bonds beneath the surface, which can lead to homogeneous or bulk erosion of polymer.

The implantable or indwelling device coating can include a blend of polymers each having a different release rate of the therapeutic agent. For instance, the coating can include a polylactic acid/polyethylene oxide (PLA-PEO) copolymer and a polylactic acid/polycaprolactone (PLA-PCL) copolymer. The polylactic acid/polyethylene oxide (PLA-PEO) copolymer can exhibit a higher release rate of therapeutic agent relative to the polylactic acid/polycaprolactone (PLA-PCL) copolymer. The relative amounts and dosage rates of therapeutic agent delivered over time can be controlled by controlling the relative amounts of the faster releasing polymers relative to the slower releasing polymers. For higher initial release rates the proportion of faster releasing polymer can be increased relative to the slower releasing polymer. If most of the dosage is desired to be released over a long time period, most of the polymer can be the slower releasing polymer. The device can be coated by spraying the device with a solution or dispersion of polymer, active agent, and solvent. The solvent can be evaporated, leaving a coating of polymer and active agent. The active agent can be dissolved and/or dispersed in the polymer. In some embodiments, the co-polymers can be extruded over the device.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections.

Typically, the pharmaceutical compositions of this invention will be administered from about 1 to 5 times per day or alternatively, as a continuous infusion. Alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula (I) and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

According to another embodiment, the invention provides methods for treating or preventing a bacterial infection, or disease state, comprising the step of administering to a patient any compound, pharmaceutical composition, or combination described herein. The term "patient", as used herein, means an animal, preferably a mammal, and most preferably a human.

The compounds of this invention are also useful as commercial reagents which effectively bind to the gyrase B and/or topoisomerase IV enzymes. As commercial reagents, the compounds of this invention, and their derivatives, may be used to block gyrase B and/or topoisomerase IV activity in biochemical or cellular assays for bacterial gyrase B and/or topoisomerase IV or their homologs or may be derivatized to bind to a stable resin as a tethered substrate for affinity chromatography applications. These and other uses which characterize commercial gyrase B and/or topoisomerase IV inhibitors will be evident to those of ordinary skill in the art.

The compounds of this invention may be prepared in accordance with general methods known to those skilled in the art for analogous compounds, as taught by U.S. Pat. No. RE40245 E; U.S. Pat. No. 7,495,014 B2; U.S. Pat. No. 7,569,591 B2; U.S. Pat. No. 7,582,641 B2; U.S. Pat. No. 7,618,974 B2; and U.S. Pat. No. 7,727,992 B2. All six of said patents are incorporated by reference as if fully set forth herein. The details of the conditions used for preparing the compounds of the present invention are further set forth in the Examples.

In order that this invention be more fully understood, the following examples are set forth. These examples are for the purpose of illustration only and are not to be construed as limiting the scope of the invention in any way.

The following definitions describe terms and abbreviations used herein:
Ac acetyl
Bu butyl
Et ethyl
Ph phenyl
Me methyl
THF tetrahydrofuran
DCM dichloromethane
$CH_2Cl_2$ dichloromethane
EtOAc ethyl acetate
$CH_3CN$ acetonitrile
EtOH ethanol
$Et_2O$ diethyl ether
MeOH methanol
MTBE methyl tert-butyl ether
DMF N,N-dimethylformamide
DMA N,N-dimethylacetamide
DMSO dimethyl sulfoxide
HOAc acetic acid
TEA triethylamine
TFA trifluoroacetic acid
TFAA trifluoroacetic anhydride
$Et_3N$ triethylamine
DIPEA diisopropylethylamine
DIEA diisopropylethylamine
$K_2CO_3$ potassium carbonate
$Na_2CO_3$ sodium carbonate
$Na_2S_2O_3$ sodium thiosulfate
$Cs_2CO_3$ cesium carbonate
$NaHCO_3$ sodium bicarbonate
NaOH sodium hydroxide
$Na_2SO_4$ sodium sulfate
$MgSO_4$, magnesium sulfate
$K_3PO_4$ potassium phosphate
$NH_4Cl$ ammonium chloride
LC/MS liquid chromatography/mass spectra
GCMS gas chromatography mass spectra
HPLC high performance liquid chromatography
GC gas chromatography
LC liquid chromatography
IC ion chromatography
IM intramuscular
CFU/cfu colony forming units
MIC minimum inhibitory concentration
Hr or h hours
atm atmospheres
rt or RT room temperature
TLC thin layer chromatography
HCl hydrochloric acid
$H_2O$ water EtNCO ethyl isocyanate
Pd/C palladium on carbon
NaOAc sodium acetate
$H_2SO_4$ sulfuric acid
$N_2$ nitrogen gas
$H_2$ hydrogen gas
n-BuLi n-butyl lithium
DI de-ionized
$Pd(OAc)_2$ palladium(II)acetate
$PPh_3$ triphenylphosphine
i-PrOH isopropyl alcohol
NBS N-bromosuccinimide
$Pd[(Ph_3)P]_4$ tetrakis(triphenylphosphine)palladium(0)
PTFE polytetrafluoroethylene
rpm revolutions per minute
SM starting material
Equiv. equivalents
$^1$H-NMR proton nuclear magnetic resonance
HPMCAS hydroxypropylmethylcellulose acetate
PVP polyvinylpyrrolidone
EDTA ethylenediaminetetraacetic acid
K2EDTA dibasic potassium ethylenediaminetetraacetate
mCPBA meta-chloroperoxybenzoic acid
aq aqueous
$Boc_2O$ di-tert-butyl dicarbonate
DMAP N,N-dimethylaminopyridine
mL milliliters
L liters
mol moles
g grams
LCMS liquid chromatography-mass spectrometry
MHz megahertz
$CDCl_3$ deuterochloroform
$NEt_3$ triethylamine
mmol millimoles
psi pounds per square inch
iPrOH isopropylalcohol
ppm parts per million
$NH_4NO_3$ ammonium nitrate
Hz hertz
$Pd(dppf)Cl_2$ [1,1'-Bis(diphenylphosphino)ferrocene]dichloropalladium(II)
L liters
MeOD deutero-methanol
$CD_3OD$ deutero-methanol
ee enantiomeric excess
min minutes
Bn benzyl
RBF round-bottom flask
MeCN acetonitrile
PES polyethersulfone
mm millimeters
μm micrometers
M molar
N normal
Boc tert-butoxycarbonyl
ESMS electrospray mass spectrometry
CV column volume
$D_2O$ deuterium oxide
$NH_3$ ammonia
OBD optimum bed density
mg milligrams
CLSI Clinical and Laboratory Standards Institute
ATCC American Type Culture Collection
MHII Mueller Hinton II
μL microliters
WT wild type
CGSC Coli Genetic Stock Center
MS mass spectrometry
IS internal standard
APCI atmospheric pressure chemical ionization
MRM multiple reaction monitoring
m/z mass-to-charge ratio
LLOQ lower limit of quantitation
ng nanograms
UV ultraviolet
SD standard deviation
% CV coefficient of variation
PO perioral
MC microcrystalline cellulose
EDTA ethylenediaminetetraacetic acid or ethylenediaminetetraacetate
PK pharmacokinetic
IV intravenous
D5W 5% dextrose in water solution
HPMC-AS hydroxypropyl methylcellulose acetyl succinate
PVP polyvinylprrolidone
CAPT captisol
ATP adenosine triphosphate
ADP adenosine diphosphate
NADH nicotinamide adenine dinucleotide (reduced form)
NAD+ nicotinamide adenine dinucleotide (oxidized form)
TRIS tris(hydroxymethyl)aminomethane
mM millimolar
$MgCl_2$ magnesium chloride
KCl potassium chloride
μM micromolar
DTT dithiothreitol
nM nanomolar
$K_i$ dissociation constant
$IC_{50}$ half maximal inhibitory concentration
micrograms
BSA bovine serum albumin
LDH lactate dehydrogenase
PVDF polyvinylidene fluoride
PBS phosphate buffered saline
BSL3 Biosafety Level 3
AcN acetonitrile
$V_{MAX}$ the maximum initial velocity or rate of a reaction The compounds of Formula (I) may be prepared readily using the following methods.

Synthesis of the Compound of Formula (I)

General Methods.
$^1$H NMR (400 MHz) and $^{13}$C NMR (100 MHz) spectra were obtained as solutions in deuterioacetonitrile ($CD_3CN$), chloroform-d ($CDCl_3$) or dimethyl sulfoxide-$D_6$ (DMSO). Mass spectra (MS) were obtained using an Applied Biosystems API EX LC/MS system equipped with a Phenomenex 50×4.60 mm luna-5μ C18 column. The LC/MS eluting system was 1-99% or 10-99% acetonitrile in $H_2O$ with 0.035% v/v trifluoroacetic acid, 0.035% v/v formic acid, 5 mM HCl or 5 mM ammonium formate using a 3 or 15 minute linear gradient and a flow rate of 12 mL/minute. Silica gel chromatography was performed using silica gel-60 with a particle size of 230-400 mesh. Pyridine, dichloromethane ($CH_2Cl_2$), tetrahydrofuran (THF), dimethylformamide (DMF), acetonitrile (ACN), methanol (MeOH), and 1,4-dioxane were from Aldrich Sure-Seal bottles kept under dry nitrogen. All reactions were stirred magnetically unless otherwise noted.

Example 1

Preparation of 2-(2-fluoro-6-nitro-phenyl)-2,3-dihydrofuran (15A) and 2-(2-fluoro-6-nitro-phenyl)-2,5-dihydrofuran (15B)

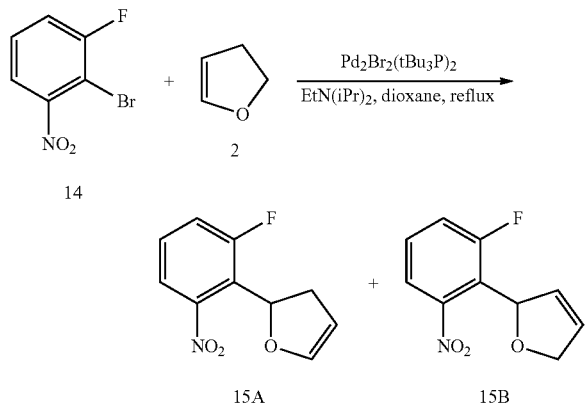

2-Bromo-1-fluoro-3-nitro-benzene (14) (200.3 g, 98%, 892.3 mmol, Bosche F6657), 1,4-dioxane (981.5 mL, Sigma-Aldrich 360481), and 2,3-dihydrofuran (2) (341.1 mL, 99%, 4.462 mol, Aldrich 200018) were charged in a reaction flask, followed by N,N-diisopropylethylamine (155.4 mL, 892.3 mmol, Sigma-Aldrich 550043) and bromo(tri-tert-butylphosphine)palladium(I) dimer (6.936 g, 8.923 mmol, Johnson Matthey C4099). The mixture was stirred at reflux for 2 hrs (HPLC showed 98% consumption of starting arylbromide). It was allowed to cool, the precipitate was removed by filtration, rinsed with EtOAc, and the filtrate concentrated in vacuo to a dark reddish brown semi-solid oil. This was dissolved in $CH_2Cl_2$, eluted through a plug of silica with $CH_2Cl_2$, and concentrated in vacuo giving a mixture of 15A and 15B as a dark amber oil (291.3 g). The crude product was carried forward without further purification. The major product was 2-(2-fluoro-6-nitro-phenyl)-2,3-dihydrofuran (15A) (96%): LCMS (C18 column eluting with 10-90% $CH_3CN$/water gradient over 5 minutes with formic acid modifier) M+1: 210.23 (3.13 min); $^1H$ NMR (300 MHz, $CDCl_3$) δ 7.54 (dt, J=8.0, 1.2 Hz, 1H), 7.43 (td, J=8.2, 5.2 Hz, 1H), 7.32 (ddd, J=9.7, 8.3, 1.3 Hz, 1H), 6.33 (dd, J=4.9, 2.4 Hz, 1H), 5.80 (t, J=10.9 Hz, 1H), 5.06 (q, J=2.4 Hz, 1H), 3.18-3.07 (m, 1H), 2.94-2.82 (m, 1H) ppm. The minor product was 2-(2-fluoro-6-nitro-phenyl)-2,5-dihydrofuran (15B) (4%): GCMS (Agilent HP-5MS 30 m×250 μm×0.25 μm column heating at 60° C. for 2 min to 300° C. over 15 min with a 1 mL/min flow rate) M+1: 210 (11.95 min) $^1H$ NMR (300 MHz, $CDCl_3$) δ 7.47 (d, J=8.0 Hz, 1H), 7.43-7.34 (m, 1H), 7.30-7.23 (m, 1H), 6.21-6.15 (m, 1H), 6.11-6.06 (m, 1H), 5.97-5.91 (m, 1H), 4.89-4.73 (m, 2H) ppm.

Example 2

Preparation of 3-fluoro-2-tetrahydrofuran-2-yl-aniline (16)

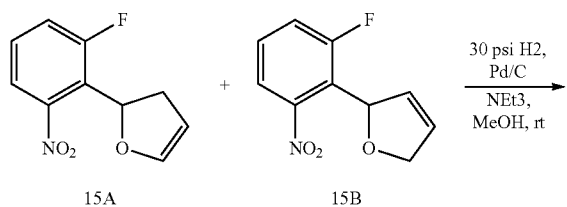

Placed 5% palladium on carbon (37.3 g, 50% wet, 8.76 mmol, Aldrich 330116) in a Parr bottle under nitrogen, followed by MeOH (70 mL, JT-Baker 909333). Added the crude mixture of 2-(2-fluoro-6-nitro-phenyl)-2,3-dihydrofuran and 2-(2-fluoro-6-nitro-phenyl)-2,5-dihydrofuran (15A&15B) (186.6 g, 892.1 mmol) dissolved in MeOH (117 mL), followed by $NEt_3$ (124.3 mL, 892.1 mmol, Sigma-Aldrich 471283). Placed the vessel on a Parr shaker and saturated with $H_2$. After adding 45 psi $H_2$, the reaction mixture was shaken until consumption of the starting material was complete (HPLC and LCMS showed complete reaction). The reaction mixture was purged with nitrogen, filtered through Celite™ and rinsed with EtOAc. The filtrate was concentrated on a rotary evaporator giving a brown oil, which was dissolved in $Et_2O$ and washed with water (2×). The ether phase was extracted with aqueous 1 N HCl (5×250 mL), which was washed with $Et_2O$ (3×) and then basified with aqueous 6 N NaOH to pH 12-14. The basic aqueous phase was extracted with $CH_2Cl_2$(4×), and the combined organic extract washed with saturated aqueous $NH_4Cl$, dried over $MgSO_4$, and filtered through a pad of silica eluting with $CH_2Cl_2$ to 25% EtOAc/hexane. The desired filtrate was concentrated under reduced pressure giving 16 as a light brown oil (121.8 g, 84% GCMS plus NMR purity). GCMS (Agilent HP-5MS 30 m×250 μm×0.25 μm column heating at 60° C. for 2 min to 300° C. over 15 min with a 1 mL/min flow rate) M+1: 182.0 (11.44 min). LCMS (C18 column eluting with 10-90% $CH_3CN$/water gradient over 5 minutes with formic acid modifier) M+1: 182.10 (2.61 min) $^1H$ NMR (300 MHz, $CDCl_3$) δ 6.97 (td, J=8.1, 6.3 Hz, 1H), 6.43-6.35 (m, 2H), 5.21-5.13 (m, 1H), 4.54 (s, 2H), 4.16-4.07 (m, 1H), 3.90-3.81 (m, 1H), 2.23-2.00 (m, 4H) ppm. Additional crops were obtained as follows: the combined ether phase was washed with saturated aqueous $NaHCO_3$, brine, dried over $Na_2SO_4$, decanted, and concentrated under reduced pressure. The oil was vacuum distilled (ca. 15 torr) collecting the distillate at 101-108° C. To a stirring solution of the distilled oil in EtOH (1 volume) at 2° C. was slowly added 5 M HCl (1 eq) in iPrOH. The resulting suspension was brought to room temperature, diluted with EtOAc (3 volumes, vol/vol), and stirred for 2 hrs. The white solid was collected by filtration, washed with EtOAc, and dried under reduced pressure giving a second crop of product as the HCl salt. The mother liquor was concentrated to a slurry, diluted with EtOAc and the solid collected by filtration, washed with EtOAc, and dried in vacuo giving the HCl salt as a third crop of the product. LCMS (C18 column eluting with 10-90% $CH_3CN$/water gradient over 5 minutes with formic acid modifier) M+1: 182.10 (2.58 min). $^1H$ NMR (300 MHz, $CDCl_3$) δ 10.73 (br.s, 3H), 7.66 (d, J=8.1 Hz, 1H), 7.33 (td, J=8.2, 5.9 Hz, 1H), 7.13-7.05 (m, 1H), 5.26 (dd, J=9.0, 6.5 Hz, 1H), 4.38-4.28 (m, 1H), 4.00-

3.91 (m, 1H), 2.59-2.46 (m, 1H), 2.30-1.95 (m, 3H) ppm. The overall yield from the three crops was 76%.

Example 3

Preparation of 4-bromo-3-fluoro-2-tetrahydrofuran-2-yl-aniline (17)

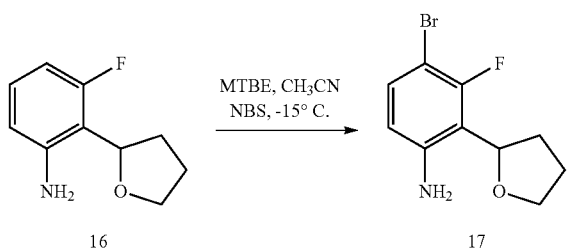 [SMILES: Nc1cccc(F)c1C1CCCO1 ; Nc1ccc(Br)c(F)c1C1CCCO1]

To a stirring solution of 3-fluoro-2-tetrahydrofuran-2-yl-aniline (16) (131.9 g, 92%, 669.7 mmol) in methyl tert-butyl ether (1.456 L) and acetonitrile (485 mL) cooled to −20° C. was added N-bromosuccinimide (120.4 g, 99%, 669.7 mmol, Aldrich B81255) in 3 portions maintaining a reaction temperature below about −15° C. After complete addition stirring was continued at −15 to −10° C. for 30 minutes. $^1$H NMR of a worked-up aliquot showed 96% consumption of starting aniline so added another 4.82 g NBS and stirred at −10° C. for another 30 minutes. Aqueous 1 N $Na_2S_2O_3$ (670 mL) was added to the reaction mixture. The cold bath was removed, the mixture stirred for 20 minutes, then diluted with EtOAc. The layers were separated and the organic phase was washed with saturated aqueous $NaHCO_3$ (2×), water, brine, dried over $Na_2SO_4$, decanted, and concentrated under reduced pressure giving a dark amber oil. The residue was diluted with hexane and eluted through a short plug of silica eluting with 25% EtOAc/hexane to 50% EtOAc/hexane. The desired filtrate was concentrated in vacuo giving 17 as a dark amber oil (182.9 g, 90% yield; 86% NMR purity). LCMS (C18 column eluting with 10-90% $CH_3CN$/water gradient over 5 minutes with formic acid modifier) M+1: 260.12 (3.20 min). $^1$H NMR (300 MHz, $CDCl_3$) δ 7.15 (dd, J=8.6, 7.6 Hz, 1H), 6.30 (dd, J=8.7, 1.3 Hz, 1H), 5.19-5.12 (m, 1H), 4.58 (s, 2H), 4.16-4.07 (m, 1H), 3.90-3.81 (m, 1H), 2.23-1.99 (m, 4H) ppm.

Example 4

Preparation of N-(4-bromo-3-fluoro-6-nitro-2-tetrahydrofuran-2-yl-phenyl)-2,2,2-trifluoro-acetamide (18)

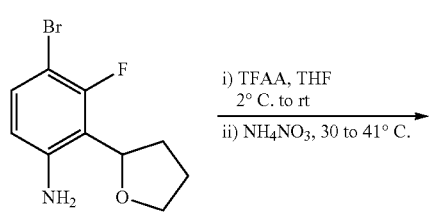

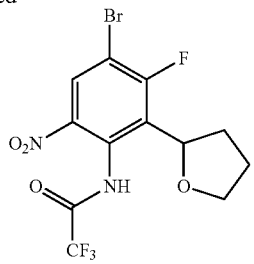

To trifluoroacetic anhydride (565.3 mL, 4.067 mol, Sigma-Aldrich 106232) stirring at 2° C. was slowly added neat 4-bromo-3-fluoro-2-tetrahydrofuran-2-yl-aniline (17) (123.0 g, 86%, 406.7 mmol) as a thick oil via addition funnel over about 20 minutes (reaction temperature rose to 13° C.). The remaining oil was rinsed into the reaction mixture with anhydrous THF (35 mL). The cold bath was removed and the reaction was heated to 35° C., followed by portion-wise addition of $NH_4NO_3$ (4.88 g×20 portions, 1.22 mol, Sigma-Aldrich A7455) over 2.5 hrs maintaining the reaction temperature between 30 and 41° C. using an ice-water bath only as needed to control the exotherm. After complete addition the reaction mixture was stirred for another 10 minutes (HPLC showed reaction 99% complete). It was slowly poured into crushed ice (1.23 kg) and stirred for 1 hr to allow formation of a filterable solid precipitate, which was collected and washed with water, sparingly with saturated aqueous $NaHCO_3$, and water again (to pH 7). The product was dried in a convection oven overnight at 40° C. and then under reduced pressure in an oven at 50° C. overnight giving 18 as a beige solid (152.0 g, 90% yield; 96% HPLC purity). LCMS (C18 column eluting with 10-90% $CH_3CN$/water gradient over 5 minutes with formic acid modifier) M+1: 401.30 (3.41 min) $^1$H NMR (300 MHz, $CDCl_3$) δ 10.56 (s, 1H), 8.19 (d, J=6.6 Hz, 1H), 5.22 (dd, J=10.3, 6.4 Hz, 1H), 4.22 (dd, J=15.8, 7.2 Hz, 1H), 3.99 (dd, J=16.1, 7.5 Hz, 1H), 2.50-2.38 (m, 1H), 2.22-2.11 (m, 2H), 1.86-1.71 (m, 1H) ppm.

Example 5

Preparation of 4-bromo-3-fluoro-6-nitro-2-tetrahydrofuran-2-yl-aniline (19)

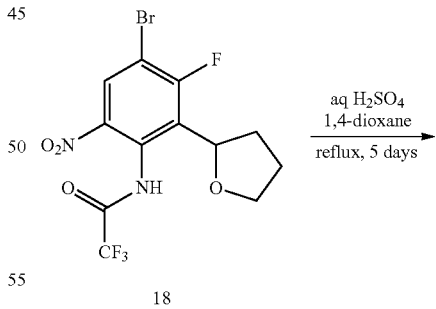

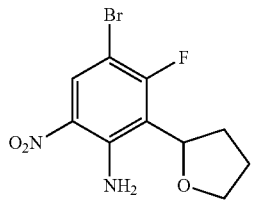

A reaction flask was charged with N-(4-bromo-3-fluoro-6-nitro-2-tetrahydrofuran-2-yl-phenyl)-2,2,2-trifluoro-acetamide (18) (242.3 g, 604.1 mmol), 1,4-dioxane (1.212 L), aqueous 2 M sulfuric acid (362.4 mL, 724.9 mmol), and stirred at reflux for 5 days (HPLC showed 98% conversion). Allowed to cool, diluted with EtOAc, neutralized with saturated aqueous NaHCO$_3$, separated the layers, and re-extracted the aqueous phase with EtOAc (2×). The combined organic phase was washed with brine (2×), dried over MgSO$_4$, filtered and concentrated in vacuo giving 19 as a greenish brown solid (181.7 g, 94% yield; 95% HPLC purity). The product was carried to the next step without further purification. LCMS (C18 column eluting with 10-90% CH$_3$CN/water gradient over 5 minutes with formic acid modifier) M+1: 305.20 (3.63 min). $^1$H NMR (300 MHz, CDCl$_3$) δ 8.35 (d, J=7.3 Hz, 1H), 7.45 (s, 2H), 5.23-5.16 (m, 1H), 4.23-4.14 (m, 1H), 3.93-3.84 (m, 1H), 2.31-1.96 (m, 4H) ppm.

Example 6

Preparation of 2-[5-(4-amino-2-fluoro-5-nitro-3-tetrahydrofuran-2-yl-phenyl)pyrimidin-2-yl]propan-2-ol (20)

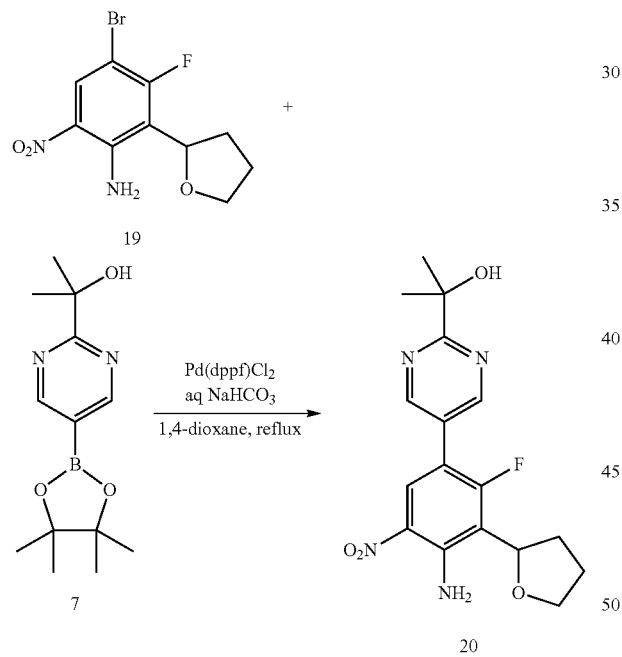

To a stirring solution of 4-bromo-3-fluoro-6-nitro-2-tetrahydrofuran-2-yl-aniline (19) (525.0 g, 1.721 mol, Bridge Organics Co.) in 1,4-dioxane (4.20 L, Sigma-Aldrich 360481) was added a 1.2 M aqueous solution of NaHCO$_3$ (4.302 L, 5.163 mol). A stream of nitrogen was bubbled through the stirring mixture for 2 hrs, followed by addition of 2-[5-(4,4,5,5-tetramethyl-1,3,2-dioxaborolan-2-yl)pyrimidin-2-yl]propan-2-ol (7) (545.4 g, 2.065 mol, Bridge Organics Co.) and 1,1'-bis(diphenylphosphino)ferrocene dichloropalladium dichloromethane adduct (42.16 g, 51.63 mmol, Strem 460450). The reaction mixture was stirred at reflux overnight, allowed to cool, diluted with EtOAc (8.4 L), and the layers were separated. The organic phase was washed with saturated aqueous NH$_4$Cl and then brine. The aqueous phase was re-extracted with EtOAc (4 L) and washed this organic extract with brine. The combined organic phase was dried over MgSO$_4$, filtered through a short plug of Florisil®, eluted with EtOAc, and the filtrate concentrated on a rotary evaporator giving a dark brown wet solid. This was dissolved in CH$_2$Cl$_2$, loaded on a pad of silica gel, eluted with hexane, then 25% EtOAc/hexane, and then 50% EtOAc/hexane. The desired filtrate was concentrated on a rotary evaporator to a thick suspension, and the solid was collected by filtration, triturated with MTBE, and dried in vacuo giving 20 as a bright yellow solid (55.8% yield, 90-97% HPLC purity). The filtrate was concentrated and the above purification was repeated giving a second crop of 20 as a bright yellow solid (19.7% yield). The filtrate was again concentrated giving a dark brown oil and this was loaded on a silica column with toluene and minimal CH$_2$Cl$_2$. It was eluted with EtOAc/hexane (0% to 50%). The desired fractions were concentrated to a slurry and diluted with MTBE/hexane. The solid was collected by filtration and washed with minimal MTBE giving a third crop of 20 as a bright yellow solid (4.9% yield) with an overall yield of 80% from the three crops. LCMS (C18 column eluting with 10-90% CH$_3$CN/water gradient over 5 minutes with formic acid modifier) M+1: 363.48 (2.95 min) $^1$H NMR (300 MHz, CDCl$_3$) δ 8.84 (d, J=1.6 Hz, 2H), 8.27 (d, J=8.0 Hz, 1H), 7.62 (s, 2H), 5.31-5.24 (m, 1H), 4.63 (s, 1H), 4.27-4.18 (m, 1H), 3.97-3.87 (m, 1H), 2.33-2.05 (m, 4H), 1.64 (s, 6H) ppm.

Example 7

Preparation of 2-[5-(4,5-diamino-2-fluoro-3-tetrahydrofuran-2-yl-phenyl)pyrimidin-2-yl]propan-2-ol (21)

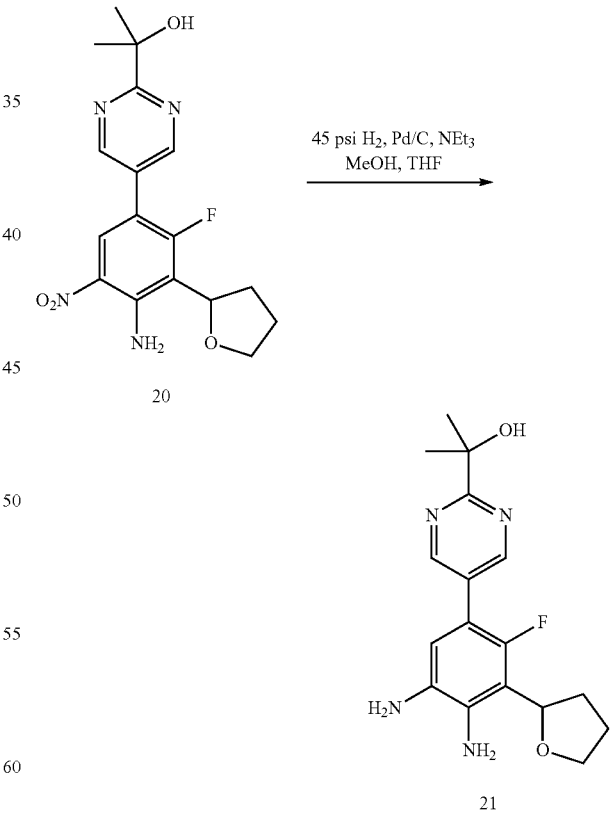

Placed 5% palladium on carbon (14.21 g, 50% wet, 3.339 mmol, Aldrich 330116) in a Parr bottle under nitrogen, followed by MeOH (242 mL, JT-Baker 909333) and NEt$_3$ (46.54 mL, 333.9 mmol, Sigma-Aldrich 471283). Dissolved 2-[5-

(4-amino-2-fluoro-5-nitro-3-tetrahydrofuran-2-yl-phenyl)pyrimidin-2-yl]propan-2-ol (20) (121.0 g, 333.9 mmol) in hot THF (360 mL), allowed to cool, added to the reaction mixture, and rinsed with another portion of THF (124 mL). Placed the vessel on a Parr shaker and saturated with H$_2$. Added 45 psi H$_2$ and shook until consumption was complete (HPLC and LCMS showed complete reaction). The reaction mixture was purged with nitrogen, filtered through Celite™ and rinsed with EtOAc. It was re-filtered through paper (glass microfibre) and the filtrate concentrated in vacuo. Repeated the reaction three more times on the same scale and the batches were combined giving 21 as a brown solid (447 g, 99% yield; 93% HPLC purity). LCMS (C18 column eluting with 10-90% CH$_3$CN/water gradient over 5 minutes with formic acid modifier) M+1: 333.46 (1.79 min) $^1$H NMR (300 MHz, CDCl$_3$) δ 8.81 (d, J=1.4 Hz, 2H), 6.69 (d, J=7.3 Hz, 1H), 5.27-5.20 (m, 1H), 4.73 (s, 1H), 4.70 (s, 2H), 4.23-4.14 (m, 1H), 3.94-3.86 (m, 1H), 3.22 (s, 2H), 2.32-2.22 (m, 1H), 2.18-1.99 (m, 3H), 1.63 (s, 6H) ppm.

Example 8

Preparation of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22)

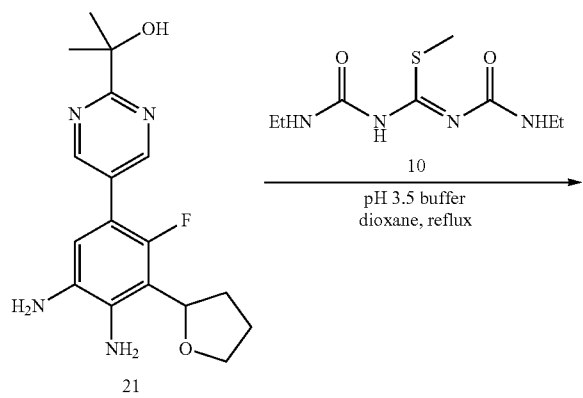

To a stirring suspension of 2-[5-(4,5-diamino-2-fluoro-3-tetrahydrofuran-2-yl-phenyl)pyrimidin-2-yl]propan-2-ol (21) (111.3 g, 334.9 mmol) and 1,4-dioxane (556.5 mL, Sigma-Aldrich 360481) was added 1-ethyl-3-(N-(ethylcarbamoyl)-C-methylsulfanyl-carbonimidoyl)urea (10) (93.36 g, 401.9 mmol, CB Research and Development) followed by a pH 3.5 buffer (1.113 L), prepared by dissolving NaOAc trihydrate (158.1 g) in 1N aqueous H$_2$SO$_4$ (1.100 L). The reaction mixture was stirred at reflux overnight (HPLC showed complete conversion), cooled to room temperature, and poured portion-wise (frothing) into a stirring solution of aqueous saturated NaHCO$_3$ (2.23 L) giving pH 8-9. This was stirred for 30 minutes, the solid was collected by filtration, washed copiously with water to neutral pH, and then more sparingly with EtOH. The solid was dried under reduced pressure giving 22 as an off-white yellowish solid (135.2 g, 94% yield; 99% HPLC purity). LCMS (C18 column eluting with 10-90% CH$_3$CN/water gradient over 5 minutes with formic acid modifier) M+1: 429.58 (2.03 min) $^1$H NMR (300 MHz, MeOD) δ 8.95 (d, J=1.6 Hz, 2H), 7.45 (d, J=6.5 Hz, 1H), 5.38 (br.s, 1H), 4.27 (dd, J=14.9, 7.1 Hz, 1H), 4.01 (dd, J=15.1, 7.0 Hz, 1H), 3.37-3.29 (m, 2H), 2.55 (br.s, 1H), 2.19-2.07 (m, 2H), 2.02-1.82 (br.s, 1H), 1.63 (s, 6H), 1.21 (t, J=7.2 Hz, 3H) ppm.

Example 9

Chiral chromatographic isolation of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23)

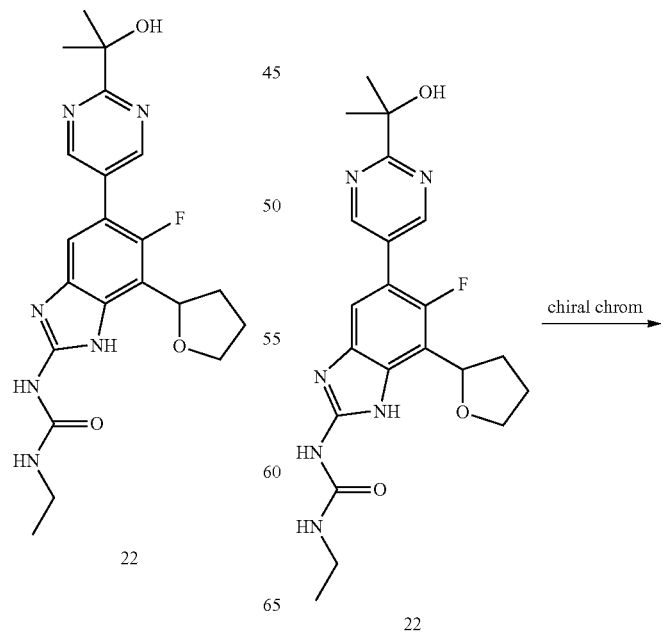

-continued

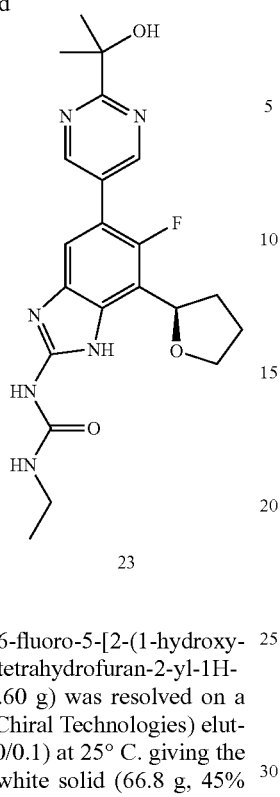

23

A racemic sample of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22) (133.60 g) was resolved on a CHIRALPAK® IC® column (by Chiral Technologies) eluting with DCM/MeOH/TEA (60/40/0.1) at 25° C. giving the desired enantiomer 23 as an off-white solid (66.8 g, 45% yield; 99.8% HPLC purity, 99+% ee). Analytical chiral HPLC retention time was 7.7 min (CHIRALPAK® IC® 4.6×250 mm column, 1 mL/min flow rate, 30° C.). The solid was suspended in 2:1 EtOH/Et$_2$O (5 volumes), stirred for 10 minutes, collected by filtration, washed with 2:1 EtOH/Et$_2$O, and dried under reduced pressure giving a white solid (60.6 g).

The structure and absolute stereochemistry of 23 were confirmed by single-crystal x-ray diffraction analysis. Single crystal diffraction data were acquired on a Bruker Apex II diffractometer equipped with sealed tube Cu K-alpha source (Cu Kα radiation, γ=1.54178 Å) and an Apex II CCD detector. A crystal with dimensions of 0.15×0.15×0.10 mm was selected, cleaned using mineral oil, mounted on a Micro-Mount and centered on a Bruker APEXII system. Three batches of 40 frames separated in reciprocal space were obtained to provide an orientation matrix and initial cell parameters. Final cell parameters were obtained and refined after data collection was completed based on the full data set. Based on systematic absences and intensities statistics the structure was solved and refined in acentric P2$_1$ space group.

A diffraction data set of reciprocal space was obtained to a resolution of 0.85 Å using 0.5° steps using 30 s exposures for each frame. Data were collected at 100 (2) K. Integration of intensities and refinement of cell parameters were accomplished using APEXII software. Observation of the crystal after data collection showed no signs of decomposition. As shown in FIG. 2, there are two symmetry independent molecules in the structure and both symmetry independent molecules are R isomers.

The data were collected, refined and reduced using the Apex II software. The structure was solved using the SHELXS97 (Sheldrick, 1990); program(s) and the structure refined using the SHELXL97 (Sheldrick, 1997) program. The crystal shows monoclinic cell with P2$_1$ space group. The lattice parameters are a=9.9016(2) Å, b=10.9184(2) Å, c=19.2975(4) Å, β=102.826(1)°. Volume=2034.19(7) Å$^3$.

Example 10

Preparation of the methanesulfonic acid salt of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23A)

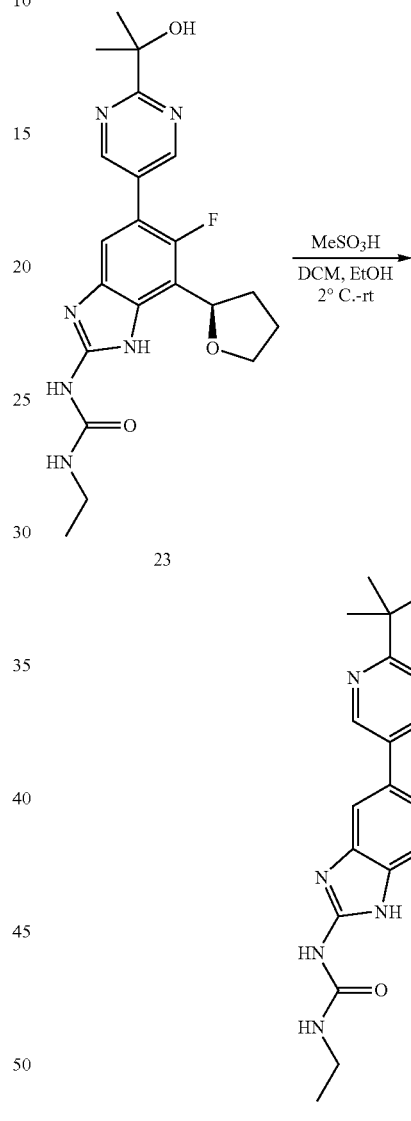

To a stirring suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (15.05 g, 35.13 mmol) in dichloromethane (60 mL, J. T. Baker 931533) and absolute ethanol (15 mL, Pharmco-AAPER 111000200) was added methanesulfonic acid (2.392 mL, 36.89 mmol, Sigma-Aldrich 471356). Stirred at room temperature until a clear solution was observed. Added heptane (300 mL) slowly over about 1 hr and collected the solid precipitate by filtration (using a Whatman qualitative #3 paper on top of a Whatman GF/F glass microfibre paper). Dried under reduced pressure in a vacuum oven (desiccated with calcium sulfate and potassium hydroxide) overnight at 40° C. giving 23A as a white solid (13.46 g, 99+% HPLC purity, 99+% ee). Analytical chiral HPLC shows one enantiomer with retention time of 8.6 min eluting with CH₂Cl₂/MeOH/TEA (60/40/0.1) on a CHIRALPAK® IC® 4.6×250 mm column with 1 mL/min flow rate at 30° C. A second crop of white solid product 23A (4.36 g, 98% HPLC purity, 99+% ee) was obtained from the filtrate. LCMS (C18 column eluting with 10-90% CH₃CN/water gradient over 5 minutes with formic acid modifier) M+1: 429.58 (2.03 min) ¹H NMR (300 MHz, MeOD) δ 9.00 (d, J=1.6 Hz, 2H), 7.67 (d, J=6.1 Hz, 1H), 5.39 (t, J=7.7 Hz, 1H), 4.30 (dd, J=14.9, 6.9 Hz, 1H), 4.03 (dd, J=14.8, 7.7 Hz, 1H), 3.40-3.31 (m, 2H), 2.72 (s, 3H), 2.70-2.60 (m, 1H), 2.21-2.08 (m, 2H), 1.98-1.84 (m, 1H), 1.65 (s, 6H), 1.22 (t, J=7.2 Hz, 3H) ppm.

The (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea 23 may then be converted to the phosphate or phosphate salt prodrugs according to the schemes set forth below.

0-23° C., DMF; (c) H₂, Pd/C, M⁺OH⁻ or D²⁺(OH⁻)₂, EtOH, H₂O; (d) aq H⁺; (e) aq M⁺OH⁻.

Compounds of formula (IB) may be prepared from compound 23 as shown in Scheme 1. In Step 1, compound 23 is treated with dibenzyl N,N-diisopropylphosphoramidite and tetrazole, followed by meta-chloroperoxybenzoic acid (mCPBA), to afford dibenzyl phosphate 24. In Step 2, hydrogenolysis of 24 in the presence of M⁺OH⁻ or D²⁺(OH⁻)₂ affords the dianionic form of the compound of formula (IB) (X=—PO(O⁻)₂.2M⁺ or —PO(O⁻)₂.D²⁺). The free acid form of the compound of formula (IB) (X=PO(OH)₂) may be obtained by treating the dianionic form with aqueous acid. The monoanionic form of the compound of formula (IB) (X=PO(OH)O⁻M⁺) may be obtained by treating the free acid form with one equivalent of M⁺OH⁻.

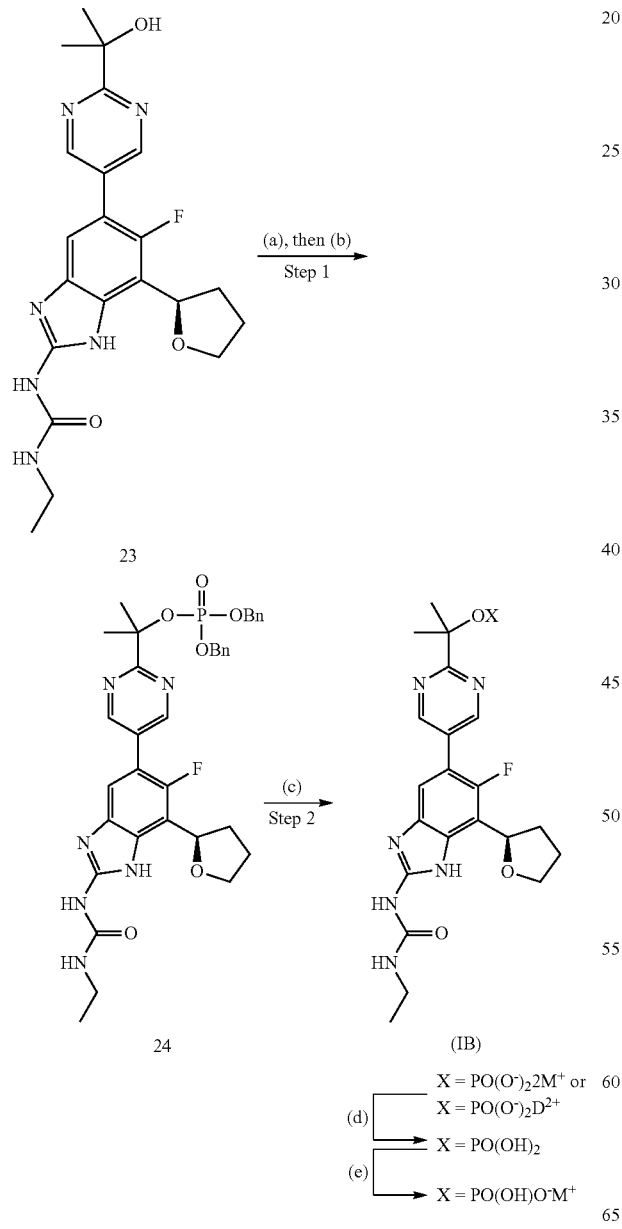

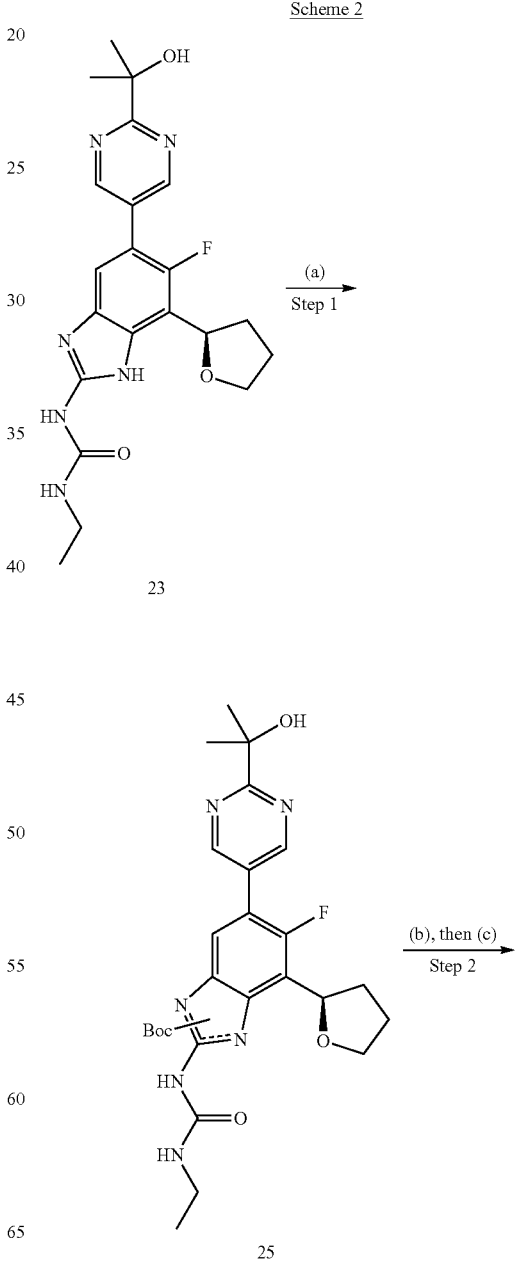

Reagents and conditions: (a) dibenzyl N,N-diisopropylphosphoramidite, tetrazole, 23° C., DMF; (b) mCPBA, 26 is treated with trifluoroacetic acid (TFA) to remove the protecting group and afford dibenzyl phosphate 24. In Step 4, hydrogenolysis of 24 in the presence of $M^+OH^-$ or $D^{2+}(OH^-)_2$ affords the dianionic form of the compound of formula (IB) (X=—PO(O$^-$)$_2$.2M$^+$ or —PO(O$^-$)$_2$.D$^{2+}$). The free acid form of the compound of formula (IB) (X=PO(OH)$_2$) may be obtained by treating the dianionic form with aqueous acid. The monoanionic form of the compound of formula (I) (X=PO(OH)O$^-$M$^+$) may be obtained by treating the free acid form with one equivalent of M$^+$OH$^-$.

Scheme 3

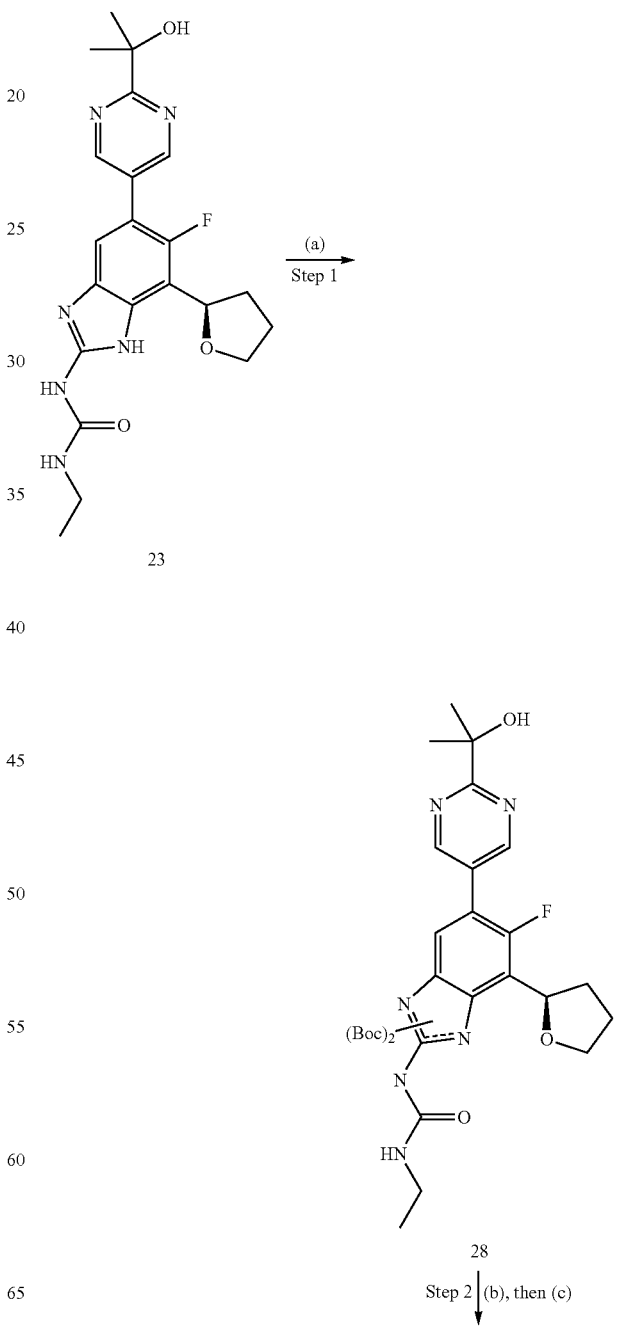

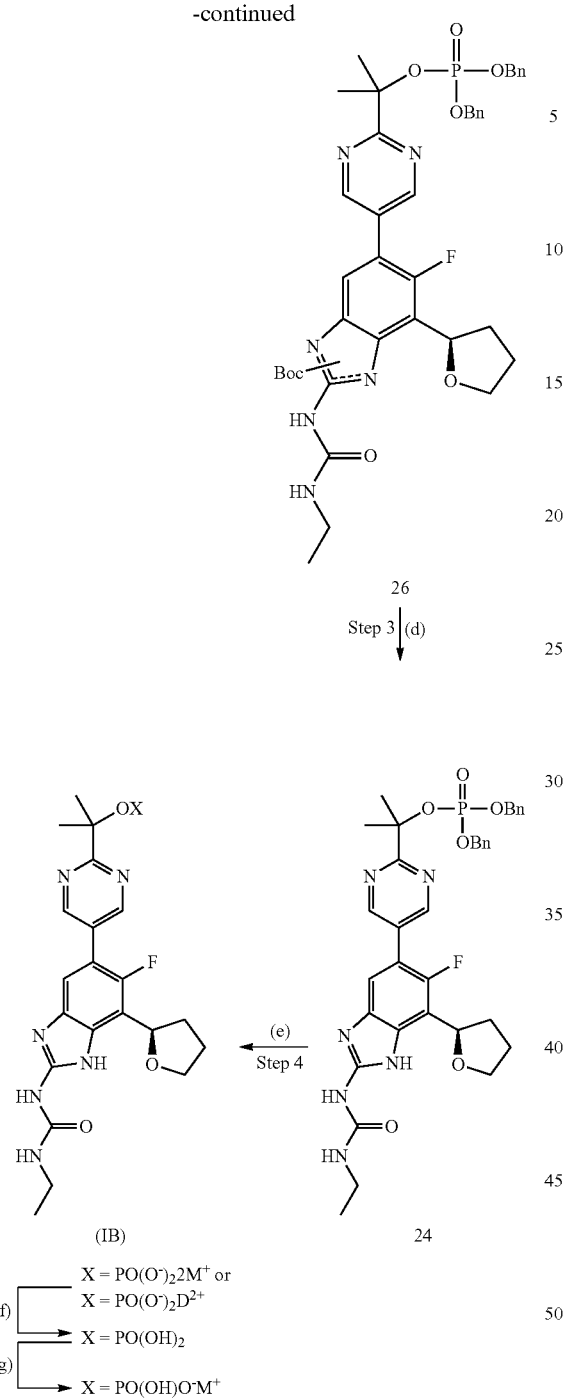

Reagents and conditions: (a) Boc$_2$O, DMF, 23° C.; (b) dibenzyl N,N-diisopropylphosphoramidite, tetrazole, 23° C., DMF; (c) mCPBA, 0-23° C., DMF; (d) TFA, H$_2$O, MeOH, DCM, 23° C.; (e) H$_2$, Pd/C, M$^+$OH$^-$ or D$^{2+}$(OH$^-$)$_2$, EtOH, H$_2$O; (f) aq H$^+$; (g) aq M$^+$OH$^-$.

Alternatively, the compounds of formula (IB) may be prepared from compound 23 as shown in Scheme 2. In Step 1, compound 23 is treated with di-tert-butyl dicarbonate (Boc$_2$O) to afford protected benzimidazole compound 25. In Step 2, compound 25 is treated with dibenzyl N,N-diisopropylphosphoramidite and tetrazole, followed by mCPBA, to afford protected dibenzyl phosphate 26. In Step 3, compound

45
-continued

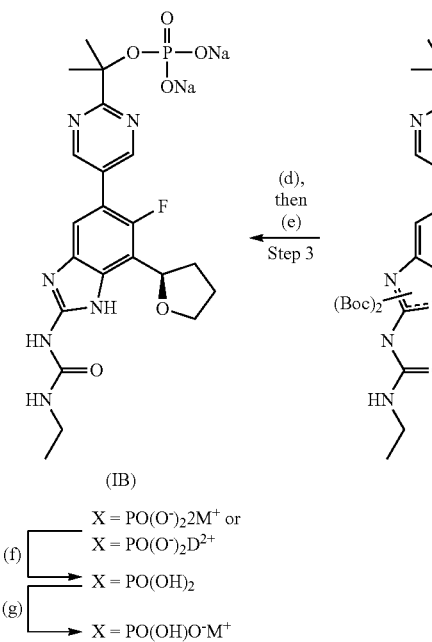

(f) X = PO(O⁻)₂2M⁺ or
     X = PO(O⁻)₂D²⁺
     → X = PO(OH)₂
(g) → X = PO(OH)O⁻M⁺

Reagents and conditions: (a) Boc₂O, DMAP, DMF, 23° C.; (b) dibenzyl N,N-diisopropylphosphoramidite, tetrazole, 23° C., DMF; (c) mCPBA, 0-23° C., DMF; (d) TFA, DCM; (e) aq M⁺OH⁻ or D²⁺(OH⁻)₂; (f) aq H⁺; (g) aq M⁺OH⁻.

The compounds of formula (IB) may also be prepared from compound 23 as shown in Scheme 3. In Step 1, compound 23 is treated with two equivalents of Boc₂O in the presence of N,N-dimethylaminopyridine (DMAP) to afford bis-protected benzimidazole compound 28. In Step 2, compound 28 is treated with dibenzyl N,N-diisopropylphosphoramidite and tetrazole, followed by mCPBA, to afford bis-protected dibenzyl phosphate 29. In Step 3, compound 29 is treated with TFA to remove the protecting groups. Treatment of the resulting intermediate with aqueous M⁺OH⁻ or D²⁺(OH⁻)₂ affords the dianionic form of the compound of formula (IB) (X=—PO(O⁻)₂.2M⁺ or —PO(O⁻)₂.D²⁺). The free acid form of the compound of formula (IB) (X=PO(OH)₂) may be obtained by treating the dianionic form with aqueous acid. The monoanionic form of the compound of formula (I) (X=PO(OH)O⁻M⁺) may be obtained by treating the free acid form with one equivalent of M⁺OH⁻.

46
Example 11
Preparation of (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24)

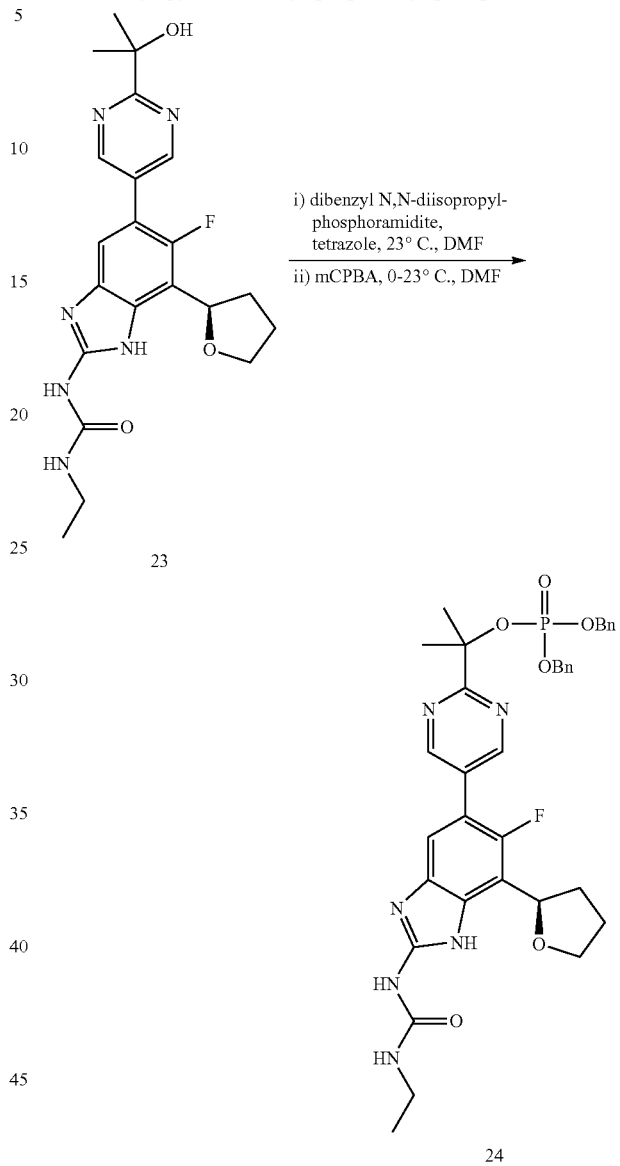

To 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (10.24 g, 23.66 mmol) in a 1 L round bottom flask under N₂ at 23° C. was added DMF (200 mL) followed by a solution of tetrazole (105.2 mL of 0.45 M in MeCN, 47.32 mmol) followed by N-dibenzyloxyphosphanyl-N-isopropyl-propan-2-amine (12.26 g, 11.93 mL, 35.49 mmol). After 4.5 h more N-dibenzyloxyphosphanyl-N-isopropyl-propan-2-amine (4 mL) was added. After stirring a further 16 h the reaction was cooled to 0° C. (ice-water bath) then treated with mCPBA (15.17 g, 61.52 mmol). The mixture was stirred at 0° C. for 30 min then at 23° C. for 30 min after which the reaction mixture was partitioned between water (400 mL) and EtOAc (700 mL). The organic layer was separated, washed with saturated aqueous sodium bicarbonate (500 mL), 10% aqueous sodium bisulfate (500 mL), saturated aqueous sodium bicarbonate (500 mL), and brine (500 mL) then dried (magnesium sulfate), filtered and concentrated. The residue was purified by MPLC using an ISCO COMBIFLASH brand flash chromatography purification system (330 g column) eluting with a 0-10% EtOH in DCM linear gradient over 16.5 column volumes at a 200 mL/min flow rate. After concentration in vacuo, (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-ylphosphate (24) (13.89 g, 20.17 mmol, 85.27%) was obtained as a white solid. ESMS (M+1)=689.5; $^1$H NMR (300 MHz, CD$_3$OD) δ 8.88 (d, J=1.6 Hz, 2H), 7.37 (d, J=6 Hz, 1H), 7.30 (m, 10H), 5.38-5.33 (m, 1H), 5.12-5.01 (m, 4H), 4.24 (dd, J=6.8, 14.9 Hz, 1H), 3.98 (dd, J=6.9, 15.1 Hz, 1H), 3.35-3.27 (m, 3H), 2.52 (q, J=5.9 Hz, 1H), 2.14-2.05 (m, 2H), 1.91 (s, 6H) and 1.22-1.14 (m, 3H) ppm.

Example 12

Preparation of disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W)

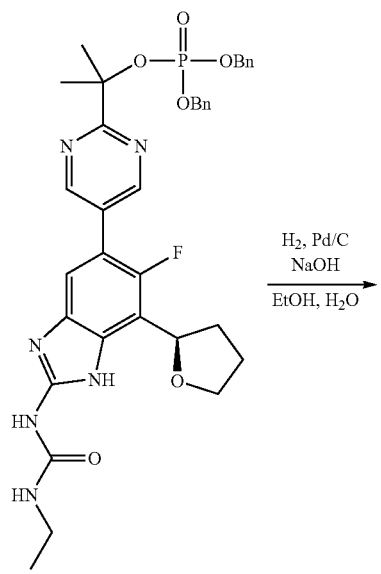

aqueous 1 M NaOH (40.34 mL, 40.34 mmol). The resulting mixture was hydrogenated under 50 psi H$_2$ on a Parr shaker apparatus for 40 min. The reaction mixture was filtered through a 0.22 μm polyethersulfone (PES) membrane giving a dark colored filtrate. A water rinse resulted in more dark material crossing the filter membrane. The resulting filtrate was passed through a pad of Celite and the dark material did not elute until the pad was rinsed with water. The resulting dark solution (approx. 700 mL) was diluted with three volumes of EtOH (2100 mL), filtered through a 0.22 μm PES membrane (using 4 disposable Corning polystyrene filter systems, #431098) and the filtrate concentrated in vacuo. The resulting residue was dissolved in water (100 mL) and EtOH (300 mL), filtered through a 0.22 μm PES membrane to give a clear yellow solution, then passed through a Celite plug (26 mm diameter×60 mm height, pre-wet with EtOH) rinsing with EtOH (50 mL) and the filtrate then concentrated. The resulting residue was dissolved in water (250 mL) in a 1 L round bottom flask, then 1 M aqueous HCl (40 mL) was slowly added over 15 min with stirring to give a slurry of white solid. Twenty minutes following completion of the HCl addition, the solid was collected via filtration through a 0.22 μm PES membrane. The collected solid was washed with water (100 mL), then transferred (still wet) to a 1 L round bottom flask and slurried in MeOH (150 mL) for 30 min. The resulting fine white precipitate was collected via filtration then dried in vacuo overnight. The resulting free acid (9.17 g, 18.0 mmol) was treated with water (80 mL) then 1.0 N aq NaOH (36.0 mL, 2 equiv). The resulting solution was frozen and lyophilized to give disodium [1-[5-[2-(ethylcarbamoylamino)-6-fluoro-7-[(2R)-tetrahydrofuran-2-yl]-1H-benzimidazol-5-yl]pyrimidin-2-yl]-1-methyl-ethyl]phosphate (W) (10.206 g, 18.08 mmol, 89.66%) as a pale, cream-colored solid with consistent analytical data. ESMS (M+1)=509.4; $^1$H NMR (300 MHz, D$_2$O) δ 8.58 (s, 2H), 6.92 (d, J=6.3 Hz, 1H), 5.13 (t, J=7.5 Hz, 1H), 3.98-3.81 (m, 2H), 3.04 (q, J=7.2 Hz, 2H), 2.26 (t, J=5.7 Hz, 1H), 1.97-1.92 (m, 2H), 1.67 (s, 6H) and 1.01 (t, J=7.2 Hz, 3H) ppm.

Example 13

Preparation of Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (25)

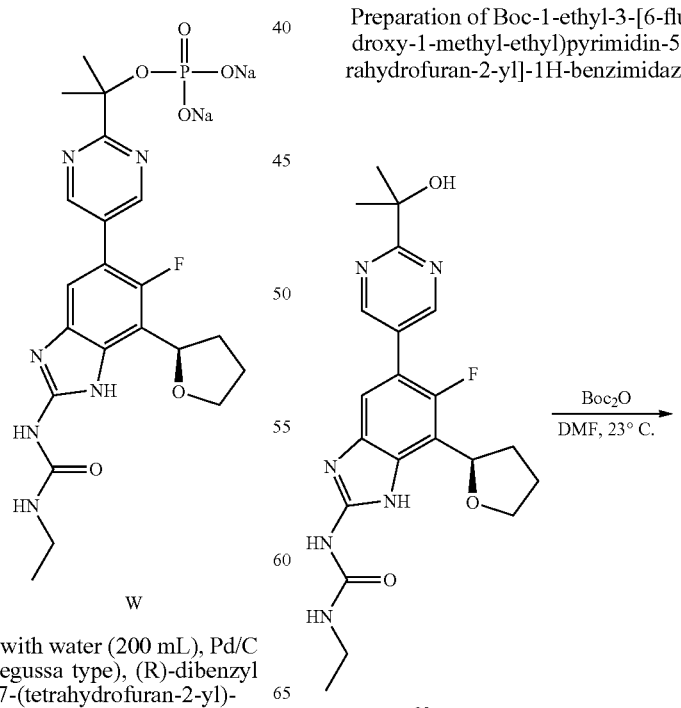

A 1 L Parr vessel was charged with water (200 mL), Pd/C (4 g, 10 wt % dry basis, wet, Degussa type), (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-ylphosphate(24) (13.89 g, 20.17 mmol), EtOH (400 mL) and

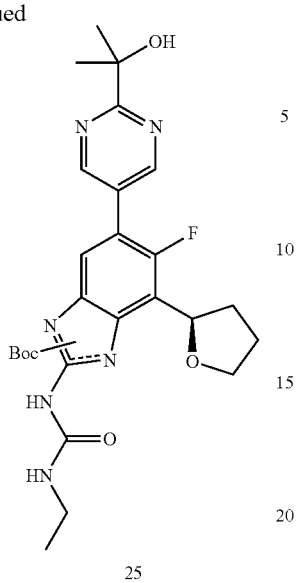

25

To a solution/suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (10.72 g, 25.02 mmol) in DMF (250 mL) at 23° C. was added Boc₂O (6.11 g, 28.00 mmol). After 2 hours, 2 M ammonia in MeOH (2 mL) was added to quench any excess Boc₂O. The quenched reaction mixture was partitioned between EtOAc and water (400 mL each), the organic layer separated, washed with water (2×400 mL) and brine (400 mL), then dried over MgSO₄, filtered and concentrated to give Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (25) (12.69 g, 23.58 mmol, 94.26%) which was used without further purification. ESMS (M+1)=529.3; ¹H NMR (300.0 MHz, CDCl₃) δ 9.50 (s, 1H), 9.02 (t, J=5.3 Hz, 1H), 8.91 (d, J=1.6 Hz, 2H), 7.74 (d, J=6.5 Hz, 1H), 5.58 (t, J=7.8 Hz, 1H), 4.64 (s, 1H), 4.22 (q, J=7.4 Hz, 1H), 4.05 (td, J=7.8, 4.3 Hz, 1H), 3.47 (td, J=7.2, 4.3 Hz, 2H), 2.42-2.35 (m, 2H), 2.28-2.16 (m, 2H), 1.75 (s, 9H), 1.68 (s, 6H) and 1.31 (t, J=7.3 Hz, 3H) ppm.

Example 14
Preparation of Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (26)

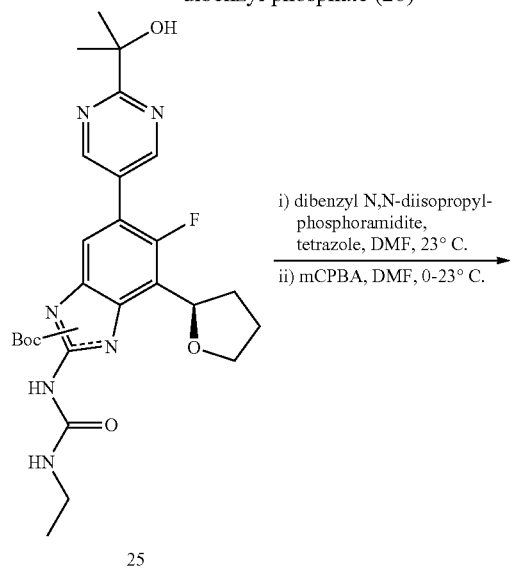

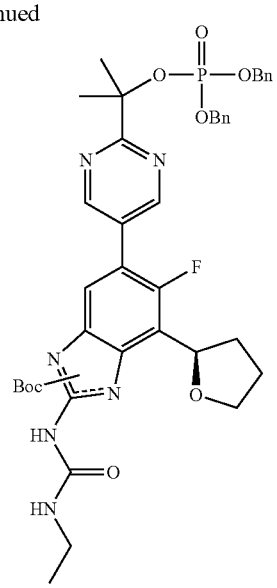

26

To Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (25) (12.69 g, 23.58 mmol) and tetrazole (3.304 g, 47.16 mmol) under N₂ at 23° C. was added DCM (240 mL) followed by N-dibenzyloxyphosphanyl-N-isopropyl-propan-2-amine (9.775 g, 9.509 mL, 28.30 mmol). After 3 hours at 23° C., the reaction was cooled to 0° C. then mCPBA (6.977 g, 28.30 mmol) was added. The resulting solution was stirred for 45 min at 0° C. then for 20 min at 23° C. The reaction mixture was then partitioned between DCM (50 mL) and saturated aqueous sodium bicarbonate (400 mL). The organic layer was separated, then washed successively with aqueous sodium bisulfate (63 g in 350 mL water) and saturated aqueous sodium bicarbonate (400 mL), then dried over magnesium sulfate, filtered and concentrated in vacuo. The residue was purified by MPLC using an ISCO COMBI-FLASH brand flash chromatography purification system (330 g silica column) eluting with a 0-100% EtOAc in hexanes linear gradient over 16 column volumes at 200 mL/min. Product containing fractions were evaporated in vacuo to give Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (26) (11.92 g, 15.11 mmol, 64.09%). ESMS (M+1)=789.2; ¹H NMR (300.0 MHz, CDCl₃) δ 9.51 (s, 1H), 9.03 (t, J=5.4 Hz, 1H), 8.91 (d, J=1.6 Hz, 2H), 7.73 (d, J=6.5 Hz, 1H), 7.37-7.28 (m, 10H), 5.58 (t, J=7.8 Hz, 1H), 5.17-5.05 (m, 4H), 4.23 (t, J=7.5 Hz, 1H), 4.05 (td, J=7.8, 4.3 Hz, 1H), 3.53-3.44 (m, 2H), 2.39 (dd, J=7.9, 14.5 Hz, 2H), 2.28-2.15 (m, 2H), 1.98 (s, 6H), 1.72 (m, 9H) and 1.31 (t, J=7.2 Hz, 3H) ppm.

Example 15

Preparation of (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24)

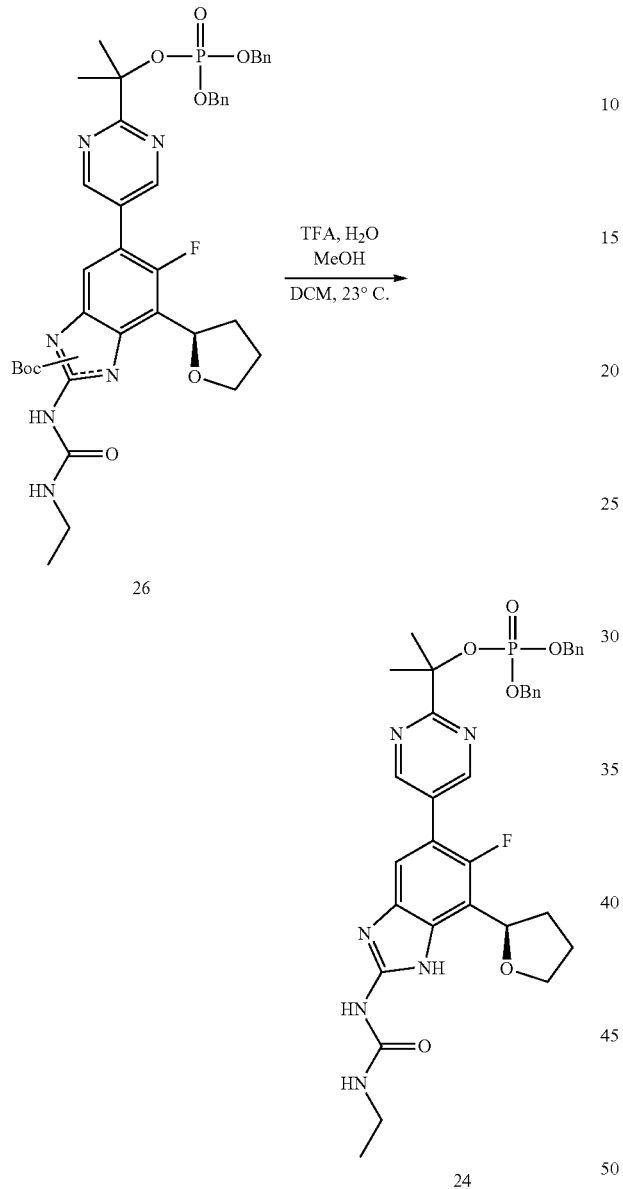

To a solution of Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (26) (11.9 g, 15.09 mmol) in DCM (300 mL) at 23° C. was added water (2.325 mL, 129.1 mmol) then TFA (3.441 g, 2.325 mL, 30.18 mmol). After 1 h, only partial conversion was observed by tlc, so more TFA (3.441 g, 2.325 mL, 30.18 mmol) was added. After a further 2.5 h, MeOH (2 mL) was added and the mixture stirred a further 18 hours. The reaction mixture was washed with 1:1 brine:saturated aqueous sodium bicarbonate (200 mL). The aqueous layer was re-extracted with DCM (150 mL), the organic layers combined, then dried (over magnesium sulfate), filtered and concentrated in vacuo. The resulting residue was re-dissolved in EtOAc (200 mL) washed with water (150 mL) and brine (100 mL), then dried (magnesium sulfate) filtered and concentrated to give (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24) (10.21 g, 14.83 mmol, 98.27%) as a white solid. ESMS (M+1)=689.4; $^1$H NMR (300 MHz, CD$_3$OD) δ 8.88 (d, J=1.6 Hz, 2H), 7.37 (d, J=6 Hz, 1H), 7.30 (m, 10H), 5.38-5.33 (m, 1H), 5.12-5.01 (m, 4H), 4.24 (dd, J=6.8, 14.9 Hz, 1H), 3.98 (dd, J=6.9, 15.1 Hz, 1H), 3.35-3.27 (m, 3H), 2.52 (q, J=5.9 Hz, 1H), 2.14-2.05 (m, 2H), 1.91 (s, 6H) and 1.22-1.14 (m, 3H) ppm.

Example 16

Preparation of disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W)

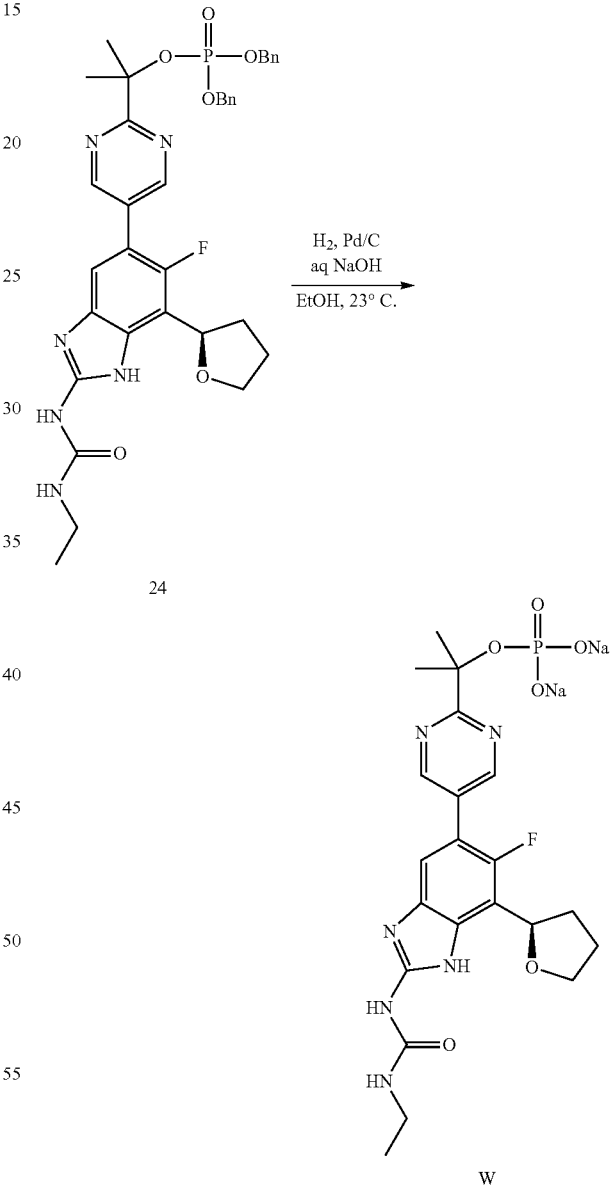

A 1 L round bottom flask was charged with (R)-dibenzyl 2454243-ethylureido)-6-fluoro-7-(tetrahydrofuran-2-yl)-1H-benzo[d]imidazol-5-yl)pyrimidin-2-yl)propan-2-yl phosphate (24) (9.37 g, 13.61 mmol), EtOH (300 mL), water (150 mL), Pd/C (10 wt % dry basis, wet, Degussa type, 3 g) and 1 M aqueous NaOH (27.22 mL, 27.22 mmol). The suspension was evacuated for 3 min (needle to pump) then placed under an atmosphere of hydrogen gas (balloon). After stirring 2.5 h at 23° C., the reaction was filtered through a 0.22 μm PES membrane (disposable Corning filter system, 1 L, polystyrene, #431098) to remove catalyst and washed with EtOH (50 mL). The resulting solution was concentrated, the residue dissolved in water (80 mL), treated with MeCN (80 mL), then frozen and lyophilized to give disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W) (7.10 g, 12.81 mmol, 94.12%) as a white solid. ESMS (M+1)=509.3; $^1$H NMR (300 MHz, D$_2$O) δ 8.58 (s, 2H), 6.92 (d, J=6.3 Hz, 1H), 5.13 (t, J=7.5 Hz, 1H), 3.98-3.81 (m, 2H), 3.04 (q, J=7.2 Hz, 2H), 2.26 (t, J=5.7 Hz, 1H), 1.97-1.92 (m, 2H), 1.67 (s, 6H) and 1.01 (t, J=7.2 Hz, 3H) ppm.

Example 17

Preparation of diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (28)

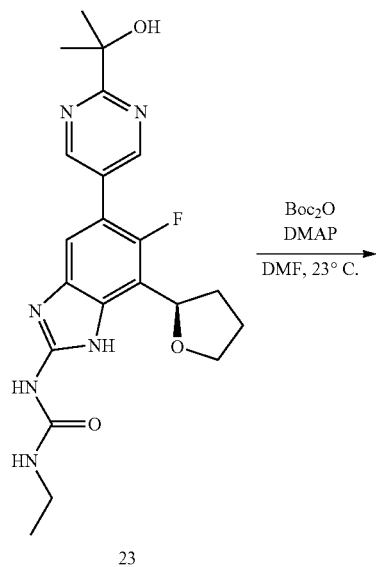

To a solution/suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (1.333 g, 3.111 mmol) in DMF (30 mL) was added DMAP (38.01 mg, 0.3111 mmol) followed by Boc$_2$O (1.426 g, 1.501 mL, 6.533 mmol). After 30 min, the reaction mixture was diluted with water and EtOAc (300 mL each), the organic layer separated, washed with water and brine (300 mL each), then dried over magnesium sulfate, filtered and concentrated. The residue was purified by MPLC using an ISCO COMBIFLASH brand flash chromatography purification system (80 g silica column) eluting with a 0-60% EtOAc in hexanes linear gradient over 20 column volumes at 60 mL/min flow rate. Desired product fractions were combined and evaporated to give diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (28) (1.43 g, 2.275 mmol, 73.11%) as a clear foam. ESMS (M+1)=629.3; $^1$H NMR (300.0 MHz, CDCl$_3$) δ 8.95 (d, J=1.6 Hz, 2H), 8.31-8.27 (m, 1H), 8.05 (d, J=6.5 Hz, 1H), 5.80-5.68 (m, 1H), 4.70 (s, 1H), 4.21-4.09 (m, 1H), 3.98 (d, J=6.4 Hz, 1H), 3.42-3.37 (m, 2H), 2.45-2.00 (m, 4H), 1.65 (s, 6H), 1.62 (s, 9H), 1.37 (s, 9H) and 1.28-1.21 (m, 3H) ppm.

Example 18

Preparation of diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (29)

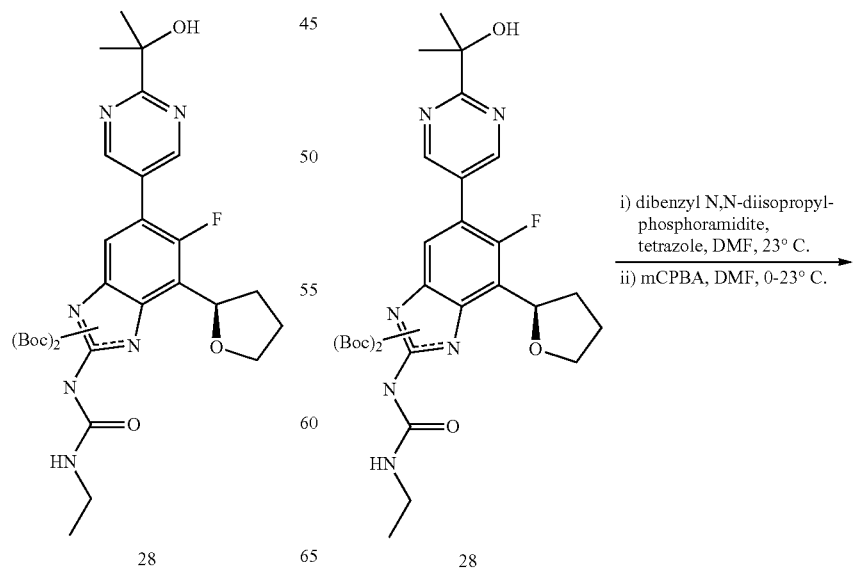

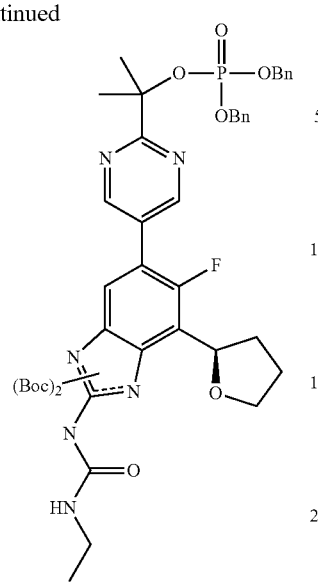

29

To diBoc-1-ethyl-3-[6-fluoro-5-[2-(1-hydroxy-1-methylethyl)pyrimidin-5-yl]-7-[(2R)-tetrahydrofuran-2-yl]-1H-benzimidazol-2-yl]urea (28) (1.13 g, 1.797 mmol) and tetrazole (251.8 mg, 3.594 mmol) at 23° C. under $N_2$ was added DCM (30 mL) followed by N-dibenzyloxyphosphanyl-N-isopropyl-propan-2-amine (744.7 mg, 724.4 µL, 2.156 mmol). After stirring for 18 h, the reaction was cooled to 0° C. then treated with mCPBA (531.5 mg, 2.156 mmol). The reaction was stirred for 15 min at 0° C., then for 30 min at 23° C. The resulting solution was then partitioned between EtOAc and saturated aqueous sodium bicarbonate (300 mL each), the organic layer separated, then washed with 10% aqueous sodium bisulfite, saturated aqueous sodium bicarbonate and brine (300 mL each), then dried over magnesium sulfate filtered and concentrated. The residue was purified by MPLC using an ISCO COMBIFLASH brand flash chromatography purification system (80 g silica column) eluting with a 0-80% EtOAc in hexanes linear gradient over 20 column volumes at 60 mL/min flow rate. Desired product fractions were combined and evaporated to give diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (29) (1.03 g, 1.159 mmol, 64.50%) as a clear, glassy oil. ESMS (M+1)=889.5; $^1$H NMR (300.0 MHz, CDCl$_3$) δ 8.93 (d, J=1.5 Hz, 2H), 8.31 (s, 1H), 8.04 (d, J=6.4 Hz, 1H), 7.36-7.26 (m, 10H), 5.83-5.70 (m, 1H), 5.16-5.05 (m, 4H), 4.24-4.18 (m, 1H), 4.03-3.97 (m, 1H), 3.42-3.36 (m, 2H), 2.43-2.05 (m, 4H), 1.98 (s, 6H), 1.64 (s, 9H), 1.40 (s, 9H) and 1.26 (t, J=7.2 Hz, 3H) ppm.

Example 19

Preparation of disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W)

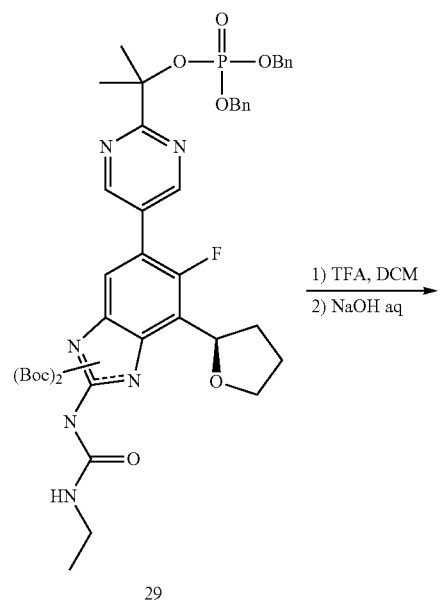

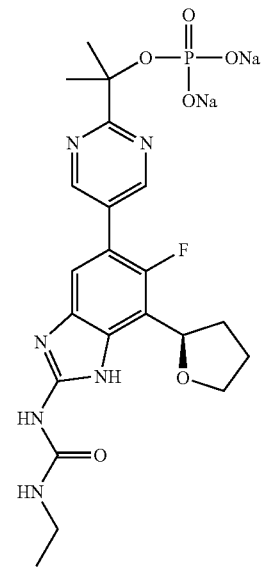

W

To a solution of diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (29) (121 mg, 0.1361 mmol) in DCM (10 mL) at 23° C. was added TFA (5 mL). After 2 h, the reaction mixture was concentrated in vacuo. The residue was dissolved in MeOH (6 mL) and treated with approx 0.5 mL 2 M NH$_3$ in MeOH (to fully dissolve the material). The resulting solution was purified in 6 injections on preparative HPLC, reverse phase, Sunfire prep C18 OBD 5 µM column 19×100 mm; eluting with a 10-90% aq MeCN w/0.1% TFA buffer, linear gradient over 15 min at 20 mL/min flow rate. Fractions containing product were pooled and lyophilized. The resulting material was suspended in MeOH (3 mL), stirred at 23° C. for 30 min, then the precipitate was collected via filtration through a plastic frit. The resulting white solid was re-subjected to a MeOH slurry (3 mL), then collected via filtration to give 68 mg of white solid after drying. The white solid was treated with 0.10 M aq NaOH (2.68 mL, 2 equiv NaOH) to give a solution that was then passed through an Acrodisc CR 13 mm syringe filter with 0.45 μm PTFE membrane, flushing with water (2 mL). The resulting solution was treated with MeCN (3 mL), frozen and lyophilized to give sodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W) as a white powder. ESMS (M+1)=509.2; $^1$H NMR (300 MHz, D$_2$O) δ 8.58 (s, 2H), 6.92 (d, J=6.3 Hz, 1H), 5.13 (t, J=7.5 Hz, 1H), 3.98-3.81 (m, 2H), 3.04 (q, J=7.2 Hz, 2H), 2.26 (t, J=5.7 Hz, 1H), 1.97-1.92 (m, 2H), 1.67 (s, 6H) and 1.01 (t, J=7.2 Hz, 3H) ppm.

Example 20

Free Form A 150.91 mg of the compound of formula (I) (amorphous sodium salt, with 2 equivalents of sodium) was weighed out in 4 mL clear vial. 0.5 mL of water was added to dissolve the compound. To the resulting solution 0.5 mL 1N HCl was added drop wise under stirring. The resulting suspension was allowed to equilibrate under stirring for 24 hours. The solid was filtered through the centrifuge filter (Millipore, PVDF 0.22 micron pore size membrane). The solid was washed 5 times with acetonitrile aliquots and dried under house vacuum for 96 hours. This yielded 113.45 mg of Free Form A as a white to off-white solid.

Example 21

Free Form B

Form A sample was heated to 60° C. on a PXRD stage and data collected at that temperature. Upon exposure to this temperature Free Form A loses water (about 6%) and converts to anhydrous Free Form B. Free Form B converts rapidly (within minutes) back to Free Form A depending on temperature and humidity. At 25° C., the critical humidity for conversion is around 40% (see vapor sorption experiment).

Example 22

Free Form C

In order to prepare Free Form C, 40 mg of Free Form A was placed in an HPLC vial with a small stir bar and 0.1 mL n-pentanol was added to the vial. The vial was left to equilibrate in the EppendorfThermomixer® at 60° C. with 500 rpm orbital shaking for 5 days. The white powder was isolated by centrifugal filtration (0.22 micron pore size PDVF membrane) and dried under vacuum at ambient temperature (20° C.) to give Free Form C.

Example 23

Sodium salt Form X

To prepare sodium salt Form X (a di-sodium salt) of the compound of formula (I), 69.7 mg of Free Form A was placed in the 2 dram vial and 2 ml of an acetonitrile:water 90:10 mixture was added. 6N NaOH aqueous solution was added in 104, increments checking pH until the pH reached about 8.5 (about 60 μL). The two phase liquid system with an excess of solid that formed was allowed to equilibrate under magnetic stirring for 20 hours at 500 rpm. One liquid phase with an off-white powder (suspension) formed with the final pH of 12.5.

The solid was isolated by centrifugal filtration (0.22 micron PVDF membrane), washed 2 times with 0.3 mL aliquots of an acetonitrile:water 9:1 mixture, then washed twice with 0.3 mL aliquots of acetonitrile. The sample was dried under house vacuum at ambient temperature (20° C.) for 5 h to yield the final product as a white powder.

Example 24

Amorphous di-sodium Salt

Amorphous di-sodium salt was prepared according to Example 19 described herein.

Example 25

DVS Method 2-10 mg of sample were placed on an instrument pan, and the sample equilibrated at 25° C. and 0% relative humidity (RH). Humidity was then changed from 5 to 55% in increments of 10% RH, using equilibration condition as <0.0025% weight change in 15 min or 3 hours whichever came first. Humidity was then changed by 5% increments until 95% RH was achieved using the same limiting conditions. The reverse steps were executed on the desorption side from 95% down to 5% RH, while always maintaining 25° C. temperature.

In one embodiment, free Form A was the most stable form as measured by net percent increase in total impurities after 15 days at 40 degrees Celsius and 30% relative humidity (see Table 5 below).

TABLE 5

Stability Data of the solid Forms

| Form | Time at 40 C./ 30% RH, days | Net % increase in total impurities |
|---|---|---|
| amorphous di-Na salt | 15 | 1.74 |
| A | 15 | 0.07 |
| B | 17 | 0.16 |
| C | 17 | 0.18 |
| X (crystalline di-Na salt) | 17 | 0.59 |

Uses and Pharmaceutically Acceptable Compositions

The compounds of formula (I) are useful generally for controlling bacterial infections in vivo. Examples of bacterial organisms that may be controlled by the compositions and methods of this invention include, but are not limited to the following organisms: *Streptococcus pneumoniae, Streptococcus pyogenes, Enterococcus faecalis, Enterococcus faecium, Klebsiella pneumoniae, Enterobacter* spp. *Proteus* spp. *Pseudomonas aeruginosa, E. coli, Serratia marcescens, Staphylococcus aureus*, Coag. Neg. Staphylococci, *Haemophilus influenzae, Bacillus anthracis, Mycoplasma pneumoniae, Moraxella catarrhalis, Chlamydophila pneumoniae, Chlamydia trachomatis, Legionella pneumophila, Mycobacterium tuberculosis, Helicobacter pylori, Staphylococcus saprophyticus, Staphylococcus epidermidis, Francisella tularensis, Yersinia pestis, Clostridium difficile, Neisseria gonorrhoeae, Neisseria meningitidis, Mycobacterium avium complex, Mycobacterium abscessus, Mycobacterium kansasii and Mycobacterium ulcerans.

The compounds, compositions and methods will therefore be useful for controlling, treating or reducing the advancement, severity or effects of nosocomial or non-nosocomial infections. Examples of nosocomial and non-nosocomial infections include but are not limited to upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections. Examples of specific bacterial infections include but are not limited to uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial pneumoniae (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

Example 24

Susceptibility Testing in Liquid Media

Compounds of this invention were tested for antimicrobial activity by susceptibility testing in liquid media. Such assays were performed within the guidelines of the latest CLSI document governing such practices: "M07-A8 Methods for Dilution Antimicrobial Susceptibility Tests for Bacteria that Grow Aerobically; Approved Standard—Eighth Edition (2009)". Other publications such as "Antibiotics in Laboratory Medicine" (Edited by V. Lorian, Publishers Williams and Wilkins, 1996) provide essential practical techniques in laboratory antibiotic testing. The specific protocols used were as follows:

Protocol 4. MIC Determination Procedure for *Mycobacterium* Species
  Materials
  Round bottom 96-well microtiter plates (Costar 3788) or similar
  Film plate seals (PerkinElmer, TopSeal-A #6005250 or similar)
  Middlebrook 7H10 broth with 0.2% glycerol
  Middlebrook 7H10 agar with 0.2% glycerol
  Middlebrook OADC Enrichment
  Inoculum Preparation for *M. tuberculosis*:
  1. Used prepared frozen *M. tuberculosis* stock stored at −70° C. *M. tuberculosis* was grown in 7H10 broth+10% OADC, then frozen at a concentration of 100 Klett or $5 \times 10^7$ cfu/ml,
  2. Prepared a 1:20 dilution by removal of 1 ml of the frozen stock and added it to 19 ml of 7H10 broth+10% OADC (final concentration $2.5 \times 10^6$ cfu/ml).
  3. From this dilution prepared a second 1:20 dilution, removed 1 ml and added it to 19 ml of fresh broth. This was the final inoculum to add to the 96-well plates.
  Inoculum Preparation for *M. kansasii, M. avium, M. abscessus* and *Nocardia* spc.:

1. Used prepared frozen stock of culture or a fresh culture grown in 7H10 broth at a concentration of 10 Klett or $5\times10^7$/ml.
2. Prepared a 1:20 dilution by removing 1.0 ml of the culture stock and added it to 19 ml of 7H10 broth (final concentration $2.5\times10^6$ cfu/ml).
3. From this dilution prepared a 1:20 dilution, removed 1 ml and added it to 19 ml of fresh broth (final suspension).

Plate Preparation:

1. Labeled plates.
2. Added 50 µl of 7H10 broth+10% OADC to all wells being utilized for MIC determination using a multichannel electronic pipettor.
3. Prepared stock solutions of drugs (e.g. 1 mg/ml concentration) to be tested.
4. Thawed and diluted frozen stock solutions using 7H10 broth+10% OADC to obtain a working solution 4× the maximum concentration tested (e.g. final concentration 32 µg/ml, highest concentration tested was 8 µg/ml). Dilutions were made from the stock solution. To start at a concentration of 1 µg/ml, the drugs were prepared at 4 µg/ml, so the starting concentration was 1 µg/ml. Removed 25 µl of the 1 mg/ml stock and added to 6.2 ml of broth. All dilutions of drugs were done in broth.
5. Added 50 µl of the 4× working solution to the first well of the designated row. Continued for all compounds to be tested. Using a multichannel electronic pipettor, mixed 4× and serial diluted compounds through the 11th well. Discarded remaining Used the 12th well as the positive control.
6. Incubated plates at 37° C. *M. tuberculosis* for ~18 days; *M. avium* and *M. kansasii* for ~7 days; *Nocardia* and *M. abcessus* for ~4 days; with film seals.
7. Read visually and recorded the results. The MIC was recorded as the lowest concentration of drug where no growth was observed (optical clarity in the well).

Protocol 5. Protocol for *Mycobacterium tuberculosis* Serum Shift MIC Assay

Materials And Reagents:

Costar #3904 Black-sided, flat-bottom 96-well microtiter plates

Middlebrook 7H9 broth (BD271310) with 0.2% glycerol

Middlebrook OADC Enrichment

Fetal Bovine Serum

Catalase (Sigma C1345)

Dextrose

NaCl

BBL Prompt Inoculation System (Fisher b26306)

Agar plates (Middlebrook 7H11 with 0.2% glycerol and OADC enrichment) with bacteria streaked to single colonies Sterile DMSO Media Prep:

1. For serum shifted MICs, three different media were required which all had a base of 7H9+0.2% glycerol. It was important that all media and supplements were sterilized prior to MICs.
2. Prepared all media below and inoculated as described in next section. Tested all compounds against Mtb using each media.

a. 7H9+0.2% glycerol+10% OADC ("standard" MIC media).
b. 7H9+0.2% glycerol+2 g/L dextrose+0.85 g/L NaCl+ 0.003 g/L catalase (0% FBS).
c. 2×7H9+0.2% glycerol+2 g/L dextrose+0.85 g/L NaCl+0.003 g/L catalase combined with equal volume Fetal Bovine Serum (50% FBS).

Inoculum Prep:
1. Using BBL Prompt, picked 5-10 well-separated colonies and inoculated 1 ml sterile saline that came in the kit. Typically plates were two to three weeks of age when used for this assay due to the slow growth of this organism in culture.
2. Vortexed well, then sonicated in water bath for 30 sec providing a suspension of ~$10^8$ cells/ml. Actual density could be confirmed by plating out dilutions of this suspension.
3. Prepared inoculum in each of the three media formulations by diluting the BBL
Prompt suspension 1/200 (for example: transferred 0.2 ml of cells to 40 ml of medium) to obtain a starting cell density of ~$10^6$ cells/ml.
4. Used 100 µl cells (~$5\times10^4$ cells) to inoculate each microtiter well containing 1 µl of drug in DMSO (see below).

Drug Dilutions, Inoculation, MIC Determination:
1. Control drug stocks Isoniazid and Novobiocin were prepared at 10 mM in 100% DMSO while Ciprofloxacin and Rifampin were prepared at 1 mM in 50% DMSO and 100% DMSO, respectively. Prepared dilutions-dispensed 100 µL of the stock solution into the first column of a 96-well plate. Prepared 11-step, 2-fold serial dilutions across the row for each compound by transferring 50 µl from column 1 into 50 µl of DMSO in column 2 Continued to transfer 50 µL from column 2 through column 11 while mixing and changing tips at each column. Left column 12 with DMSO only as a control.
2. Transferred 1 µl of each dilution into an empty microtiter well prior to the addition of 100 µl of cells. The starting concentration of Isoniazid and Novobiocin was 100 µM after the dilution into medium+cells; the starting concentration of Ciprofloxacin and Rifampin was 10 µM after the dilution into medium+cells. Compound concentrations decreased in 2× steps moving across the rows of the microtiter plate. All MICs were done in duplicate at each of the three medium conditions.
3. Test sets of compounds were typically at 10 mM and 50 µL volume.
4. Used a multichannel pipettor, removed all of the volume from each column of the master plate and transferred into the first column of a new 96-well microtiter plate. Repeated for each column of compounds on master plate, transferring into column 1 of a new 96-well plate.
5. As described above for control compounds, generated 2-fold, 11-point dilutions of each compound using DMSO as diluent. In all cases, left column 12 as DMSO only for a control. Once all dilutions were complete, again transferred 1 µl of each dilution into an empty microtiter well prior to the addition of 100 µl of cells as done for the control compounds.
6. All wells were inoculated with 100 µl of diluted cell suspension (see above).
7. After inoculum addition, mixed plates by gently tapping sides of plate.
8. Plates were incubated in a humidified 37° C. chamber for 9 days.
9. At 9 days added 25 µl 0.01% sterile resazurin to each well. Measured background fluorescence at Excitation 492 nm, Emission 595 nm and returned the plate to the incubator for another 24 hours.

After 24 hours the fluorescence of each well was measured at Excitation 492 nm, Emission 595 nm.

Percent inhibition by a given compound was calculated as follows: Percent inhibition=100−([well fluorescence-average background fluorescence]/[DMSO control−average background fluorescence]×100). MICs were scored for all three medium conditions as the lowest compound concentration that inhibited resazurin reduction ('%-inhibition') signal ≥70% at a given medium condition.

Table 6 shows the results of the MIC assay for selected compounds of this invention.

In Table 6 and in subsequent Tables and Examples, "Compound 12" corresponds to 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea and "Compound 13" relates to the mesylate salt of Compound 12. Similarly, "Compound 23" corresponds to 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea and "Compound 23A" relates to the mesylate salt of Compound 23. These are the same numbers used to identify said compounds and salts as used in the Examples above.

TABLE 6

MIC Values of Selected Compounds

| | | MIC (µg/ml) | |
| --- | --- | --- | --- |
| Strain/Special Condition | Protocol | Compound 13 | Compound 23A |
| Mycobacterium avium 103 | 4 | 0.47 | 0.18 |
| M. avium Far | 4 | 0.94 | 0.23 |
| M. avium 3404.4 | 4 | 0.94 | 0.23 |
| M. kansasii 303 | 4 | Not Done | 0.03 |
| M. kansasii 316 | 4 | Not Done | 0.06 |
| M. kansasii 379 | 4 | Not Done | <0.015 |
| M. tuberculosis H37Rv ATCC 25618 | 4 | 0.37 | 0.015 |
| M. tuberculosis Erdman ATCC 35801 | 4 | 0.25 | 0.06 |
| M. tuberculosis Erdman ATCC 35801 | 5 | 0.045 | 0.03 |
| M. tuberculosis Erdman ATCC 35801 with Mouse Serum | 5 | 2 | 0.5 |
| M. abscessus BB2 | 4 | Not Done | 1 |
| M. abscessus MC 6005 | 4 | Not Done | 1 |
| M. abscessus MC 5931 | 4 | Not Done | 0.5 |
| M. abscessus MC 5605 | 4 | Not Done | 1.5 |
| M. abscessus MC 6025 | 4 | Not Done | 0.75 |
| M. abscessus MC 5908 | 4 | Not Done | 1.5 |
| M. abscessus BB3 | 4 | Not Done | 0.5 |
| M. abscessus BB4 | 4 | Not Done | 2 |
| M. abscessus BB5 | 4 | Not Done | 0.5 |
| M. abscessus MC 5922 | 4 | Not Done | 0.25 |
| M. abscessus MC 5960 | 4 | Not Done | 0.5 |
| M. abscessus BB1 | 4 | Not Done | 2 |
| M. abscessus MC 5812 | 4 | Not Done | 1 |
| M. abscessus MC 5901 | 4 | Not Done | 1 |
| M. abscessus BB6 | 4 | Not Done | 0.5 |
| M. abscessus BB8 | 4 | Not Done | 0.5 |
| M. abscessus MC 5908 | 4 | Not Done | 1 |
| M. abscessus LT 949 | 4 | Not Done | 1 |

TABLE 6-continued

MIC Values of Selected Compounds

| Strain/Special Condition | Protocol | MIC (μg/ml) Compound 13 | MIC (μg/ml) Compound 23A |
|---|---|---|---|
| M. abscessus BB10 | 4 | Not Done | 0.015 |
| M. abscessus MC 6142 | 4 | Not Done | 0.5 |
| M. abscessus MC 6136 | 4 | Not Done | 0.5 |
| M. abscessus MC 6111 | 4 | Not Done | 0.5 |
| M. abscessus MC 6153 | 4 | Not Done | 1 |
| Mycobacterium avium 103 | 4 | 0.47 | 0.18 |
| M. avium Far | 4 | 0.94 | 0.23 |
| M. avium 3404.4 | 4 | 0.94 | 0.23 |
| M. kansasii 303 | 4 | Not Done | 0.03 |
| M. kansasii 316 | 4 | Not Done | 0.06 |
| M. kansasii 379 | 4 | Not Done | <0.015 |
| M. tuberculosis H37Rv ATCC 25618 | 4 | 0.37 | 0.015 |
| M. tuberculosis Erdman ATCC 35801 | 4 | 0.25 | 0.06 |
| M. tuberculosis Erdman ATCC 35801 | 5 | 0.045 | 0.03 |
| M. tuberculosis Erdman ATCC 35801 with Mouse Serum | 5 | 2 | 0.5 |
| M. abscessus BB2 | 4 | Not Done | 1 |
| M. abscessus MC 6005 | 4 | Not Done | 1 |
| M. abscessus MC 5931 | 4 | Not Done | 0.5 |
| M. abscessus MC 5605 | 4 | Not Done | 1.5 |
| M. abscessus MC 6025 | 4 | Not Done | 0.75 |
| M. abscessus MC 5908 | 4 | Not Done | 1.5 |
| M. abscessus BB3 | 4 | Not Done | 0.5 |
| M. abscessus BB4 | 4 | Not Done | 2 |
| M. abscessus BB5 | 4 | Not Done | 0.5 |
| M. abscessus MC 5922 | 4 | Not Done | 0.25 |
| M. abscessus MC 5960 | 4 | Not Done | 0.5 |
| M. abscessus BB1 | 4 | Not Done | 2 |
| M. abscessus MC 5812 | 4 | Not Done | 1 |
| M. abscessus MC 5901 | 4 | Not Done | 1 |
| M. abscessus BB6 | 4 | Not Done | 0.5 |
| M. abscessus BB8 | 4 | Not Done | 0.5 |
| M. abscessus MC 5908 | 4 | Not Done | 1 |
| M. abscessus LT 949 | 4 | Not Done | 1 |
| M. abscessus BB10 | 4 | Not Done | 0.015 |
| M. abscessus MC 6142 | 4 | Not Done | 0.5 |
| M. abscessus MC 6136 | 4 | Not Done | 0.5 |
| M. abscessus MC 6111 | 4 | Not Done | 0.5 |
| M. abscessus MC 6153 | 4 | Not Done | 1 |

Example 25

Seven-Day Oral (Gavage) Toxicity and Toxicokinetics Study in Rats

The objectives of this study were: 1) to evaluate the potential toxicity of Compound 13 and Compound 23A when administered orally by gavage to male rats for 7 consecutive days and 2) to assess the toxicokinetics of Compound 13, and Compound 23A after the first and seventh doses.

Animals

Species, Source, History, and Justification

Crl:CD(SD) rats were obtained from Charles River Laboratories of Stone Ridge, N.Y. The animals were laboratory bred and experimentally naïve. Rats were chosen because they are a species that is commonly used for nonclinical toxicity evaluations.

Number, Sex, Age, and Body Weight Range

Forty rats (20 noncannulated males and 20 males with jugular vein cannulas) were ordered. From these animals, 15 noncannulated males and 15 cannulated males were used. Animals were as uniform in age as possible. The rats were prepubertal to young adult, approximately 9 weeks of age at initiation of dosing. Their supplier-calculated birth date was retained in the study records. The weight range for the animals at the time of allocation to groups was 218.5-306.3 g.

Study Design

The rats were assigned as shown in the Table 7 below. Animals received the test article or vehicle by oral gavage for 7 consecutive days and were terminated the day following completion of dosing. The first day of dosing was designated as Day 1 of the study. The animals were evaluated for changes in clinical signs, body weight, and other parameters as described below.

TABLE 7

Group Assignment and Dose Levels

| Dose Group | No. Animals (M) Main Study | No. Animals (M) Toxicokinetics | Test Article | Dose Level (mg/kg/day) | Doses per Day | Dose Concentration (mg/mL) | Dose Volume (mL/kg) | Animals for Necropsy (Day 8) |
|---|---|---|---|---|---|---|---|---|
| A | 3 | 0 | Vehicle | 0 | 1 | 0 | 10 | 3 |
| B | 3 | 3 | Compound 13 | 100 | 1 | 10 | 10 | 6 |
| C | 3 | 3 | Compound 13 | 200 | 1 | 20 | 10 | 6 |
| D | 3 | 3 | Compound 23A | 100 | 1 | 10 | 10 | 6 |
| E | 3 | 3 | Compound 23A | 300 | 2 | 30 | 10 | 6 |
| F | 0 | 3 | Vehicle | 0 | 2 | 0 | 10 | 3 |

Route/Dose

The vehicle and test article were administered by oral gavage once daily for 7 consecutive days at a dose volume of 10 mL/kg body weight for Group A and Groups B-D, respectively. The test article and vehicle were administered by oral gavage twice daily, approximately 8 hours apart, for 7 consecutive days at a dose volume of 10 mL/kg body weight for Group E and Group F, respectively. The actual volume administered to each animal was calculated and adjusted based on the most recent body weight of each animal.

In-Life Observations and Measurements

Observations

Animals were observed for viability at least once in the morning and once in the afternoon, at least 4 hours apart, throughout the study. During the treatment period, daily cageside observations were made and recorded predose and postdose (following the first dose only). The postdosing observations made during treatment occurred at the following times based on $C_{max}/T_{max}$ for the two compounds from previous studies:

1 hour postdose for Groups A-F.

One cageside observation was made on the day of necropsy.

Unscheduled Observations

Any findings observed at times other than scheduled observation times were to be recorded on an unscheduled observation or in Provantis; however, no abnormalities were observed throughout the study. Provantis is an electronic data collection, management and reporting system that is commonly used in the art.

Body Weights

Prior to start of dosing, body weights were measured for randomization on Day 1. During the treatment, body weights were measured on Day 1 and Day 7. In addition, fasted body weights were measured prior to necropsy for calculation of organ/body weight ratios.

Food Consumption

Throughout the study, food consumption was measured daily starting 3 days prior to start of dosing.

Clinical Pathology Evaluation

Blood samples for evaluation of hematology, coagulation, and serum chemistry parameters were collected from all animals from the retro-orbital plexus (under $CO_2/O_2$ anesthesia, for the main study animals) or jugular vein cannula (for the toxicokinetic animals) prior to necropsy. Due to residual heparin used to keep the cannulas patent for the toxicokinetic animals, coagulation samples from these rats, were not able to be analyzed. The animals were fasted overnight prior to blood collection. On the day of blood collection for clinical pathology analyses, the animals were not necropsied until after the blood was collected and the samples judged to be acceptable by the clinical pathology group.

Hematology

An appropriate amount of blood was collected in EDTA-containing tubes. The whole blood samples were analyzed for the parameters indicated below in Table 8.

TABLE 8

| Whole Blood Parameters | |
| --- | --- |
| Red blood cells (RBC) (count and morphology) | Mean corpuscular volume (MCV) |
| White blood cells (WBC) (total and differential) | Mean corpuscular hemoglobin (MCH) |
| Hemoglobin concentration (HGB) | Mean corpuscular hemoglobin concentration (MCHC) |

TABLE 8-continued

| Whole Blood Parameters | |
| --- | --- |
| Hematocrit (HCT) | Platelet count (PLAT) |
| Reticulocyte count (ABSRET) | Mean platelet volume (MPV) |

Coagulation

An appropriate amount of blood was collected in tubes containing sodium citrate and then centrifuged to obtain plasma for the determination of prothrombin time (PT) and activated partial thromboplastin time (APTT).

Serum Chemistry

An appropriate amount of blood was collected in tubes without anticoagulant. The sample was allowed to clot and then was centrifuged to obtain serum. The serum was analyzed for the parameters indicated below in Table 9.

TABLE 9

| Serum Parameters | |
| --- | --- |
| Sodium (NA) | Calcium (CA) |
| Potassium (K) | Inorganic phosphorus (PHOS) |
| Chloride (CL) | Glucose (GLU) |
| Total bilirubin (TBILI) | Urea nitrogen (BUN) |
| Alkaline phosphatase (ALKP) | Total protein (TPRO) |
| Lactate dehydrogenase (LDH) | Albumin (ALB) |
| Aspartate aminotransferase (AST) | Globulin (GLOB) |
| Alanine aminotransferase (ALT) | Albumin/globulin ratio (A/G) |
| Gamma-glutamyltransferase (GGT) | Cholesterol (CHOL) |
| Creatine phosphokinase (CK) | Triglycerides (TRIG) |
| Creatinine (CREA) | |

Toxicokinetics

On the $1^{st}$ and $7^{th}$ day of dosing, blood samples (approximately 0.5 mL/sample) were collected from the jugular vein cannula for all toxicokinetic animals at the timepoints listed below into $K_3$EDTA-containing tubes. Toxicokinetic animals from the control group (Group F) only had a single blood collection sampling from each collection day at the 1-hour timepoint (following the first dose administration of the day). Prior to each collection, a small sample of blood (with heparin blocking solution) was removed from the cannula and discarded. A new syringe was placed on the cannula, and the protocol-required sample was taken. The syringe with the blood sample was removed, and a new syringe with saline attached to the cannula. Blood volume was replaced with an equal volume of saline and then blocking solution placed in the cannula. Each animal was returned to its cage until the next collection timepoint.

All samples collected during this study were placed in labeled containers. Each label contained the following information: 1) Study number, 2) Animal number, 3) collection interval, 4) Group and Sex, and 5) Date of collection.

The blood samples were mixed immediately by inverting, then placed on wet ice and centrifuged cold (~1500 g, ~10 minutes, ~5° C.) to obtain plasma. The plasma was split into 96-well 1.4-mL polypropylene tubes with pierceable TPE capcluster certified RNase, DNase free caps as 2 aliquots and stored frozen ($\leq$−70° C.).

TABLE 10

Sample Collection Timepoints

| Timepoint | Window[1] |
|---|---|
| Predose | Predose |
| 1 h | ±4 min |
| 2 h[2] | ±5 min |
| 4 h | ±5 min |
| 8 h[3] | ±5 min |
| 12 h | ±10 min |
| 24 h | ±20 min |
| 48 h[4] | ±40 min |

[1]All samples were collected within the collection window.
[2]Following Day 1 dosing only.
[3]Obtained from Groups E and F prior to PM dose administration.
[4]Following Day 7 dosing only.

Termination

No animal was deemed moribund during the study. All study animals were euthanized and subjected to a necropsy following the protocol-prescribed number of days of treatment. All animals were terminated by exsanguination (severing the abdominal aorta while under deep $CO_2/O_2$ anesthesia).

Necropsy

A necropsy with tissue collection was conducted on all animals terminated during the study. The necropsy included examination of:
carcass and muscular/skeletal system; all external surfaces and orifices;
cranial cavity and external surface of the brain;
neck with associated organs and tissues; and
thoracic, abdominal, and pelvic cavities with their associated organs and tissues.

All abnormalities were described and recorded.

Organ Weights

For all animals euthanized at scheduled necropsies, the kidneys, liver, and prostate gland were weighed. Following weighing, an approximate 1 gram sample of liver and kidney was weighed, transferred to Precellys 7 mL CK28 Tissue Homogenizing tubes (Cat. No. 0904-01), snap-frozen, and analyzed.

Organ/body ratios were calculated using the terminal fasted body weight obtained prior to necropsy.

Tissue Preservation and Bone Marrow Collection

The tissues and organs indicated below in Table 11 were collected from all animals and were preserved in 10% neutral-buffered formalin with the exception of the testes, epididymides, and eyes. Testes, epididymides, and eyes with optic nerve attached were fixed in Modified Davidson's Solution for ~24-48 hours, rinsed with water, and then transferred to 10% neutral-buffered formalin for storage.

TABLE 11

Tissue Collection

| Tissue | Submitted at Necropsy | Organ Weight | Histopathology |
|---|---|---|---|
| Animal ID | X | | |
| Adrenal gland (2) | X | | |
| Aorta | X | | |
| Artery, mesenteric | X | | |
| Bone (femur) | X | | |
| Bone marrow (sternum) | X | | |
| Brain | X | | |
| Epididymides (2) | X | | |
| Esophagus | X | | |
| Eyes (2) | X | | |
| Gross lesions | X | | |
| Heart | X | | |
| Intestine, cecum | X | | |
| Intestine, colon | X | | |
| Intestine, duodenum | X | | |
| Intestine, jejunum | X | | |
| Intestine, ileum | X | | |
| Intestine, rectum | X | | |
| Kidneys (2) | X | X | X |
| Liver | X | X | X |
| Lungs | X | | |
| Lymph node, mandibular | X | | |
| Lymph node, mesenteric | X | | |
| Mammary gland | X | | |
| Nerve, optic | X | | |
| Nerve, sciatic | X | | |
| Parathyroid gland (2)[a] | X | | |
| Pancreas | X | | |
| Pituitary | X | | |
| Prostate | X | X | X |
| Seminal vesicles | X | | |
| Skeletal muscle (biceps femoris) | X | | |
| Skin (abdominal) | X | | |
| Spinal cord, cervical | X | | |
| Spinal cord, thoracic | X | | |
| Spinal cord, lumbar | X | | |
| Spleen | X | | |
| Stomach | X | | |
| Testes (2) | X | | |
| Thymus | X | | |
| Thyroid gland (2)[a] | X | | |
| Tongue | X | | |
| Trachea | X | | |
| Urinary bladder | X | | |

[a]Thyroid weighed with parathyroids attached.

Histopathology

For all animals scheduled for the terminal necropsy, the kidneys, liver, and prostate were embedded in paraffin, sectioned and stained with hematoxylin and eosin for further examination by light microscopy. For Groups A, D, E, and F only, the remaining tissues listed above were embedded in paraffin, sectioned and stained with hematoxylin and eosin for further examination by light microscopy.

Statistical Analysis

Where appropriate, numeric animal data were evaluated statistically.

For comparative statistics, Group A (control group) was compared to Groups B and C (treated groups, dosed QD) and Group F (control group, dosed BID) was compared to Group E (treated group, dosed BID). Data were evaluated using the Levene Test for homogeneity of variances and the Shapiro-Wilks Test for normality of distributions, with significance at $p \leq 0.05$. Data determined to be homogeneous and of normal distribution were evaluated by analysis of variance (ANOVA). If the ANOVA verified significance at $p \leq 0.05$, pairwise comparisons of each treated group with the respective control group were made using a parametric test (Dunnett Test) to identify statistical differences ($p \leq 0.05$). Data determined to be nonhomogeneous or of normormal distribution were evaluated using a Kruskal-Wallis Test for group factor significance. If significance ($p \leq 0.05$) existed between groups, a nonparametric test (Wilcoxonwith Bonferroni-Holm), was used to compare treatment groups to the control group. Food consumption data from animals where spillage occurred was excluded from the applicable time period. Comparative statistics of food consumption data were limited to the Dunnett Test (parametric). Statistics were not performed on pretest food consumption (Day 4 to Day 1).

Results

The exposures for different dosage levels of Compound 23A and Compound 13 were dose related. No adverse observations or effects on mean body weight were observed in animals treated with either Compound 13 or Compound 23A. Mean food consumption was reduced during different intervals of the study for animals treated once daily with Compound 13 (100 or 200 mg/kg) and twice daily with Compound 23A (300 mg/kg). However, as the decreased food consumption was not correlated with body weight changes in the Compound 13 and Compound 23A groups, these effects were not considered to be adverse or biologically significant. The mean calcium ion concentration (CA) was statistically lower, while the mean ALT and the AST for the group of rats administered 300 mg/kg Compound 23A twice a day were statistically higher when compared to the controls treated twice a day. No test article-related histopathological findings were noted for animals receiving either Compound 13 or Compound 23A at any dose regimen.

Within the scope of this study and based on the absence of changes in body weight, clinical pathology, and histopathology, the NOEL (No-Observable-Effect-Level) for Compound 13 administered to male rats once a day for 7 days orally via gavage was 200 mg/kg (844 µg*hr/ml Day 7 AUC), while the NOEL for Compound 23A administered once a day was 100 mg/kg (82 µg*hr/ml AUC). The NOAEL (No-Observable-Adverse-Effect-Level) for Compound 23A administered to male rats twice a day for 7 days orally via gavage was 300 mg/kg (291 µg*hr/ml AUC).

Therefore, Compounds 13 and 23A did not demonstrate adverse toxicity within the scope of the study at dose levels up to 200 mg/kg/day and 600 mg/kg/day, respectively.

Example 26

An Oral Range Finding Toxicity and Toxicokinetic Study in Male Cynomolgus Monkeys The objectives of this study were 1) to evaluate the potential toxicity of Compound 23 when administered orally by gavage to male Cynomolgus monkeys for 7 consecutive days; and 2) to assess the toxicokinetics of Compound 23 after the first and seventh doses.

Animals

Species, Source, History, and Justification

Cynomolgus monkeys (*Macaca Fascicularis*) were obtained from Primus Bio-Resources Inc. of PinCourt, Quebec, Canada. Cynomolgus monkeys were chosen because they are a non-rodent species that is commonly used for nonclinical toxicity evaluations.

Number, Sex, Age, and Body Weight Range

Eight (2 naive and 6 non-naïve) males were used in the study. The animals were young adults and weighed between 2 to 4 kg at the onset of dosing.

Study Design

The animals were assigned as shown in Table 12 below. Animals received Compound 23 or vehicle by oral gavage once per day for 7 consecutive days and were terminated the day following completion of dosing. The first day of dosing was designated as Day 1 of the study. The actual volume administered to each animal was calculated and adjusted based on the most recent body weight of each animal.

TABLE 12

| Group Assignment and Dose Levels | | | | |
|---|---|---|---|---|
| Group | Dose Level (mg/kg) | Dose Concentration (mg/mL) | Dose Volume (mL/kg) | Number of animals |
| 1 | Control* | 0 | 5 | 2 |
| 2 | 50 | 10 | 5 | 2 |
| 3 | 100 | 20 | 5 | 2 |
| 4 | 200 | 40 | 5 | 2 |

*The Control animals received the control/vehicle (20% captisol/1% HPMCAS/1% PVP in 0.01M KCl/HCL buffer) alone In-Life Observations and Measurements Observations Cage-side clinical signs (ill health, behavioral changes etc.) were recorded at least once daily during the study.

Body Weights

Body weights were recorded for all animals prior to group assignment and on Days 1 (prior to dosing), 3 and 7 as well as terminally prior to necropsy (fasted).

Electrocardiography (ECG)

Electrocardiograms (bipolar limb leads I, II and III, and augmented unipolar leads aVR, aVL and aVF) were obtained for all monkeys once during the pre-treatment period and again on Day 7 (post-dosing).

The tracings were assessed for gross changes indicative of cardiac electrical dysfunction. The potential presence of abnormalities involving heart rate (lead II), sinus and atrioventricular rhythm or conductivity were determined. Heart rate, PR interval, QRS duration, QT and QTc intervals values were measured.

Toxicokinetics

A series of 7 blood samples (approximately 0.5 mL each) were collected from each monkey on Days 1 and 7 at the following time points: predose, 30 minutes and 2, 3, 6, 12 and 24 hours post-dose. For this purpose, each monkey was bled by venipuncture and the samples were collected into tubes containing the anticoagulant, K2EDTA. Tubes were placed on wet ice until ready for processing.

Clinical Pathology

Laboratory investigations (hematology, coagulation, clinical chemistry and urinalysis) were performed on all animals prior to start of treatment and prior to termination on Day 8.

Blood samples were collected by venipuncture following an overnight period of food deprivation consisting of at least 12 hours but no more than 20 hours. Urine was collected from animals deprived of food and water, overnight (at least 12 hours but no more than 20 hours).

Hematology

The following parameters were measured on blood samples collected into EDTA anticoagulant: red blood cell count, mean corpuscular hemoglobin (calculated), hematocrit (calculated), mean corpuscular volume, hemoglobin, morphology of cells, white blood cell count, platelet count, white blood cell differential (absolute), reticulocyte (absolute and percentage) and mean corpuscular hemoglobin concentration (calculated).

Coagulation

Activated partial thromboplastin time and prothrombin time were measured on blood samples collected into citrate anticoagulant.

Clinical Chemistry

The following parameters were measured on blood samples collected into tubes containing clotting activator: a/g ratio (calculated), creatinine, alanine aminotransferase, globulin (calculated), albumin, glucose, alkaline phosphatase, phosphorus (inorganic), aspartate aminotransferase, potassium, bilirubin (total), sodium, calcium, total protein, chloride, triglycerides, cholesterol (total), urea, gamma glutamyltransferase and sorbitol dehydrogenase.

Urinalysis

The following parameters were measured on urine samples: bilirubin, protein, blood, sediment microscopy, color and appearance, specific gravity, glucose, urobilinogen, ketones, volume and pH.

Termination

All animals were euthanized upon completion of the treatment period on Day 8 following an overnight period without food. The monkeys were pre-anesthetized with Ketamine and then euthanized by an intravenous overdose of sodium pentobarbital followed by exsanguination by transsection of major blood vessels.

Necropsy

A necropsy with tissue collection was conducted on all animals terminated during the study. The necropsy included examination of:

carcass and muscular/skeletal system;
all external surfaces and orifices;
cranial cavity and external surface of the brain;
neck with associated organs and tissues; and
thoracic, abdominal, and pelvic cavities with their associated organs and tissues.

All abnormalities were described and recorded.

Tissue Preservation

On completion of the gross examination and selected organ weighing, the tissues and organs were retained as noted below in Table 13. Neutral buffered 10% formalin was used for fixation and preservation unless otherwise indicated.

TABLE 13

Tissue and Organ Retention

|  | Retain(•) | Weigh (√) | Examine (€) |
|---|---|---|---|
| Adrenals | • | √ | € |
| Animal identification | • | | |
| Aorta (thoracic) | • | | € |
| Blood | | | |
| Bone marrow smears (3) | • | | |
| Brain | • | √ | € |
| Cecum | • | | € |
| Colon | • | | € |
| Epididymides | •d | | € |
| Esophagus | • | | € |
| Eyes | •a | | € |
| Femur & marrow | • | | € |
| Gallbladder | • | | € |
| Heart | • | √ | € |
| Kidneys | • | √ | € |
| Liver (2 lobes) | • | √ | € |
| Lungs (2 lobes) | •b | √c | € |
| Lymph Node, mandibular | • | | € |
| Lymph Node, mesenteric | • | | € |
| Mammary gland (thoracic) | • | | € |
| Optic nerves | •a | | € |
| Pancreas | • | | € |
| Pituitary | • | √ | € |
| Prostate | • | √ | € |
| Rectum | • | | € |
| Salivary Gland, mandibular | • | | € |
| Sciatic nerve | • | | € |
| Seminal vesicles | • | | € |
| Skeletal muscle | • | | € |
| Skin & subcutis (thoracic) | • | | € |
| Duodenum | • | | € |
| Jejunum | • | | € |
| Ileum | • | | € |
| Spinal Cord, cervical | • | | € |

TABLE 13-continued

Tissue and Organ Retention

|  | Retain(•) | Weigh (√) | Examine (€) |
|---|---|---|---|
| Spleen | • | √ | € |
| Sternum & marrow | • | | € |
| Stomach | • | | € |
| Testes | •d | √ | € |
| Thymus | • | √ | € |
| Thyroid gland/parathyroids | • | √ | € |
| Tongue | • | | € |
| Trachea | •c | | € |
| Urinary bladder | • | | € |
| Abnormal findings | • | | | aDavidson's fluid used for fixation and preservation
bLungs were infused with 10% neutral buffered formalin used for fixation and preservation
cLungs were weighed with trachea
dBouin's fluid used for fixation and preservation
€Examined microscopically Histopathology For all animals, all tissues indicated above were embedded in paraffin, sectioned and stained with hematoxylin and eosin and examined by light microscopy.

Results

The exposures for different dosage levels of Compound 23 were dose related.

There were no clinical signs, or changes in body weights, electrocardiography parameters, clinical pathology parameters, or organ weights that could be attributed to the administration of Compound 23 at doses up to 200 mg/kg/day. Similarly, there were no macroscopic or microscopic findings that could clearly be attributed to the administration of Compound 23 at doses up to 200 mg/kg/day. The no observed effect level (NOEL) for Compound 23 in male Cynomolgus monkeys was determined to be 200 mg/kg/day.

Example 27

Pharmacokinetic Studies

The pharmacokinetic parameters of selected compounds of this invention were determined in the experiments described below. General analytic procedures and specific experimental protocols were employed as follows:

General Analytic Procedures

The following general analytic procedures were employed in the pharmacokinetic experiments described below:

Sample Analysis.

Concentrations of Compound 23 and Compound W in plasma were determined using a high performance liquid chromatography/tandem mass spectrometry (HPLC/MS/MS) method. Before extraction, plasma samples were diluted using blank plasma 2-, 4-, 5-, or 10-fold, as necessary, depending on the dose level or formulation. Compound 23 and Compound W along with the internal standard (IS) were extracted from (diluted) plasma, 100 µL each, by direct protein precipitation with acetonitrile (1:4 ratio of plasma/acetonitrile). After centrifugation, the supernatant extract (10 µL) was injected onto the LC/MS/MS system. The HPLC system included a Waters Xterra MS C18 column, 5 micron, 2.1 mm diameter×50 mm long eluted with a gradient mobile phase consisting of 0.1% formic acid in water or in acetonitrile.

The analytes were detected by MS/MS with Atmospheric Pressure Chemical Ionization (APCI) in the mode of multiple reaction monitoring (MRM). The lower limit of quantitation (LLOQ) was 1, 2, 4, 5, 10, or 20 ng/mL, depending on the sample dilution factor. The linear range of the assay was from 1 to 5000 ng/mL. The intra-day and inter-day assay accuracy was within 2% of the nominal values. The intra- and inter-day assay variability was <10%.

Samples of the dose suspension formulation of Compound W were assayed with an HPLC/UV method after 10-fold to 500- or 1000-fold of dilution with DMSO:acetonitrile:water (33:33:33) depending on the dose level or formulation. Samples of the dose solution formulation of Compound W were assayed with an HPLC/UV method after 10-, 50-, 100 or 500-fold of dilution with DMSO:water (50:50) depending on the dose level or formulation.

Plasma samples were analyzed using a liquid chromatography/tandem mass spectrometry (LC/MS/MS) method to determine the concentrations of Compound 23 and Compound W with a lower limit of quantitation (LLOQ) of 1 to 20 ng/mL, depending on the sample dilution factor. Plasma concentration vs. time data was subjected to noncompartmental pharmacokinetic (PK) analysis. The results of this analysis are provided in Table 14.

TABLE 14

Pharmacokinetic Data from Monkey Oral Study

| Dose (mg/kg) | Route | Formulation | Analyte | Cmax (ug/ml) | AUC (ug * hr/ml) | AUCextrap (ug * hr/ml) | Tmax (hr) | t1/2 (hr) |
| --- | --- | --- | --- | --- | --- | --- | --- | --- |
| 30 | PO | 0.5% MC | Compound 23 | 14.4 | 24.7 | 24.8 | 1.7 | 13.9 |
| 100 | PO | 0.5% MC | Compound 23 | 20.9 | 76.7 | 76.9 | 2.3 | 8.3 |
| 300 | PO | 0.5% MC | Compound 23 | 23.8 | 155.1 | 155 | 1.2 | 5.6 |
| 30 | PO | 0.5% MC | Compound W | 0.0264 | 0.0453 | 0.206 | 0.83 | — |
| 100 | PO | 0.5% MC | Compound W | 0.322 | 0.432 | 0.437 | 0.67 | 5.31 |
| 300 | PO | 0.5% MC | Compound-W | 4 | 3.69 | 3.76 | 0.58 | 13.15 |

Pharmacokinetic Data Analysis.

Plasma concentration-time profiles of Compound 23 and Compound W were analyzed by noncompartmental pharmacokinetic methods using WinNonlin® Professional Edition software, Version 5.1.1 (Pharsight Corporation, Mountain View, Calif.).

Key pharmacokinetic parameters including $AUC_{all}$, $AUC_{extrap}$, $C_{max}$, $t_{max}$, Cl_obs, Vss_obs and $t_{1/2}$ were determined.

Statistical Data Analysis.

Descriptive statistical data of plasma concentrations and pharmacokinetic parameter estimates were calculated, including the mean, standard deviation (SD), and coefficient of variation (% CV) using WinNonlin software, Version 5.1.1 or Microsoft Excel 2000.

Monkey Oral Study

Malecynomolgus monkeys (n=3 per dose group) were administered single nominal PO doses of 3, 30 and 300 mg/kg of Compound W by gavage. Compound W was formulated in 0.5% MC (microcrystalline cellulose). Animals had free access to food and water before and after dosing.

Blood samples (approximately 0.25 mL each) were collected via a carotid artery catheter prior to dosing and at 0 (predose), 0.25, 0.5, 1, 2, 3, 4, 6, 8, 12, 24, 48 hours post dose. Each blood sample was collected into a tube that was kept on wet ice and contained potassium EDTA as the anticoagulant. Plasma was separated and stored at approximately −70° C. until analysis.

Monkey IV Study

Male cynomolgus monkeys (n=3 per dose group) were administered a single nominal IV bolus dose of 1 mg/kg of Compound W via a jugular vein cannula. Compound W was formulated in D5W (5% dextrose in water solution). Animals had free access to food and water before and after dosing.

Blood samples (approximately 0.25 mL each) were collected via a carotid artery catheter prior to dosing and at 0 (predose), 5 min, 10 min, 0.25, 0.5, 1, 2, 3, 4, 6, 8, 12, 24, 48 hours postdose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of Compound 23 and Compound W, with a lower limit of quantitation (LLOQ) of 1 to 20 ng/mL, depending on the sample dilution factor. Plasma concentration vs. time data were subjected to noncompartmental pharmacokinetic (PK) analysis. The results of this analysis are provided in Table 15.

TABLE 15

Pharmacokinetic Data from Monkey IV Study

| Dose (mg/kg) | Route | Formulation | Analyte | C0 (ug/ml) | AUC (ug * hr/ml) | AUCextrap (ug * hr/ml) | Cl (ml/min/kg) | t1/2 (hr) | Vss (L/kg) |
| --- | --- | --- | --- | --- | --- | --- | --- | --- | --- |
| 5 | IV | D5W | Compound 23 | 10.9 | 3.78 | 3.81 | 23.4 | 6.17 | 2.09 |
| 5 | IV | D5W | Compound W | 62.4 | 5.79 | 5.83 | 18.2 | 5.35 | 1.88 |

Rat Oral Study

Groups of male Sprague Dawley rats (n=3 per dose group) were administered single nominal oral doses of 3, 10, 30, 300 mg/kg of Compound W by gavage. Compound W was formulated in either 0.5% MC (microcrystalline cellulose) or 20% Captisol, 1% HPMC-AS (hydroxypropyl methylcellulose acetyl succinate), 1% PVP (polyvinylpyrrolidone). Animals had free access to food and water before and after dosing. Blood samples (approximately 0.25 mL each) were collected via a carotid artery catheter prior to dosing and at 0 (predose), 0.25, 0.5, 1, 1.5, 2, 4, 6, 8, 12, 24 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of Compound 23 and Compound W with a lower limit of quantitation (LLOQ) of 1 to 20 ng/mL, depending on the sample dilution factor. Plasma concentration vs. time data was subjected to noncompartmental pharmacokinetic (PK) analysis. The results of this analysis are provided in Table 16.

TABLE 16

Pharmacokinetic Data from Rat Oral Study

| Dose (mg/kg) | Formulation | Analyte | Cmax/C0 (ug/ml) | AUC (ug * hr/ml) | AUCextrap (ug * hr/ml) | Tmax (hr) | t1/2 (hr) |
|---|---|---|---|---|---|---|---|
| 3 | 0.5% MC | Compound 23 | 0.117 | 0.311 | 0.314 | 0.58 | 4.06 |
| 30 | 0.5% MC | Compound 23 | 2.9 | 22.5 | 22.6 | 1.7 | 2.6 |
| 100 | 0.5% MC | Compound 23 | 6.6 | 77.1 | 77.4 | 2.5 | 2.7 |
| 300 | 0.5% MC | Compound 23 | 11.7 | 222.8 | 307.6 | — | 17.9 |
| 300 | 20% CAPT, 1% HPMC-AS, 1% PVP | Compound 23 | 16.2 | 294.6 | — | 5 | — |
| 3 | 0.5% MC | Compound W | — | — | — | — | — |
| 30 | 0.5% MC | Compound W | 0.022 | 0.178 | 0.058 | 3.3 | 3.1 |
| 100 | 0.5% MC | Compound W | 0.021 | 0.061 | 0.066 | 0.8 | 7.2 |
| 300 | 0.5% MC | Compound W | 2.33 | 0.324 | 0.464 | 1.2 | 11.3 |
| 300 | 20% CAPT, 1% HPMC-AS, 1% PVP | Compound W | 0.6 | 2.37 | 4.27 | 1.8 | — |

Rat IV Study

Groups of male Sprague Dawley rats (n=3 per dose group) were administered single nominal IV bolus doses of 1 and 5 mg/kg of Compound W via a jugular vein cannula. Compound W was formulated in D5W. Animals had free access to food and water before and after dosing. Blood samples (approximately 0.25 mL each) were collected via a carotid artery catheter prior to dosing and at 0 (predose), 5 min, 10 min, 0.25, 0.5, 1, 1.5, 2, 4, 6, 8, 12, 24 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of Compound 23 and Compound W with a lower limit of quantitation (LLOQ) of 1 to 20 ng/mL, depending on the sample dilution factor. Plasma concentration vs. time data were subjected to noncompartmental pharmacokinetic (PK) analysis. The results of this analysis are provided in Table 17.

TABLE 17

Pharmacokinetic Data from Rat IV Study

| Dose (mg/kg) | Formulation | Analyte | Cmax/C0 (ug/ml) | AUC (ug * hr/ml) | AUCextrap (ug * hr/ml) | t1/2 (hr) | Cl_obs (ml/min/kg) | Vss_obs (L/kg) |
|---|---|---|---|---|---|---|---|---|
| 1 | D5W | Compound 23 | 0.247 | 0.306 | 0.31 | 1.8 | 54.9 | 3.8 |
| 5 | D5W | Compound 23 | 1.2 | 3.04 | 3.06 | 3.6 | 27.3 | 4.08 |

TABLE 17-continued

Pharmacokinetic Data from Rat IV Study

| Dose (mg/kg) | Formulation | Analyte | Cmax/C0 (ug/ml) | AUC (ug * hr/ml) | AUCextrap (ug * hr/ml) | t1/2 (hr) | Cl_obs (ml/min/kg) | Vss_obs (L/kg) |
|---|---|---|---|---|---|---|---|---|
| 1 | D5W | Compound W | 4.8 | 0.416 | 0.419 | 0.9 | 46.7 | 0.38 |
| 5 | D5W | Compound W | 9.03 | 1.11 | 1.12 | 7.2 | 84.6 | 5.8 |

Mouse Oral Study

Groups of female CD-1 mice (n=3 per dose group) were administered single nominal oral doses of 10, 30, 100 mg/kg of Compound W by gavage. Compound W was formulated in 0.5% MC. Animals had free access to food and water before and after dosing. Blood samples (approximately 0.025 mL each) were collected from the sub-mandibular vein prior to dosing and at 0 (predose), 0.25, 0.5, 1, 1.5, 2, 4, 6, 8, 12, 24 hours postdose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method with a lower limit of quantitation (LLOQ) of 1 to 20 ng/mL, depending on the sample dilution factor. Plasma concentration vs. time data was subjected to noncompartmental pharmacokinetic (PK) analysis. The results of this analysis are provided in Table 18.

TABLE 18

Pharmacokinetic Data from Mouse Oral Study

| Dose (mg/kg) | Formulation | AUC (0-t) (µg*hr/mL) | Cmax (µg*hr/ml) | Tmax (hr) |
|---|---|---|---|---|
| 10 | 0.5% MC | 1.7 | 1.2 | 0.3 |
| 30 | 0.5% MC | 4.1 | 2.1 | 0.3 |
| 100 | 0.5% MC | 26.6 | 9.1 | 0.4 |

The studies described above, demonstrate that Compound W is converted in vivo into Compound 23 in at least rats, dogs and monkeys.

Example 28

Enzymology Studies

The enzyme inhibition activities of selected compounds of this invention were determined in the experiments described below:

DNA Gyrase ATPase Assay

The ATP hydrolysis activity of S. aureus DNA gyrase was measured by coupling the production of ADP through pyruvate kinase/lactate dehydrogenase to the oxidation of NADH. This method has been described previously (Tamura and Gellert, 1990, *J. Biol. Chem.*, 265, 21342).

ATPase assays were carried out at 30° C. in buffered solutions containing 100 mM TRIS pH 7.6, 1.5 mM $MgCl_2$, 150 mM KCl. The coupling system contains final concentrations of 2.5 mM phosphoenol pyruvate, 200 µM nicotinamide adenine dinucleotide (NADH), 1 mM DTT, 30 ug/ml pyruvate kinase, and 10 ug/ml lactate dehydrogenase. The enzyme (90 nM final concentration) and a DMSO solution (3% final concentration) of the selected compound were added. The reaction mixture was allowed to incubate for 10 minutes at 30° C. The reaction was initiated by the addition of ATP to a final concentration of 0.9 mM, and the rate of NADH disappearance was monitored at 340 nanometers over the course of 10 minutes. The $K_i$ and $IC_{50}$ values were determined from rate versus concentration profiles.

Selected compounds of the present invention were found to inhibit S. aureus DNA gyrase. Table 19 shows the inhibitory activity of these compounds in the S. aureus DNA gyrase inhibition assay.

TABLE 19

Inhibition of S. aureus DNA Gyrase

| Selected Compound | $K_i$ (nM) | $IC_{50}$ (nM) |
|---|---|---|
| Compound 23 | 9 | |
| Compound W | <9 | 54 |

DNA Topo IV ATPase Assay

The conversion of ATP to ADP by S. aureus TopoIV enzyme was coupled to the conversion of NADH to NAD+, and the progress of the reaction was measured by the change in absorbance at 340 nm. TopoIV (64 nM) was incubated with the selected compound (3% DMSO final) in buffer for 10 minutes at 30° C. The buffer consisted of 100 mM Tris 7.5, 1.5 mM $MgCl_2$, 200 mM K·Glutamate, 2.5 mM phosphoenol pyruvate, 0.2 mM NADH, 1 mM DTT, 5 ng/mL linearized DNA, 50 ng/mL BSA, 30 ng/mL pyruvate kinase, and 10 ng/mL lactate dehyrodgenase (LDH). The reaction was initiated with ATP, and rates were monitored continuously for 20 minutes at 30° C. on a Molecular Devices SpectraMAX plate reader. The inhibition constant, Ki, and the $IC_{50}$ were determined from plots of rate vs. concentration of selected compound fit to the Morrison Equation for tight binding inhibitors.

Selected compounds of the present invention were found to inhibit S. aureus DNA Topo IV. Table 20 shows the inhibitory activity of these compounds in the S. aureus DNA gyrase inhibition assay.

TABLE 20

Inhibition of S. aureus DNA Topo IV

| Selected Compound | $K_i$ (nM) | $IC_{50}$ (nM) |
|---|---|---|
| Compound 23 | 12 | |
| Compound W | 30 | 150 |

Example 29

Aqueous Solubility Study

The aqueous solubilities of compound 23 and compound W were determined according to the following procedure.

Preparation of Samples.

Aqueous samples of each compound were prepared as follows. Compounds were weighed (20-30 mg compound) in 4 ml clear vials prior to adding water (0.5 mL) and stirring by magnetic stirrer. 1.0N HCl was added to the suspension to adjust the pH to the desired range. After stirring for 96 hours at room temperature, the suspension was filtered through a 0.22 micron filter (Millipore, Ultrafree centrifugal filters, Durapore PVDF 0.22 µm, Cat# UFC30GVNB). The filtrate was collected and the pH measured with a pH meter. The filtrate containing compound W was diluted 10-fold to provide an appropriate concentration for HPLC analysis. The filtrate containing compound 23 did not require dilution.

Preparation of Standard Solutions.

Standard solutions of each compound were prepared according to the following procedure. 1 to 2 mg of each compound was accurately weighed into a 10 mL volumetric flask and either water (for compound W) or 1:1 methanol: 0.1N HCl (for compound 23) was added to completely dissolve the compounds. Sonication was performed for compound 23 to assist with the dissolution in 1:1 methanol:0.1N HCl. When all solids dissolved, additional solvent was added to adjust the volume of each solution to 10 ml. The resulting solutions were thoroughly mixed to give the standard solutions of each compound. Each standard solution was then diluted with solvent by 2-fold, 10-fold, and 100-fold.

Solubility Analysis.

Aliquots of each sample and each standard solution were analyzed by HPLC analysis (Agilent 1100, injection volume 10 µL, wavelength 271 nm, column XTerra® Phenyl 5 µm, 4.6×50 mm, Part No. 186001144, mobile phase: A: 0.1% TFA in water 0.1% TFA in AcN). Each standard solution was injected three times, and each of the samples was injected twice. Standard curves were obtained by plotting the average of the peak area from the HPLC versus the concentrations of the standard solutions (with appropriate corrections of the weights of the standards based on total water content of the solid as determined by elemental analysis). The concentration of each sample was calculated from the peak area of the aqueous sample from the HPLC results and the slope and intercept of the standard curves. The solubility values listed in Table 21 below were derived from the product of the concentration of the sample and the dilution factor of the sample.

TABLE 21

Aqueous Solubility of Compounds 23 and W

| Compound | Solid form | pH | Solubility (mg/mL) |
|---|---|---|---|
| Compound 23 | crystalline | >3.0 | <0.001 |
| Compound W | crystalline | 4.39 | 0.25 |

Example 30

In Vivo Metabolism Study in Hepatic and Liver S9 Cells

The conversion of Compound W to Compound 23 was studied in liver and intestinal S9 fractions from rats, dogs, monkeys and humans. Compound W was incubated at 0.1, 0.3, 1, 3, 10, 20, 40, 100, 200, 300 µM in liver S9 fractions and at 1, 3, 10, 20, 100, 300, 500, 1000 µM in intestinal S9 fractions. The incubations were done for 0, 5, 10, 15, 30, 45 or 60 minutes. The formation of Compound 23 was quantified by LC/MS-MS and data were fitted to the Michaelis Menten equation. The data in Table 22 below indicates that Compound W rapidly converts to Compound 23 in these hepatic and intestinal S9 fractions.

TABLE 22

Velocity of formation ($V_{MAX}$) of Compound 23 from Compound W in Liver and Intestinal S9

| | $V_{MAX}$ (liver) (pmoles/min/mg) | $V_{MAX}$ (intestine) (pmoles/min/mg) |
|---|---|---|
| Dog | 19.3 | 1162 |
| Monkey | 25.2 | 1974 |
| Rat | 45.5 | 958 |
| Human | 45.8 | ND* |

*ND: Parameters not determined, rate of formation did not saturate

Example 30

Mouse *M. tuberculosis* (Erdman) Lung Infection Model

Animals: female Balb/c mice (5-7 weeks of age; 6/group) were obtained from Jackson Laboratories (Bar Harbor, Me.) and were housed and maintained in a BSL3 facility in accordance with the Guide to the Care and Use of Experimental Animals.

Bacterial Strain and Stocks

*M. tuberculosis* ATCC 35801 (strain Erdman) was obtained from the ATCC (Manassas, Va., USA). The organism was grown in 20 tubes of modified 7H10 broth (pH 6.6; 7H10 agar formulation with agar and malachite green omitted) with 10% OADC (oleic acid, albumin, dextrose, catalase) enrichment (BBL Microbiology Systems, Cockeysville, Md., USA) and 0.05% Tween 80 for 5-10 days on a rotary shaker at 37° C. The cultures were pooled and diluted to 100 Klett units [equivalent to $5 \times 10^7$ colony forming units (cfu)/mL] (Photoelectric Colorimeter; Manostat Corp., New York, N.Y., USA). The culture was aliquotted and frozen at −70° C. On the day of infection, the culture was thawed and the final inoculum was determined. The final inoculum size was determined by diluting to $5 \times 10^{-2}$ and plating 0.1 mL, in triplicate, on 7H10 agar plates (BBL Microbiology Systems) supplemented with 10% OADC enrichment. The plates were incubated at 37° C. in ambient air for 4 weeks.

Mouse *M. Tuberculosis* (Erdman) Infection Model

For intranasal infection, groups of mice were anaesthetized by intramuscular delivery of a telazol (45 mg/kg)/xylazine (7.5 mg/kg) cocktail (Lederle Parenterals, Carolina, Puerto Rico and Bayer Corp., Shawnee Mission, Kans., USA, respectively) and subsequently infected intranasally with ~$10^2$ viable *M. tuberculosis* in a 20 µL volume. The timetable for the experiment was a follows: on study day 0, intranasal infection and then on study day 24, early controls were sacrificed for lung burden determination and treatment was started. 28 days post initiation of treatment (52 days post infection) all treated mice and late controls were sacrificed for lung burden determination.

For bacterial load determination mice were sacrificed by $CO_2$ asphyxiation. Right lungs were aseptically removed and ground in a sealed tissue homogenizer (IdeaWorks! Laboratory Devices, Syracuse, N.Y., USA). The number of viable organisms was determined by serial dilution and titration on 7H10 agar plates. Plates were incubated at 37° C. in ambient air for 4 weeks prior to counting.

TABLE 23a

Compound 23A Reduces M. Tuberculosis Burdens in the Mouse M. Tuberculosis 28 Day Lung Infection Model

| Treatment Group | Average Lung Burden (Log cfu/lungs) | Log Reduction vs. Early Control | Log Reduction vs. Late Control |
|---|---|---|---|
| Early Control | 4.98 | | |
| Late Control (10 mL/Kg Vehicle) | 5.20 | −0.22 | |
| 10 mg/kg BID Compound 23A | 5.08 | −0.10 | 0.13 |
| 30 mg/kg BID Compound 23A | 4.11 | 0.86 | 1.09 |
| 100 mg/kg BID Compound 23A | 3.22 | 1.76 | 1.98 |
| 100 mg/kg QD Moxifloxacin | 2.94 | 2.04 | 2.26 |

Balb/c mice (6/group) were challenged IN (intranasally) with M. tuberculosis (Erdman; ATCC) at $1\times10^2$ cfu/mouse. After 24 days, a single group of mice (Early Control (EC)) was euthanized and the lungs harvested, homogenized and plated to quantitate M. tuberculosis burdens. The additional groups of infected mice were treated via oral gavage with Vehicle at 10 ml/kg (10% VitE-TPGS; Late Control, LC) or with Compound 23A administered at 10, 30, or 100 mg/kg BID for 28 days. An additional control group was treated with Moxifloxacin administered at 100 mg/kg QD. After 28 days of treatment, the groups were euthanized and the lungs harvested, homogenized and plated to quantitate M. tuberculosis burdens. Burdens from the right lung for each mouse and the median for each group of mice were recorded and summarized above in Table 23a.

Results:

In summary and as shown above in Table 23a, twice daily oral dosing of Compound 23A exhibited in vivo efficacy against an experimentally induced lung M. tuberculosis infection in Balb/c mice. 28 days of treatment with compound 23A at 30 or 100 mg/kg provided reductions in lung burden vs early controls. In addition, Moxifloxacin provided lung burden reduction compared to vehicle treated controls. Compound 23A demonstrated dose-dependent reductions of 0.13, 1.09 and 1.98 log reductions versus vehicle control (Late) when administered at 10, 30, and 100 mg/kg. In addition, doses of 30 and 100 mg/kg of Compound 23A reduced bacterial burdens versus the early control by 0.7-1.5 logs suggesting Compound 23A has bactericidal activity. The potent anti-tuberculosis drug Moxifloxacin at 100 mg/kg QD provided lung burden reduction versus the early and late controls as previously published. The reductions were similar to those provided by Compound 23A administered at 100 mg/kg indicating that compound 23A has bactericidal activity against M. tuberculosis.

TABLE 23b

Compound W Reduces M. Tuberculosis Burdens in the Mouse M. Tuberculosis 28 Day Lung Infection Model

| Treatment Group | Median Lung Burden (Log cfu/lungs) | Log Reduction vs. Early Control | Log Reduction vs. Late Control |
|---|---|---|---|
| Early Control | 4.98 | | |
| Late Control | 4.36 | 0.62 | |
| 10 mg/kg BID Compound W | 4.34 | 0.64 | 0.02 |
| 30 mg/kg BID Compound W | 3.00 | 1.98 | 1.36 |
| 100 mg/kg BID Compound W | 2.35 | 2.63 | 2.01 |
| 100 mg/kg QD Moxifloxacin | 2.94 | 2.04 | 1.42 |

Balb/c mice (6/group) were challenged IN (intranasally) with M. tuberculosis (Erdman; ATCC) at $1\times10^2$ cfu/mouse. After 24 days, a single group of mice (Early Control (EC)) was euthanized and the lungs harvested, homogenized and plated to quantitate M. tuberculosis burdens. The additional groups of infected mice were treated via oral gavage with Vehicle at 10 ml/kg (10% VitE-TPGS; Late Control, LC) or with Compound W administered at 10, 30, or 100 mg/kg BID for 28 days. An additional control group was treated with Moxifloxacin administered at 100 mg/kg QD. After 28 days of treatment the groups were euthanized and the lungs harvested, homogenized and plated to quantitate M. tuberculosis burdens. Burdens from the right lung for each mouse and the median for each group of mice were recorded and summarized above in Table 23b.

Results:

In summary, and as shown above in Table 23b, Compound W exhibited robust in vivo efficacy against an experimentally induced M. tuberculosis lung infection in Balb/c mice. After 28 days of treatments at 30 and 100 mg/kg BID there were decreases in bacterial density compared to early and time-matched vehicle controls. Compound W demonstrated dose-dependent reductions of 0.2, 1.36 and 2.02 log reductions versus vehicle control when administered at 10, 30 and 100 mg/kg. In addition, doses of 10, 30, and 100 mg/kg BID of Compound W reduced bacterial burdens versus the early control by 0.64-2.63 logs suggesting Compound W has bactericidal activity against M. tuberculosis. The potent anti-tuberculosis drug Moxifloxacin, at 100 mg/kg QD, provided lung burden reduction versus the early and late controls as previously published. The reductions were less than those provided by Compound W administered at 100 mg/kg and similar to those at 30 mg/kg BID Compound W indicating that compound W exhibits anti-tuberculosis activity on par or better than Moxifloxacin in this assay.

Example 31

In Vitro Drug Combination Studies

To evaluate additional potential 2-drug combinations, these are compared first in an in vitro checkerboard experiments performed either in complete 7H9 broth or in whole blood inoculated with M. tuberculosis H37Rv in log phase growth. Concentrations of 0, 0.25×MIC, MIC, 4×MIC and (if clinically relevant) 16×MIC are tested for each compound. Pyrazinamide combinations may also be examined at pH 6.0, where its MIC is 50 µg/ml. For combinations with promising results, a similar checkerboard may be performed against nutrient-starved M. tuberculosis in PBS, to gain insight into the combination's activity against non-replicating organisms. Duplicate wells will be used for each concentration pair. Activity will be assessed by quantitative CFU counts performed after 0 and 7 days of incubation. Samples will be washed with PBS prior to plating.

Example 32

In Vitro Drug Combination Studies Using the Whole Blood Assay

The activity of selected 2-drug combinations against intracellular bacilli is also compared in a whole blood culture assay in which blood from healthy volunteers is inoculated with an aliquot of *M. tuberculosis* and increasing concentrations of drug in a checkerboard fashion similar to that described above. Drug concentrations of 0, 0.25×MIC, MIC, 4×MIC and (if clinically relevant) 16×MIC is tested for each drug. Viable CFU counts are estimated after 0 and 3 days of incubation by washing the cells, osmotically lysing them, inoculating the lysate into MGIT liquid culture bottles and incubating on the cultures on the MGIT system, where the time-to-positivity results are applied to a standard curve to estimate the change in log CFU for treatment groups compared to pre-treatment and drug-free controls.

Example 33

In Vitro Drug Combination Studies Using the Hollow Fiber Cartridge System

The hollow fiber cartridge system (HFS) is purchased from FiberCell (Frederick, Md.) and is used for the measurement of bactericidal and sterilizing activity for drug combinations. The peripheral compartments of HFS is inoculated with 7.5 log 10 CFU of *M. tuberculosis* in log-phase growth and is incubated at 37° C. under 5% CO2. The peripheral compartment of each HFS is sampled on days 0, 7, 14, 21, and 28 and samples are washed twice with normal saline to remove any drug carryover. The bacterial cultures are inoculated on Middlebrook 7H10 agar supplemented with 10% OADC to enumerate the total bacillary population as well as on agar supplemented with either drug or experimental compound to determine the resistant subpopulations.

Drugs and experimental compounds are administered to the central compartment of each HFS via a computer-controlled syringe pump. For pharmacokinetic matching, drugs and experimental compounds are administered at the same time to achieve a peak concentration of both isoniazid and rifampin at 1 h. The central compartments of the HFSs are sampled 12 times during the first 48 h and drug and experimental compound concentrations are then measured.

The results of the bactericidal-effect experiments are useful in the design of experiments for measuring sterilizing effect. Pharmacokinetic and statistical analysis uses the ADAPT 5 program, which has the maximum-likelihood solution via the expectation maximization algorithm. A one-compartment model with first-order input and elimination is utilized and a two-way analysis of variance (ANOVA) with Bonferroni post-test correction is used to compare bacterial burden from triplicate HFSs at each time point in GraphPad Prism version 5.00 (GraphPad Software, CA).

Example 34

**In Vivo Mouse *M. tuberculosis* (Erdman) Lung Infection Model**

Animals: female BALB/c mice (5-7 weeks of age; 6/group), are obtained from Jackson Laboratories, (Bar Harbor, Me.) and are housed and maintained in a BSL3 facility in accordance with the Guide to the Care and Use of Experimental Animals.

Bacterial Strain and Stocks

*M. tuberculosis* ATCC 35801 (strain Erdman) is obtained from the ATCC (Manassas, Va., USA). The organism is grown in 20 tubes of modified 7H10 broth (pH 6.6; 7H10 agar formulation with agar and malachite green omitted) with 10% OADC (oleic acid, albumin, dextrose, catalase) enrichment (BBL Microbiology Systems, Cockeysville, Md., USA) and 0.05% Tween 80 for 5-10 days on a rotary shaker at 37° C. The cultures are pooled and diluted to 100 Klett units [equivalent to $5 \times 10^7$ colony forming units (cfu)/mL] (Photoelectric Colorimeter; Manostat Corp., New York, N.Y., USA). The culture is aliquotted and frozen at −70° C. On the day of infection, the culture is thawed and the final inoculum is determined. The final inoculum size is determined by diluting to $5 \times 10^{-2}$ and plating 0.1 mL, in triplicate, on 7H10 agar plates (BBL Microbiology Systems) supplemented with 10% OADC enrichment. The plates are incubated at 37° C. in ambient air for 4 weeks.

Mouse *M. tuberculosis* (Erdman) Infection Model

Intranasal infection groups of mice are anaesthetized by intramuscular delivery of a telazol (45 mg/kg)/xylazine (7.5 mg/kg) cocktail (Lederle Parenterals, Carolina, Puerto Rico and Bayer Corp., Shawnee Mission, Kans., USA, respectively) and subsequently infected intranasally with ~$10^2$ viable *M. tuberculosis* in a 20 µL volume. The timetable for the experiment is as follows: day 0, intranasal infection; on study day 24 early controls are sacrificed for lung burden determination and treatment is started. 28 days post initiation of treatment 52 days post infection, all treated mice and late controls are sacrificed for lung burden determination.

For bacterial load determination mice are sacrificed by CO2 asphyxiation. Right lungs are aseptically removed and ground in a sealed tissue homogenizer (IdeaWorks! Laboratory Devices, Syracuse, N.Y., USA). The number of viable organisms is determined by serial dilution and titration on 7H10 agar plates. Plates are incubated at 37° C. in ambient air for 4 weeks prior to counting.

Groups for three compound combination studies:
Early Controls
Late Controls
TMC-207 25 mg/kg+pyrazinamide 150 mg/kg+Rifapentine 10 mg/kg
TMC-207 25 mg/kg+VRT-1064001 100 mg/kg+pyrazinamide 150 mg/kg
TMC-207 25 mg/kg+Moxifloxacin 100 mg/kg+pyrazinamide 150 mg/kg
Compound W 100 mg/kg+Rifapentine 10 mg/kg+pyrazinamide 150 mg/kg
Moxifloxacin 100 mg/kg+Rifapentine 10 mg/kg+pyrazinamide 150 mg/kg
Compound W 100 mg/kg+linezolid 100 mg/kg+pyrazinamide 150 mg/kg
Compound W 100 mg/kg+clofazimine 20 mg/kg+pyrazinamide 150 mg/kg
Compound W 100 mg/kg+Moxifloxacin 100 mg/kg+pyrazinamide 150 mg/kg Formulation Preparation:

Group #3: TMC-207 is formulated in 20% Hydroxypropyl-B-Cyclodextrin and treatment occurs in the morning. In the afternoon, (minimum of 2 hrs between dosing) all other compounds are combined for the groups of mice in one tube and dissolve by first adding 50% polyethylene glycol until dissolved and then adding 50% ddH$_2$O.

BALB/c mice (6/group) are challenged intranasally (IN) with *M. tuberculosis* (Erdman; ATCC) at a dose of $1 \times 10^2$ cfu/mouse. After 24 days a single group of mice (Early Control (EC)) is euthanized and the lungs harvested, homogenized and plated to quantify *M. tuberculosis* burdens. Compounds are administered at 10, 30, or 100 mg/kg BID for 28 days. After 28 days of treatment the groups are euthanized and the lungs harvested, homogenized and plated to quantify *M. tuberculosis* burdens.

REFERENCES

Combinations of antibiotics and non-antibiotic drugs enhance antimicrobial efficacy. Ejim L, Farha M A, Falconer S B, Wildenhain J, Coombes B K, Tyers M, Brown E D, Wright G D. Nat Chem Biol. 2011 June; 7(6):348-50.

Selection of a moxifloxacin dose that suppresses drug resistance in *Mycobacterium tuberculosis*, by use of an in vitro pharmacodynamic infection model and mathematical modeling. Gumbo T, Louie A, Deziel M R, Parsons L M, Salfinger M, Drusano G L. J Infect Dis. 2004 Nov. 1; 190(9):1642-51.

Pharmacokinetics and whole-blood bactericidal activity against *Mycobacterium tuberculosis* of single doses of PNU-100480 in healthy volunteers. Wallis R S, Jakubiec W M, Kumar V, Silvia A M, Paige D, Dimitrova D, Li X, Ladutko L, Campbell S, Friedland G, Mitton-Fry M, Miller P F. J Infect Dis. 2010 Sep. 1; 202(5):745-51.

Example 35

Evaluation of the Anti-Tuberculosis Activity of Lead Compounds in Mice

Phase 1—Evaluation of Lead Compounds as Monotherapy Against Established TB in Mice Methods The experimental scheme is presented in Table 24. BALB/c mice will be infected with ~100 CFU of virulent *M. tuberculosis* H37Rv in order to produce a stable infection with *M. tuberculosis* of ~$10^6$ organisms in the lung at the initiation of treatment 5 weeks later (D0). Drugs will be prepared in an appropriate vehicle. Treatment will be administered daily, 5 days per week, by esophageal gavage unless subcutaneous injection is required. Outcomes will be lung CFU counts after 4 weeks of treatment. Quantitative cultures of lung samples will be performed in duplicate on OADC-enriched 7H11 agar medium. Group mean differences in lung CFU counts will be compared using one-way ANOVA with Dunnett's post-test (GraphPad Prism 4) to adjust for multiple comparisons.

Explanation of Treatment Groups

Untreated: This is the negative control group. Five mice will be sacrificed the day after *M. tuberculosis* infection (D-34) and on the day of treatment initiation (D0) to determine the number of bacilli implanted and the extent of multiplication from D-35 to D0, respectively. Additional mice will be sacrificed 4 weeks for microbiological characterization of the natural history of infection.

Isoniazid (INH): mice in this control group will receive this first-line drug known for its strong bactericidal activity against actively multiplying organisms but reduced activity against non-actively multiplying organisms.

Rifampin (RIF): mice in this control group will receive this first-line drug known for its strong bactericidal activity against non-actively multiplying organisms.

Test compound A (A): mice in this group will receive a first compound of formula (I) ("A") at one of 3 doses.

Test compound B (B): mice in this group will receive a second compound of formula (I) ("B") at one of 3 doses.

TABLE 24

Experimental scheme for dose-ranging activity study

| Regimen | No. of mice killed by time point | | | |
|---|---|---|---|---|
| [dose(mg/kg)] | D − 35 | D 0 | Wk 4 | Total |
| Untreated | 5 | 5 | 5 | 15 |
| INH (10) | | | 5 | 5 |
| RIF (10) | | | 5 | 5 |
| A (10) | | | 5 | 5 |
| A (30) | | | 5 | 5 |
| A (100) | | | 5 | 5 |
| B (10) | | | 5 | 5 |
| B (30) | | | 5 | 5 |
| B (100) | | | 5 | 5 |
| Total | 5 | 5 | 45 | 55 |

The experiment will also include a PK study to determine the 24-hour serum and lung PK profile for each test compound and dose in infected mice during the 2nd week of treatment. Mice will be sacrificed according to the scheme in Table 25, around the dose administered on Wednesday or Thursday during the 2nd week of treatment. Three mice will be sacrificed for each drug and dose at the indicated time points before and after drug administration. At the time of sacrifice, mice will be anesthetized with isoflurane, using the drop method, and exsanguinated by cardiac puncture. Serum will be harvested and frozen at −80° C. The right lung will be harvested, homogenized thoroughly and frozen at −80° C. Samples will be mixed with acetonitrile before shipment to Vertex where concentrations of compounds A and B will be determined.

TABLE 25

Scheme for serum and lung PK sub-study
No of mice killed by time point

| 0 h | 0.5 h | 1 h | 2 h | 4 h | 8 h | Total |
|---|---|---|---|---|---|---|
| 3 | 3 | 3 | 3 | 3 | 3 | 18 |

To perform serum and lung PK for all 3 doses of both drugs, a total of 108 mice will be required.

Phase 2—Evaluation of Compound Activity in Combination with Existing TB Drugs

1) Experiment to Identify the Best Companion Drugs for the Test Compounds

The interaction of Compounds A and/or B with existing TB drugs will be evaluated first in 2 in vitro models to inform the design of long-term combination therapy studies with 3- and/or 4-drug combinations that utilize relapse rate as the measure for stable cure and thereby promote the most efficient use of limited resources.

Methods

In Vitro Checkerboard Assay

Potential 2-drug combinations will be compared first in in vitro checkerboard experiments performed either in complete 7H9 broth or in whole blood inoculated with *M. tuberculosis* H37Rv in log phase growth. Drug concentrations of 0, 0.25× MIC, MIC, 4×MIC and (if clinically relevant) 16×MIC will be tested for each drug. PZA will be evaluated at normal pH, where its MIC against *M. tuberculosis* H37Rv is 250 µg/ml. It may also be examined at pH 6.0, where its MIC is 50 µg/ml. For combinations with promising results, a similar checkerboard may be performed against nutrient-starved *M. tuberculosis* in PBS, to gain insight into the combination's activity against non-replicating organisms.

A sample experimental scheme for a checkerboard experiment is presented in Table 26. Duplicate wells will be used for each concentration pair. Activity will be assessed by quantitative CFU counts performed after 0 and 7 days of incubation. Samples will be washed with PBS prior to plating.

In Vitro Whole Blood Assay

Activity of selected 2-drug combinations against intracellular bacilli will be compared in a whole blood culture assay in which blood from healthy volunteers is inoculated with an aliquot of *M. tuberculosis* and increasing concentrations of drug in a checkerboard fashion similar to that described above. Drug concentrations of 0, 0.25×MIC, MIC, 4×MIC and (if clinically relevant) 16×MIC will be tested for each drug, as depicted in Table 26. Viable CFU counts are estimated after 0 and 3 days of incubation by washing the cells, osmotically lysing them, inoculating the lysate into MGIT liquid culture bottles and incubating on the cultures on the MGIT system, where the time-to-positivity results are applied to a standard curve to estimate the change in log CFU for treatment groups compared to pre-treatment and drug-free controls.

Rationale for drugs to be tested.

Isoniazid (INH): first-line drug known for its strong bactericidal activity against actively multiplying organisms but reduced activity against non-actively multiplying organisms.

Rifampin (RIF): first-line drug known for its moderate activity against actively multiplying organisms, but strong bactericidal activity against non-actively multiplying organisms (sterilizing activity).

Pyrazinamide (PZA): first-line drug known for having pH-dependent activity against *M. tuberculosis* in vitro, but significant sterilizing activity in mice, presumably against *M. tuberculosis* inside activated macrophages.

Moxifloxacin (MXF): key second-line drug known for its strong bactericidal activity against actively multiplying organisms but reduced activity against non-actively multiplying organisms. MXF is being studied in clinical trials to evaluate whether it belongs as a first-line TB drug.

Linezolid (LZD): second-line drug commonly used in salvage therapy for recalcitrant drug-resistant TB. LZD may also serve as a surrogate for new oxazolidinones in clinical development.

Cmpd A (A): Vertex test compound A.

Cmpd B (B): Vertex test compound B.

TABLE 26

Sample scheme for checkerboard experiment

| Conc of Drug 2 | Concentration of Drug 1: 0 | 0.25x MIC | MIC | 4x MIC | 16x MIC |
|---|---|---|---|---|---|
| 0 | | | | | |
| 0.25x MIC | | | | | |
| MIC | | | | | |
| 4x MIC | | | | | |
| 16x MIC | | | | | |

2) Experiment to Evaluate the Sterilizing Activity of Novel Combinations Including Test Compounds of Formula (I).

At present, the gold standard for measuring a regimen's sterilizing activity in the mouse model is the assessment of relapse after discontinuation of therapy. With available regimens as standard comparators, such experiments require 7-10 months to complete due to the requirement for a treatment-free follow-up period of ≥3 months to determine the proportion of mice with culture-positive relapse. Because of the time- and cost-consuming nature of such experiments, it is imperative to utilize the most efficient study designs possible. By establishing the relative activity of various 2-drug building blocks in the short-term infection model as described above, the most promising regimens can be carried forward into 1 or 2 relapse-based studies to compare the activity of such regimens to that of the standard first-line regimen and/or that of more potent experimental regimens.

A sample experimental scheme is presented in Table 26a. In this example, the effect of adding test compound A to the first-line regimen or substituting it for INH is examined, as is the substitution of test compound B for ethambutol or amikacin in an idealized second-line regimen comprised of existing drugs. In each case, the regimens in question are truncated after treatment of reduced duration in order to demonstrate whether the incorporation of test compound could have a treatment-shortening effect. The primary endpoint is the proportion of mice with positive cultures (i.e., relapse) 3 months after the discontinuation of therapy. Mice will be infected by the aerosol route with approximately 4 $\log_{10}$ CFU on Day −14. The infection will incubate for 14 days before mice are randomized into treatment groups as indicated and treatment is begun. The indicated regimens will be administered as described above. Group mean lung CFU counts will be compared by one-way ANOVA with Bonferroni's post-test to adjust for multiple comparisons. Additional cohorts of 15 mice will be held for 3 months after completing various durations of treatment before being sacrificed for relapse determination. The entire lung homogenate will be plated on 7H11 agar. The proportions of mice with culture-positive relapse will be compared using Fisher's Exact test with adjustment for multiple corrections.

TABLE 26a

Example of an experimental scheme to assess the sterilizing activity of promising regimens containing test compounds
Time point and No. of mice to sacrifice**

| Regimen* | D-13 | D0 | M2 | M4 (+3) | M5 (+3) | M6 (+3) | Total |
|---|---|---|---|---|---|---|---|
| 2RHZ/3RH | 6 | 6 | 5 | 5 (15) | 5 (15) | | 57 |
| 2RHZA/3RHA | | | 5 | 5 (15) | 5 (15) | | 45 |
| 2RAZ/3RA | | | 5 | 5 (15) | 5 (15) | | 45 |
| 2MEZAmk/4ME | | | 5 | 5 | 5 (15) | 5 (15) | 50 |
| 2MBZAmk/4MB | | | 5 | 5 | 5 (15) | 5 (15) | 50 |
| 2MEZB/4MEB | | | 5 | 5 | 5 (15) | 5 (15) | 50 |
| Total | 6 | 6 | 30 | 30 (45) | 30 (90) | 15 (45) | 297 |

*R, RIF 10 mg/kg; H, INH 10 mg/kg; Z, PZA 150 mg/kg; A, Vertex test compound A; B, Vertex test compound B; M, MXF 100 mg/kg; E, ethambutol 100 mg/kg; Amk, amikacin 30 mg/kg

**Time points are shown in days (D) (day-13 [D-13] or day 0 [D0]) or months (M) (e.g., 2 months = M2) of treatment. (+3) indicates that the mice are held for 3 months after the completion of treatment at the indicated time point.

Explanation of treatment groups

2RHZ/3RH: first-line regimen control consisting of 2 months of RIF, INH, and PZA, followed by 3 months of RIF and INH.

2RHZA/3RHA: test regimen in which Vertex test compound A is added to the first-line regimen.

2RAZE/3RA: test regimen in which Vertex test compound A is substituted for INH in the first-line regimen.

2MEZAmk/4ME: second-line regimen control consisting of 2 months of MXF, ethambutol, PZA and amikacin, followed by 4 months of MXF and ethambutol.

2MEZAmk/4ME: test regimen in which Vertex test compound B is substituted for ethambutol in the second-line regimen.

2MEZAmk/4ME: test regimen in which Vertex test compound B is substituted for amikacin in the second-line regimen.

Example 36

Susceptibility Testing in Liquid Media

Compounds of this invention were tested for antimicrobial activity by susceptibility testing in liquid media. Such assays were performed within the guidelines of the latest CLSI document governing such practices: "M07-A8 Methods for Dilution Antimicrobial Susceptibility Tests for Bacteria that Grow Aerobically; Approved Standard—Eighth Edition (2009)". Other publications such as "Antibiotics in Laboratory Medicine" (Edited by V. Lorian, Publishers Williams and Wilkins, 1996) provide essential practical techniques in laboratory antibiotic testing. The specific protocols used were as follows:

Protocol #1: Gyrase MIC Determination of Compounds Using Microdilution Broth Method Materials:
Round bottom 96-well microtiter plates (Costar 3788)
Mueller Hinton II agar plates (MHII; BBL premix)
Mueller Hinton II liquid broth (MHII; BBL premix)
BBL Prompt Inoculation System (Fisher B26306)
Test Reading Mirror (Fisher)
Agar plates with bacteria streaked to single colonies, freshly prepared
Sterile DMSO
Human serum (U.S. Biologicals S1010-51)
Laked horse blood (Quad Five 270-100)
Resazurin 0.01%
Sprague Dawley Rat serum (U.S. Biologicals 1011-90B or Valley BioMedical AS3061SD)
Pooled Mouse serum (Valley BioMedical AS3054)
Strains (Media, Broth and Agar):
1. *Staphylococcus aureus* ATCC #29213
   a. MHII
   b. MHII+50% human serum
   c. MHII+50% rat serum
   d. MHII+50% mouse serum
2. *Staphylococcus aureus* ATCC #29213 GyrB T173I (MHII)
3. *Staphylococcus aureus*, JMI collection strains; see table 26b (MHII)
4. *Enterococcus faecalis* ATCC #29212 (MHII+3% laked horse blood)
5. *Enterococcus faecium* ATCC #49624 (MHII+3% laked horse blood)
6. *Streptococcus pneumoniae* ATCC #10015 (MHII+3% laked horse blood)

Inoculum Prep (for all Strains Other than *S. aureus*+50% Sera):
1. Using the BBL Prompt kit, picked 5 big or 10 small, well separated colonies from culture grown on the appropriate agar medium as indicated above and inoculated 1 mL of sterile saline provided in the kit.
2. Vortexed the wells for ~30 s to provide a suspension of ~$10^8$ cells/mL. Actual density could be confirmed by plating out dilutions of this suspension.
3. Diluted the suspension 1/100 by transferring 0.15 mL of cells into 15 mL (~$10^6$ cells/mL) sterile broth (or see below) for each plate of compounds tested, then swirled to mix. If more than 1 plate of compounds (>8 compounds) were tested, volumes were increased accordingly.
   a. For *E. faecalis*, *E. faecium* and *S. pneumoniae*: 14.1 mL MHII+0.9 mL laked horse blood was used.
4. Used 50 µl cells (~$5 \times 10^4$ cells) to inoculate each microtiter well containing 50 µl of the drug diluted in broth (see below).

Drug Dilutions, Inoculation, MIC Determination:
1. All drug/compound stocks were prepared at 12.8 mg/mL concentration, usually in 100% DMSO.
2. Diluted drug/compound stocks to 200× desired final concentration in 50 µL DMSO. If starting concentration of MICs was 8 µg/mL final concentration, then required 6.25 µL of stock+43.75 µL DMSO. Each 200× stock was placed in a separate row of column 1 of a new 96 well microtiter plate.
3. Added 25 µL of DMSO to columns 2-12 of all rows of the microtiter plate containing 200× compound stocks and serially diluted 25 µL from column 1 through column 11, changed tips after each column. i.e. 25 µL compound+25 µL DMSO=2× dilution. Left "no compound" DMSO well at the end of the series for control.
4. For each strain tested (except *S. aureus*+50% human serum), prepared two microtiter plates with 50 µL of MHII broth using a Matrix pipettor.
5. Transferred 0.5 µL of each dilution (w/Matrix auto-pipettor) to 50 µL of medium/microtiter well prior to the addition of 50 µl of cells. The usual starting concentration of compound was 8 µg/mL after the 1/200 dilution into medium+cells−compound concentrations decreased in 2× steps across the rows of the microtiter plate. All MICs were done in duplicate.
6. All wells were inoculated with 50 µl of diluted cell suspension (see above) to a final volume of 100 µl.
7. After inoculum was added, mixed each well thoroughly with a manual multichannel pipettor; same tips were used going from low to high concentration of drug in the same microtiter plate.
8. Plates were incubated at 37° C. for at least 18 hours.
9. Plates were viewed with a test reading mirror after 18 hours and the MIC was recorded as the lowest concentration of drug where no growth was observed (optical clarity in the well).

Preparation of *S. aureus*+50% Human Serum, *S. aureus*+50% Rat Serum or *S. aureus*+50% Mouse Serum.
1. Prepared 50% serum media by combining 15 mL of MHII+15 mL human serum–total 30 mL. Increased volume in 30 mL increments when more than 1 compound plate was tested.
2. Used the same BBL Prompt inoculum of *S. aureus* ATCC #29213 as described above, diluted 1/200 by transferring 0.15 mL of cells into 30 mL ($5 \times 10^5$ cells/mL) of the 50% human serum media prepared above and swirled to mix.
3. Filled all test wells of the desired number of microtiter plates with 100 µL, cells in 50% serum media.
4. Transferred 0.5 µL, of each compound dilution (w/Matrix auto-pipettor) to 100 µL, of cells/media. The usual starting concentration of compound was 8 µg/mL after the 1/200 dilution into medium+cells−compound concentrations decreased in 2× steps across the rows of a microtiter plate. All MICs were done in duplicate.
5. Mixed each well thoroughly with a manual multichannel pipettor; same tips were used going from low to high concentration of drug in the same microtiter plate.
6. Plates were incubated at 37° C. for at least 18 hours. After incubation, added 25 µL of 0.01% Resazurin to each well and continued to incubate at 37° C. for at least 1 additional hour or until the Resazurin color changes.
7. Plates were viewed with a test reading mirror and the MIC was recorded. When using Resazurin, the color of the dye changed from a dark blue to a bright pink in wells with no growth. The lowest concentration of drug that turned the dye pink was the MIC.

Protocol 2: Gyrase MIC Determination of Compounds Against Gram Negatives Using Microdilution Broth Method Materials:
Round bottom 96-well microtiter plates (Costar 3788)
Mueller Hinton II agar plates (MHII; BBL premix)
Mueller Hinton II liquid broth (MHII; BBL premix)
BBL Prompt Inoculation System (Fisher b26306)
Test Reading Mirror (Fisher)
Agar plates with bacteria streaked to single colonies, freshly prepared
Sterile DMSO
Strains (MHII Media for all; Broth and Agar):
1. *Escherichia coli* AG100 WT
2. *Escherichia coli* AG100 tolC
3. *Haemophilus influenzae* (Rd1KW20) ATCC 51907
4. *Haemophilus influenzae* Rd0894 (AcrA−)

Inoculum Prep:
1. Using the BBL Prompt kit, picked 5 big or 10 small, well separated colonies from cultures grown on agar medium and inoculated 1 mL sterile saline that came with the kit.
2. Vortexed the wells for ~30 s to give a suspension of ~$10^8$ cells/mL. Actual density could be confirmed by plating out dilutions of this suspension.
3. Diluted the suspension 1/100 by transferring 0.15 mL of cells into 15 mL (~$10^6$ cells/mL) sterile broth (see below) for each plate of compounds tested, swirled to mix. If more than 1 plate of compounds (>8 compounds) was to be tested, increased volumes accordingly.
4. Used 50 μl cells (~$5\times10^4$ cells) to inoculate each microtiter well containing 50 μl of the drug diluted in broth (see below).

Drug Dilutions, Inoculation, MIC Determination:
1. All drug/compound stocks were prepared at 12.8 mg/mL concentration, usually in 100% DMSO.
2. Diluted drug/compound stocks to 200× desired final concentration in 50 μL DMSO. If starting concentration of MICs was 8 μg/mL final concentration, then required 6.25 μL of stock+43.75 μL DMSO. Each 200× stock was placed in a separate row of column 1 of a new 96 well microtiter plate.
3. Added 25 μL of DMSO to columns 2-12 of all rows of the microtiter plate containing 200× compound stocks and serially diluted 25 μL from column 1 through column 11, changed tips after each column. i.e. 25 μL compound+25 μL DMSO=2× dilution. Left "no compound" DMSO well at the end of the series for control.
4. For each strain tested, prepared two microtiter plates with 50 μL of MHII broth using a Matrix pipettor.
5. Transferred 0.5 μL of each dilution (w/Matrix autopipettor) to 50 μL of medium/microtiter well prior to the addition of 50 μl of cells. The usual starting concentration of compound was 8 μg/mL after the 1/200 dilution into medium+cells−compound concentrations decreased in 2× steps across the rows of a microtiter plate. All MICs were done in duplicate.
6. All wells were inoculated with 50 μl of diluted cell suspension (see above) to a final volume of 100 μl.
7. After inoculum was added, each well was mixed thoroughly with a manual multichannel pipettor; same tips were used going from low to high concentration of drug in the same microtiter plate.
8. Plates were incubated at 37° C. for at least 18 hours.
9. Plates were viewed with a test reading mirror after 18 hours and the MIC was recorded as the lowest concentration of drug where no growth was observed (optical clarity in the well).

MIC Determination:
Examined the test plates after the correct incubation time and read the MIC endpoint at the concentration where a marked reduction occurred in the appearance of growth on the test plate as compared to that of growth on the positive control plates.

TABLE 26b

MIC Values of Selected Compounds

| | | MIC (μg/ml) | |
|---|---|---|---|
| Strain/Special Condition | Protocol | Form A | Form B |
| *Staphylococcus aureus* ATCC 29213 | 1 | 4 | 4 |
| *Staphylococcus aureus* ATCC 29213 with 50% Human Serum | 1 | >8 | >8 |
| *Staphylococcus aureus* ATCC 29213 with 50% Rat Serum | 1 | >8.0 | >8 |
| *Staphylococcus aureus* ATCC 29213 with 50% Mouse Serum | 1 | 1 | 1 |
| *Staphylococcus aureus* ATCC 29213 GyrB T173I | 1 | >8 | >8 |
| *Enterococcus faecalis* ATCC 29212, with 3% Laked Horse Blood | 1 | 1 | 1 |
| *Enterococcus faecium* ATCC 49624 with 3% Laked Horse Blood | 1 | 4 | 4 |
| *Streptococcus pneumoniae* ATCC 10015, with 3% Laked Horse Blood | 1 | 0.25 | 0.25 |
| *Haemophilus influenzae* (Rd1 KW20) ATCC 51907 | 2 | 8 | 8 |
| *Haemophilus influenzae* Rd0894 (AcrA−) | 2 | 0.25 | 0.25 |
| *Escherichia coli* AG100 WT | 2 | >8 | 2 |
| *Escherichia coli* AG100 tolC | 2 | >8 | 2 |

| | | MIC (μg/ml) | |
|---|---|---|---|
| Strain/Special Condition | Protocol | Form C | Form X |
| *Staphylococcus aureus* ATCC 29213 | 1 | 4 | 4 |
| *Staphylococcus aureus* ATCC 29213 with 50% Human Serum | 1 | >8 | 8 |
| *Staphylococcus aureus* ATCC 29213 with 50% Rat Serum | 1 | >8.0 | 8 |
| *Staphylococcus aureus* ATCC 29213 with 50% Mouse Serum | 1 | 1 | 2 |
| *Staphylococcus aureus* ATCC 29213 GyrB T173I | 1 | >8 | >16 |
| *Enterococcus faecalis* ATCC 29212, with 3% Laked Horse Blood | 1 | 1 | 2 |
| *Enterococcus faecium* ATCC 49624 with 3% Laked Horse Blood | 1 | 4 | 4 |
| *Streptococcus pneumoniae* ATCC 10015, with 3% Laked Horse Blood | 1 | 0.25 | 0.25 |
| *Haemophilus influenzae* (Rd1 KW20) ATCC 51907 | 2 | 8 | 8 |
| *Haemophilus influenzae* Rd0894 (AcrA−) | 2 | 0.25 | 0.25 |
| *Escherichia coli* AG100 WT | 2 | >8 | >16 |

TABLE 26b-continued

MIC Values of Selected Compounds

| Escherichia coli AG100 tolC | 2 | >8 | 2 |
|---|---|---|---|

| Strain/Special Condition | Protocol | MIC (µg/ml) Amorphous di-Na salt |
|---|---|---|
| Staphylococcus aureus ATCC 29213 | 1 | 4 |
| Staphylococcus aureus ATCC 29213 with 50% Human Serum | 1 | 8 |
| Staphylococcus aureus ATCC 29213 with 50% Rat Serum | 1 | 8 |

| Strain/Special Condition | Protocol | MIC (µg/ml) Form C | Form X |
|---|---|---|---|
| Staphylococcus aureus ATCC 29213 with 50% Mouse Serum | 1 | 2 | |
| Staphylococcus aureus ATCC 29213 GyrB T173I | 1 | >16 | |
| Enterococcus faecalis ATCC 29212, with 3% Laked Horse Blood | 1 | 2 | |
| Enterococcus faecium ATCC 49624 with 3% Laked Horse Blood | 1 | 4 | |
| Streptococcus pneumoniae ATCC 10015, with 3% Laked Horse Blood | 1 | 0.25 | |
| Haemophilus influenzae (Rd1 KW20) ATCC 51907 | 2 | 8 | |
| Haemophilus influenzae Rd0894 (AcrA-) | 2 | 0.25 | |
| Escherichia coli AG100 WT | 2 | >16 | |
| Escherichia coli AG100 tolC | 2 | 2 | |

Example 37

Enzymology Studies

The enzyme inhibition activities of selected compounds of this invention were determined in the experiments described below:

DNA Gyrase ATPase Assay

The ATP hydrolysis activity of S. aureus DNA gyrase was measured by coupling the production of ADP through pyruvate kinase/lactate dehydrogenase to the oxidation of NADH. This method has been described previously (Tamura and Gellert, 1990, J. Biol. Chem., 265, 21342).

ATPase assays were carried out at 30° C. in buffered solutions containing 100 mM TRIS pH 7.6, 1.5 mM $MgCl_2$, 150 mM KCl. The coupling system contains final concentrations of 2.5 mM phosphoenol pyruvate, 200 µM nicotinamide adenine dinucleotide (NADH), 1 mM DTT, 30 ug/ml pyruvate kinase, and 10 ug/ml lactate dehydrogenase. The enzyme (90 nM final concentration) and a DMSO solution (3% final concentration) of the selected compound were added. The reaction mixture was allowed to incubate for 10 minutes at 30° C. The reaction was initiated by the addition of ATP to a final concentration of 0.9 mM, and the rate of NADH disappearance was monitored at 340 nanometers over the course of 10 minutes. The $K_i$ values were determined from rate versus concentration profiles.

Selected compounds of the present invention were found to inhibit S. aureus and E. coli DNA gyrase. Table 27a shows the inhibitory activity of these compounds in the S. aureus DNA gyrase inhibition assay and Table 27b shows the inhibitory activity of these compounds in the E. coli DNA gyrase inhibition assay.

TABLE 27a

Inhibition of S. aureus DNA Gyrase

| Selected Solid Form | $K_i$ (nM) |
|---|---|
| Form A | 26 |
| Form B | <25 |
| Form C | 27 |

TABLE 27b

Inhibition of E. coli DNA Topo IV

| Selected Solid Form | $K_i$ (nM) |
|---|---|
| Form A | 11 |
| Form B | <6 |
| Form C | <6 |

DNA Topo IV ATPase Assay

The conversion of ATP to ADP by S. aureus TopoIV enzyme was coupled to the conversion of NADH to NAD+, and the progress of the reaction was measured by the change in absorbance at 340 nm. TopoIV (64 nM) was incubated with the selected compound (3% DMSO final) in buffer for 10 minutes at 30° C. The buffer consisted of 100 mM Tris 7.5, 1.5 mM $MgCl_2$, 200 mM K·Glutamate, 2.5 mM phosphoenol pyruvate, 0.2 mM NADH, 1 mM DTT, 5 µg/mL linearized DNA, 50 µg/mL BSA, 30 µg/mL pyruvate kinase, and 10 µg/mL lactate dehyrodgenase (LDH). The reaction was initiated with ATP, and rates were monitored continuously for 20 minutes at 30° C. on a Molecular Devices SpectraMAX plate reader. The inhibition constant, Ki, was determined from plots of rate vs. concentration of selected compound fit to the Morrison Equation for tight binding inhibitors.

Selected compounds of the present invention were found to inhibit S. aureus DNA Topo IV. Table 27c shows the inhibitory activity of these compounds in the S. aureus DNA gyrase inhibition assay.

TABLE 27c

Inhibition of S. aureus DNA Topo IV

| Selected Solid Form | $K_i$ (nM) |
|---|---|
| Form A | <4 |
| Form B | 10 |
| Form C | 30 |

Many modifications and variations of the embodiments described herein may be made without departing from the scope, as is apparent to those skilled in the art. The specific embodiments described herein are offered by way of example only.

The invention claimed is:
1. A solid compound of formula (I):

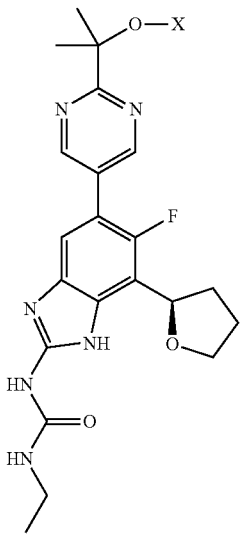

wherein X is —PO(OH)₂, —PO(OH)₂, —PO(OH)O⁻M⁺, or —PO(O⁻)₂·2M⁺, wherein M is a monovalent cation, wherein said solid is Free Form A, Free Form B, or Free Form C.

2. The solid compound of claim 1, wherein said solid is Free Form A.

3. The solid compound of claim 2, wherein said Free Form A is characterized by an X-ray powder diffraction pattern (XPRD) comprising at least three approximate peak positions (degrees 2θ±0.2) when measured using Cu K$_\alpha$ radiation, selected from the group consisting of 7.4, 7.8, 8.4, 14.0, 14.8, 16.8, 19.2, 20.5, 21.7, 24.0, and 26.7, when the XPRD is collected from about 5 to about 38 degrees 2θ.

4. The solid compound of claim 2, wherein said Free Form A is characterized by an X-ray powder diffraction pattern (XPRD) comprising at least three approximate peak positions (degrees 2θ±0.2) when measured using Cu K$_\alpha$ radiation, selected from the group consisting of 7.4, 7.8, 8.4, 16.8, 19.2, 21.7, and 24.0, when the XPRD is collected from about 5 to about 38 degrees 2θ.

5. The solid compound of claim 2, wherein said Free Form A is characterized by an X-ray powder diffraction pattern, as measured using Cu K$_\alpha$ radiation, substantially similar to FIG. 1.

6. The solid compound of claim 2, wherein said solid Free Form A is further characterized by an endothermic peak having an onset temperature of about 190.4° C. as measured by differential scanning calorimetry in which the temperature is scanned at about 10° C. per minute.

7. A method for preparing Free Form A of the compound of formula (I) according to claim 1 comprising precipitating the compound of formula (I) from an aqueous acidic solution.

8. The solid compound of claim 1, wherein said solid is Free Form B.

9. The solid compound of claim 8, wherein said Free Form B is characterized by an X-ray powder diffraction pattern (XPRD) comprising at least three approximate peak positions (degrees 2θ±0.2) when measured using Cu K$_\alpha$ radiation, selected from the group consisting of 7.5, 8.4, 13.9, 14.9, 15.9, and 23.5 when the XPRD is collected from about 5 to about 38 degrees 2θ.

10. The solid compound of claim 8, wherein said Free Form B is characterized by an X-ray powder diffraction pattern, as measured using Cu K$_\alpha$ radiation, substantially similar to FIG. 5.

11. The solid compound of claim 8, wherein said solid Free Form B is further characterized by an endothermic peak having an onset temperature of about 190.1° C. as measured by differential scanning calorimetry in which the temperature is scanned at about 10° C. per minute.

12. The solid compound of claim 1, wherein said solid is Free Form C.

13. The solid compound of claim 12, wherein said Free Form C is characterized by an X-ray powder diffraction pattern (XPRD) comprising at least three approximate peak positions (degrees 2θ±0.2) when measured using Cu K$_\alpha$ radiation, selected from the group consisting of 7.3, 9.2, 13.7, 14.4, and 18.4 when the XPRD is collected from about 5 to about 38 degrees 2θ.

14. A sodium salt of formula (IA):

(IA)

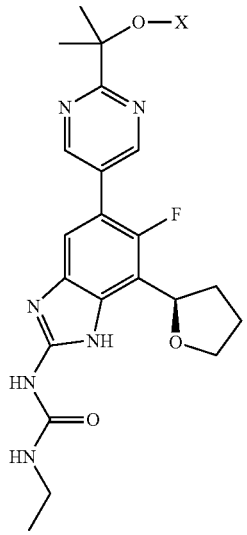

wherein X is —PO(OH)O⁻Na⁺ or —PO(P⁻Na⁺)₂, wherein said salt is disodium Salt Form X.

15. The solid compound of claim 14, wherein said Form X is characterized by an X-ray powder diffraction pattern (XPRD) comprising at least three approximate peak positions (degrees 2θ±0.2) when measured using Cu K$_\alpha$ radiation, selected from the group consisting of 6.3, 7.2, 10.7, 12.3, 12.7, 14.6, 16.9, 18.1, 18.8, 19.0, 19.69, 24.3, 24.9, and 27.3 when the XPRD is collected from about 5 to about 38 degrees 2θ.

16. The solid compound of claim 14, wherein said solid Form X is characterized by an X-ray powder diffraction pattern (XPRD) comprising at least three approximate peak positions (degrees 2θ±0.2) when measured using Cu K$_\alpha$ radiation, selected from the group consisting of 7.2, 10.7, 12.3, 12.7, 18.1, and 24.9, when the XPRD is collected from about 5 to about 38 degrees 2θ.

17. The solid compound of claim 14, wherein said solid Form X is characterized by an X-ray powder diffraction pattern (XPRD) comprising at least three approximate peak positions (degrees 2θ±0.2) when measured using Cu K$_\alpha$ radiation, selected from the group consisting of 7.2, 10.7, 12.3, 12.7, and 24.9, when the XPRD is collected from about 5 to about 38 degrees 2θ.

18. The solid compound of claim 14, characterized by an X-ray powder diffraction pattern, as measured using Cu $K_\alpha$ radiation, substantially similar to FIG. 11.

19. A pharmaceutical composition comprising a compound according to claim 1 and a pharmaceutically acceptable carrier, adjuvant, or vehicle.

20. A method of decreasing or inhibiting *Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium tuberculosis, Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci bacterial quantity in a biological sample comprising contacting said biological sample with a compound according to claim 19.

21. A method of treating a bacterial infection in a patient, comprising administering to said patient a composition according to claim 19, wherein the bacterial infection is characterized by the presence of one or more of *Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium tuberculosis, Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci.

22. The method according to claim 21, wherein the bacterial infection is selected from one or more of the following: upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections, uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial *pneumoniae* (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

23. The method according to claim 22, wherein the bacterial infection is selected from one or more of the following: community-acquired bacterial *pneumoniae* (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

24. A pharmaceutical composition comprising a compound according to claim 14 and a pharmaceutically acceptable carrier, adjuvant, or vehicle.

25. A method of decreasing or inhibiting *Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium tuberculosis, Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci bacterial quantity in a biological sample comprising contacting said biological sample with a composition according to claim 24.

26. A method of treating a bacterial infection in a patient, comprising administering to said patient a composition according to claim 24, wherein the bacterial infection is characterized by the presence of one or more of *Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium tuberculosis, Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci.

27. The method according to claim 26, wherein the bacterial infection is selected from one or more of the following: upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections, uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial *pneumoniae* (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

28. The method according to claim 27, wherein the bacterial infection is selected from one or more of the following: community-acquired bacterial *pneumoniae* (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

\* \* \* \* \*

UNITED STATES PATENT AND TRADEMARK OFFICE
CERTIFICATE OF CORRECTION

PATENT NO. : 9,018,216 B2
APPLICATION NO. : 13/945257
DATED : April 28, 2015
INVENTOR(S) : Hardwin O'Dowd et al.

It is certified that error appears in the above-identified patent and that said Letters Patent is hereby corrected as shown below:

In the Claims:

In claim 14,
col. 96, line 44, delete "-PO(P-Na+)2" and insert therefore -- -PO(O Na+)2--

Signed and Sealed this
Twenty-second Day of March, 2016

Michelle K. Lee
*Director of the United States Patent and Trademark Office*